US010670610B2

(12) United States Patent
Tarca et al.

(10) Patent No.: US 10,670,610 B2
(45) Date of Patent: Jun. 2, 2020

(54) BIOMARKER TEST FOR PREDICTION OR EARLY DETECTION OF PREECLAMPSIA AND/OR HELLP SYNDROME

(71) Applicant: WAYNE STATE UNIVERSITY, Detroit, MI (US)

(72) Inventors: Adi L. Tarca, Canton, MI (US); Nandor Than, Grosse Pointe Woods, MI (US); Gabor Juhasz, Budapest (HU); Adrienna Katalin Kekesi, Budapest (HU); Hamutal Meiri, Tel Aviv (IL); Zoltan Papp, Budapest (HU); Roberto Romero, Detroit, MI (US)

(73) Assignees: Wayne State University, Detroit, MI (US); The United States of America as represented by The Secretary, Department of Health and Human Services Office of Technology Transfer, National Institutes of Health, Bethesda, MD (US); Semmelweis University, Budapest (HU); Genesis Theranostix Korlatolt Felelossegu Tarsasag, Pécs (HU)

( * ) Notice: Subject to any disclaimer, the term of this patent is extended or adjusted under 35 U.S.C. 154(b) by 269 days.

(21) Appl. No.: 14/407,516

(22) PCT Filed: Jun. 13, 2013

(86) PCT No.: PCT/US2013/045709
§ 371 (c)(1),
(2) Date: Dec. 12, 2014

(87) PCT Pub. No.: WO2013/188686
PCT Pub. Date: Dec. 19, 2013

(65) Prior Publication Data
US 2016/0187347 A1 Jun. 30, 2016

Related U.S. Application Data

(60) Provisional application No. 61/699,193, filed on Sep. 10, 2012.

(30) Foreign Application Priority Data

Jun. 15, 2012 (HU) .................................. 201200368

(51) Int. Cl.
*G01N 33/68* (2006.01)
*C12Q 1/6883* (2018.01)
(52) U.S. Cl.
CPC ......... *G01N 33/689* (2013.01); *C12Q 1/6883* (2013.01); *G01N 2800/368* (2013.01); *G01N 2800/50* (2013.01)

(58) Field of Classification Search
None
See application file for complete search history.

(56) References Cited

U.S. PATENT DOCUMENTS

| 7,344,892 | B2 | 3/2008 | Thadhani et al. | |
| 2006/0067937 | A1* | 3/2006 | Karumanchi | A61K 31/4439 424/145.1 |
| 2008/0233583 | A1 | 9/2008 | Fisher et al. | |
| 2009/0280124 | A1 | 11/2009 | Labat et al. | |
| 2010/0016173 | A1 | 1/2010 | Nagalla et al. | |

FOREIGN PATENT DOCUMENTS

| WO | 99/64860 A2 | | 12/1999 | |
| WO | 02/32953 A2 | | 4/2002 | |
| WO | WO2009/097584 | * | 8/2009 | ............. G01N 33/68 |
| WO | WO 2011/017654 | * | 2/2011 | ............. G01N 33/50 |

OTHER PUBLICATIONS

Buimer et al., Placenta, 2008; 29: 444-453.*
Kramer et al., Reproductive Sciences, Mar. 2012; vol. 19, No. 3 (Supplement), Abstract: #87A.*
Scholl et al., Placenta, 2012; 33: 424-432. (Year: 2012).*
Kolla et al., Journal of Biomedicine and Biotechnology, vol. 2010, Article ID 952047, 10 pages; doi:10.1155/2010/952047. (Year: 2010).*
The website by https://www.healthline.com/health/hellp-syndrome#complication; downloaded Jul. 22, 2019 (Year: 2019).*
Faden et al., European Journal of Obstetrics & Gynecology and Reproductive Biology, 1997; 73: 37-42 (Year: 1997).*
Lee et al., Obstet Gynecol 2003;102:294-300 (Year: 2003).*
The website https://www.nichd.nih.gov/health/topics/preeclampsia/conditioninfo/treatments, downloaded Jan. 30, 2020 (Year: 2020).*
Blumenstein et al.: "A proteomic approach identifies early pregnancy biomarkers for preeclampsia: Novel linkages between a predisposition to preeclampsia and cardiovascular disease", Proteomics, 2009, vol. 9, pp. 2929-2945, DOI 10.1002/pmic.200800625.
Carmenta Bioscience, Inc., Matthew Cooper: "Carmenta Bioscience to Develop Serum Diagnostic Test for Preeclampsia from Stanford University", Business Wire, May 20, 2013.
Dexlin-Mellby et al.: "Tissue proteome profiling of preeclamptic placenta using recombinant antibody microarrays", Proteomics Clin. Appl., 2010, vol. 4, pp. 1-14, DOI 10.1002/prca.201000001.
(Continued)

*Primary Examiner* — Christina M Borgeest
(74) *Attorney, Agent, or Firm* — Jason D. Voight

(57) ABSTRACT

Disclosed are specific biomarkers that allow for early testing of preeclampsia/HELLP syndrome. Thus, a method is provided predicting preeclampsia in a pregnant woman. Also disclosed is a kit comprising means for assaying a sample from a pregnant woman for the concentrations of the specific biomarkers.

13 Claims, 17 Drawing Sheets
Specification includes a Sequence Listing.

(56) References Cited

OTHER PUBLICATIONS

Kang et al.: "Preeclampsia leads to dysregulation of various signaling pathways in placenta", Journal of Hypertension, 2011, vol. 29, No. 5, pp. 928-936, DOI:10.1097/HJH.0b013e328344a82c.

Kolla et al.: "Quantitative Proteomic (iTRAQ) Analysis of 1st Trimester Maternal Plasma Samples in Pregnancies at Risk for Preeclampsia", Journal of Biomedicine and Biotechnology, 2012, pp. 1-8, Article ID 305964, DOI: 10.1155/2012/305964.

Nishizawa et al.: "Comparative gene expression profiling of placentas from patients with severe preeclampsia and unexplained fetal growth restriction", Reproductive Biology and Endocrinology, 2011, vol. 9:107, pp. 1-12, DOI:10.1186/1477-7827-9-107.

Pennings et al.: "Integrative data mining to identify novel candidate serum biomarkers for pre-eclampsia screening", Prenatal Diagnosis, 2011, vol. 31, pp. 1153-1159, DOI: 10.1002/pd.2850.

Rasanen et al: "Comprehensive Maternal Serum Proteomic Profiles of Preclinical and Clinical Preeclampsia", Journal of Proteome Research, 2010, vol. 9, pp. 4274-4281.

Varkonyi et al.: "Microarray Profiling Reveals That Placental Transcriptomes of Early-onset HELLP Syndrome and Preeclampsia Are Similar", Placenta, 2011, vol. 32, pp. S21-S29.

Winn et al.: "Severe Preeclampsia-Related Changes in Gene Expression at the Maternal-Fetal Interface Include Sialic Acid-Binding Immunoglobulin-Like Lectin-6 and Pappalysin-2", Endocrinology, Jan. 2009, vol. 150(1), pp. 452-462.

* cited by examiner

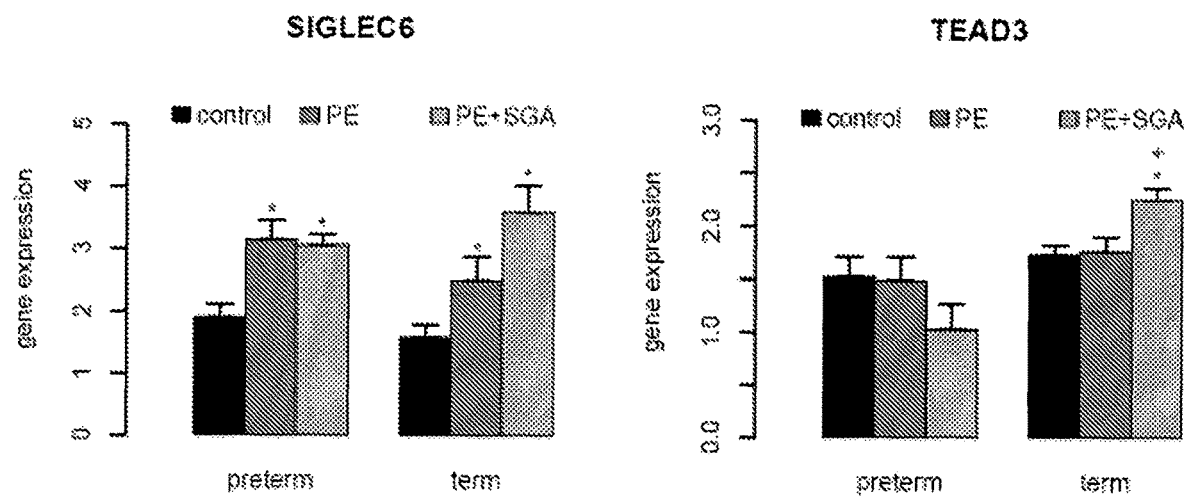
Figure 4OO
Figure 4PP
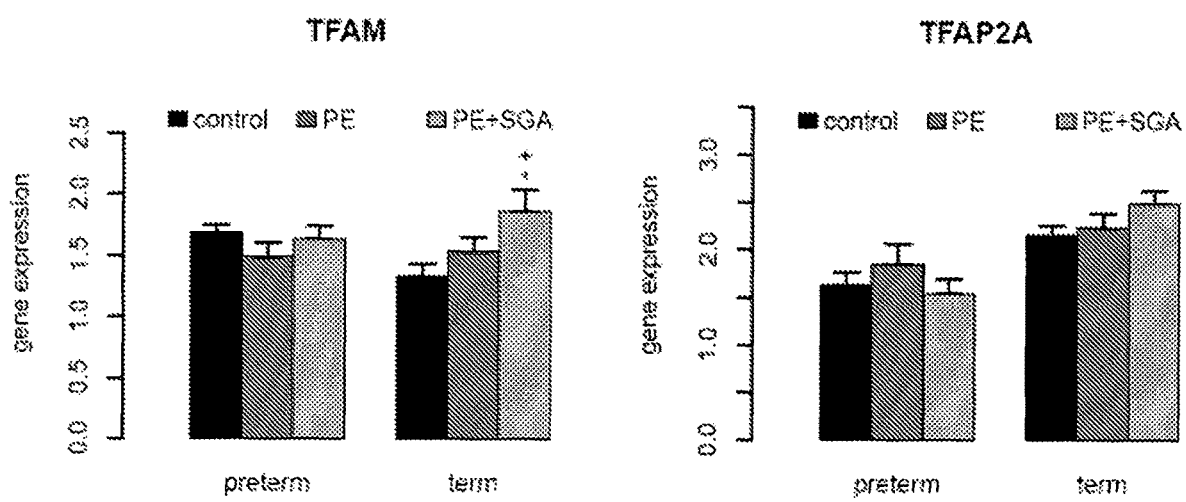
Figure 4QQ
Figure 4RR

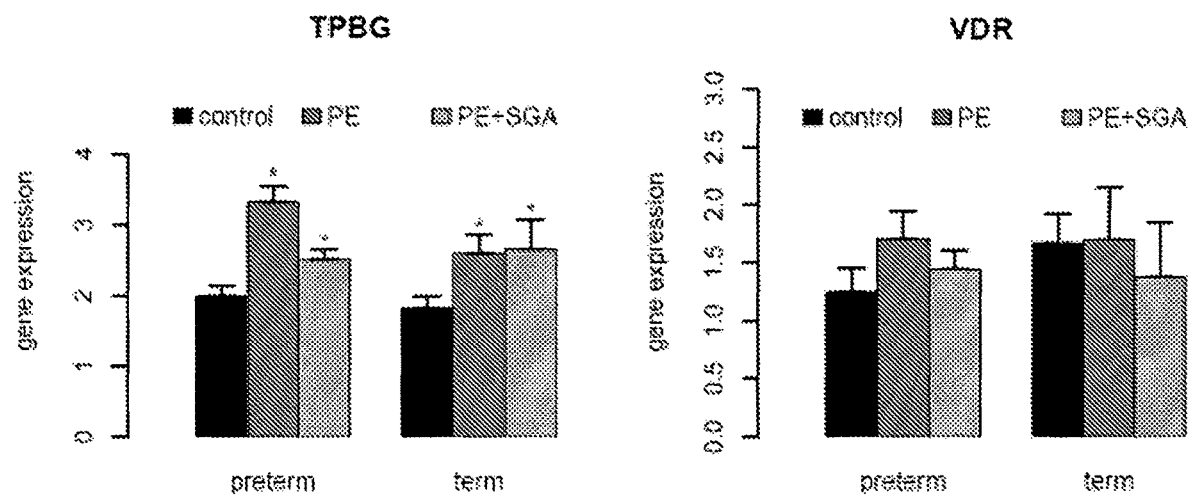
Figure 4SS
Figure 4TT
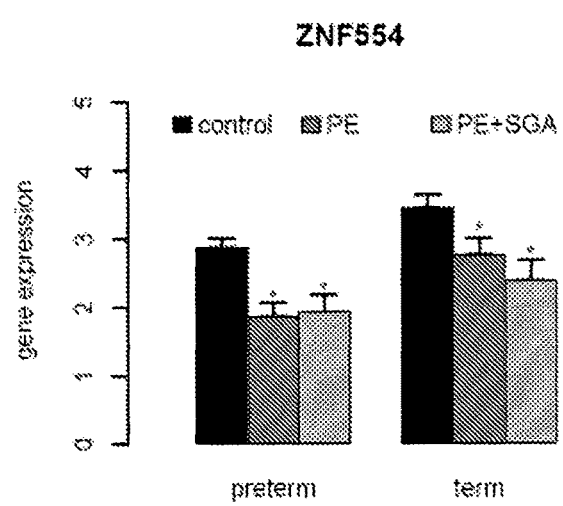
Figure 4UU

BIOMARKER TEST FOR PREDICTION OR EARLY DETECTION OF PREECLAMPSIA AND/OR HELLP SYNDROME

This is the national stage of International Application PCT/US2013/045709, filed Jun. 13, 2013, and claims priority to U.S. Provisional Application Ser. No. 61/699,193, filed Sep. 10, 2012.

This invention was made with government support under N01 HD023342 awarded by the National Institutes of Health (NIH). The government has certain rights in the invention.

FIELD OF THE DISCLOSURE

The present disclosure provides a test which can be used to predict and/or detect preeclampsia and/or Haemolysis, Elevated Liver enzymes and Low Platelets (HELLP) syndrome in pregnant women. More specifically, the disclosure provides a panel of biomarkers that can be used for early prediction and/or detection of preeclampsia and/or HELLP syndrome and may also allow the prediction and detection of closely related complications of pregnancy in early gestation such as including but not limited to implantation failure, and threatened and spontaneous miscarriage.

BACKGROUND OF THE DISCLOSURE

Preeclampsia is a syndrome defined by pregnancy-induced hypertension and proteinuria, which can lead to eclampsia (convulsions), and other serious maternal and/or fetal complications. Preeclampsia is originated in early gestation from the failure of implantation mechanisms and/or placental development, and is thus closely related to complications of pregnancy in early gestation such as including but not limited to implantation failure, and threatened and spontaneous miscarriage, Preeclampsia affects approximately 5-7% of pregnant women (approximately 8,370,000 pregnant women worldwide per year) and is a major cause of maternal and perinatal mortality. Furthermore, women with preeclampsia have an 8-fold higher risk of cardiovascular death later in their life, and offspring born from pregnancies affected by preeclampsia have an increased risk of metabolic and cardiovascular disease and mortality later in life.

The present diagnostic criteria for preeclampsia set by the United States National High Blood Pressure Education Program Working Group on High Blood Pressure in Pregnancy include new-onset hypertension coupled with proteinuria that develops after 20 weeks of gestation in women with previously normal blood pressures. These criteria further define preeclampsia as systolic or diastolic blood pressures of ≥140 and/or ≥90 mmHg, respectively, measured at two or more different time points, at least 4 hours (h) but not more than 1 week apart, as well as proteinuria of ≥300 mg protein in a 24 h urine sample, or two random urine specimens obtained at least 4 h but not more than 1 week apart containing ≥1+ protein on a dipstick.

Based on the timing of the clinical manifestation, preeclampsia has been historically classified into different subforms, such as "term" (≥37 weeks) and "preterm" (<37 weeks) or by using an alternative terminology "late-onset" and "early-onset" preeclampsia. The latter classification has not been uniformly used, but different studies have employed a range of gestational age cutoffs varying between 28 and 35 weeks for the distinction between early-onset and late-onset preeclampsia. Recently, it has been suggested to define 34 weeks as the gestational age cutoff between these two forms. It is important to note that preeclampsia may occur intrapartum or postpartum; thus, monitoring and evaluating the symptoms of preeclampsia should be continued during the postpartum period.

In 1954, it was first reported that preeclampsia may be associated with haemolysis, abnormal liver function and thrombocytopenia. Initially accepted to be a severe variant of preeclampsia, this group of symptoms later was suggested to constitute a separate clinical entity termed Haemolysis, Elevated Liver enzymes and Low Platelets (HELLP) syndrome. Supporting the idea that HELLP syndrome is a distinct condition, up to 20% of HELLP syndrome patients do not develop hypertension, 5-15% have minimal or no proteinuria and 15% show neither hypertension nor proteinuria. Moreover, laboratory findings in HELLP syndrome rarely correlate with the severity of hypertension or proteinuria.

In addition to the medical complications suffered by mothers and risks to the offspring, preeclampsia and HELLP syndrome cause approximately $7 billion in healthcare costs in the United States annually. Accordingly, there have been many attempts to provide a reliable predictive test for preeclampsia/HELLP syndrome. Previous attempts have involved assays for the concentrations of circulating biochemical markers in maternal blood but to date, the scientific literature on these approaches have been contradictory and inconclusive. There is a need in the art for new and improved methods of predicting and diagnosing these conditions.

SUMMARY OF THE DISCLOSURE

The present disclosure provides biomarker combinations that allow for the prediction and/or early detection of preeclampsia and/or HELLP syndrome, and may also allow the prediction and detection of closely related complications of pregnancy in early gestation such as but not limited to implantation failure, and threatened and spontaneous miscarriage.

One embodiment includes a method for assessing the presence or risk of preeclampsia in a female to determine the need for a treatment regimen comprising: determining levels of one or more of complement factor B; gelsolin isoform a precursor; hornerin, fetuin B; hemopexin precursor; apolipoprotein H precursor; fms-related tyrosine kinase 1; hydroxysteroid (17-β) dehydrogenase 1; leptin; lectin galactoside-binding soluble 14; pappalysin 2 or placenta-specific 1 in a biological sample obtained from the female; generating a dataset based on the determined levels; assessing the presence or risk of developing preeclampsia in the female based on the dataset; and determining a treatment regimen based on the assessed presence or risk.

Another embodiment includes a method for assessing the presence or risk of preeclampsia in a female to determine the need for a treatment regimen comprising: determining levels of one or more of complement factor B, hornerin, hemopexin precursor, hydroxysteroid (17-β) dehydrogenase 1, lectin galactoside-binding soluble 14 or pappalysin 2 in a biological sample obtained from the female; generating a dataset based on the determined levels; assessing the presence or risk of developing preeclampsia in the female based on the dataset; and determining a treatment regimen based on the assessed presence or risk.

In another embodiment, the assaying is performed for the levels of at least 3 biomarkers.

In another embodiment, the sample is a blood sample.

In another embodiment the sample is other body fluid, secretion or excretion (such as but not limited to cervicovaginal fluid, saliva, or urine) sample.

In another embodiment the sample is an amniotic fluid sample.

In another embodiment the sample is fetal cells obtained invasively or non-invasively.

In another embodiment, the sample is a placental sample.

In another embodiment, the biological sample is obtained before the 20$^{th}$ week of pregnancy, before the 19$^{th}$ week of pregnancy, before the 18$^{th}$ week of pregnancy, before the 17$^{th}$ week of pregnancy, before the 16$^{th}$ week of pregnancy, before the 15$^{th}$ week of pregnancy, before the 14$^{th}$ week of pregnancy, before the 13$^{th}$ week of pregnancy, before the 12$^{th}$ week of pregnancy, before the 11$^{th}$ week of pregnancy, before the 10$^{th}$ week of pregnancy, before the 9$^{th}$ week of pregnancy, before the 8$^{th}$ week of pregnancy, before the 7$^{th}$ week of pregnancy, before the 6$^{th}$ week of pregnancy, or after delivery.

In another embodiment, the treatment regimen is a therapeutic intervention.

In another embodiment, the therapeutic intervention prevents or reduces symptoms of preeclampsia before the symptoms manifest in the female and/or fetus.

Another embodiment includes a kit for assessing the presence or risk of preeclampsia in a female to determine the need for a treatment regimen comprising: detection mechanisms for determining levels of one or more of complement factor B; gelsolin isoform a precursor; hornerin, fetuin B; hemopexin precursor; apolipoprotein H precursor; fms-related tyrosine kinase 1; hydroxysteroid (17-β) dehydrogenase 1; leptin; lectin galactoside-binding soluble 14; pappalysin 2 or placenta-specific 1 in a biological sample obtained from the female; instructions how to (i) generate a dataset based on the determined levels; (ii) assess the presence or risk of developing preeclampsia in the female based on the dataset; and (iii) determine a treatment regimen based on the assessed presence or risk.

Another embodiment includes a kit for assessing the presence or risk of preeclampsia in a female to determine the need for a treatment regimen comprising: detection mechanisms for determining levels of one or more of complement factor B, hornerin, hemopexin precursor, hydroxysteroid (17-β) dehydrogenase 1, lectin galactoside-binding soluble 14 or pappalysin 2 in a biological sample obtained from the female; instructions how to (i) generate a dataset based on the determined levels; (ii) assess the presence or risk of developing preeclampsia in the female based on the dataset; and (iii) determine a treatment regimen based on the assessed presence or risk.

In another embodiment, the kit includes detection mechanisms for at least three markers.

In another embodiment, the kit includes detection mechanisms for all markers described above.

In another embodiment, the methods and kits measure levels of at least one marker described in the figures and examples described herein.

BRIEF DESCRIPTION OF THE FIGURES

FIG. 2.

FIG. 3A-3C shows that the expression of dark grey module genes changes in the same direction in preeclampsia subgroups. 4A-B) In each barplot, the left and right panels show significant differences ("*") in preterm and term preeclampsia samples, respectively. Gene expression 4A) and protein immunostainings 4B) show similar patterns in sub-groups of preeclampsia. When the change with preeclampsia in the preterm samples was significantly different than the change with preeclampsia in the term samples, a "+" sign indicates this interaction. Semiquantitative immunoscorings for four proteins 4B) validated gene expression data. 4C) Representative images from the four immunostainings. The same placenta from a preterm control (left, 29 weeks) and from a patient with preterm preeclampsia with SGA (right, 31 weeks) is shown for the four immunostainings (40× magnifications).

Figure 1:
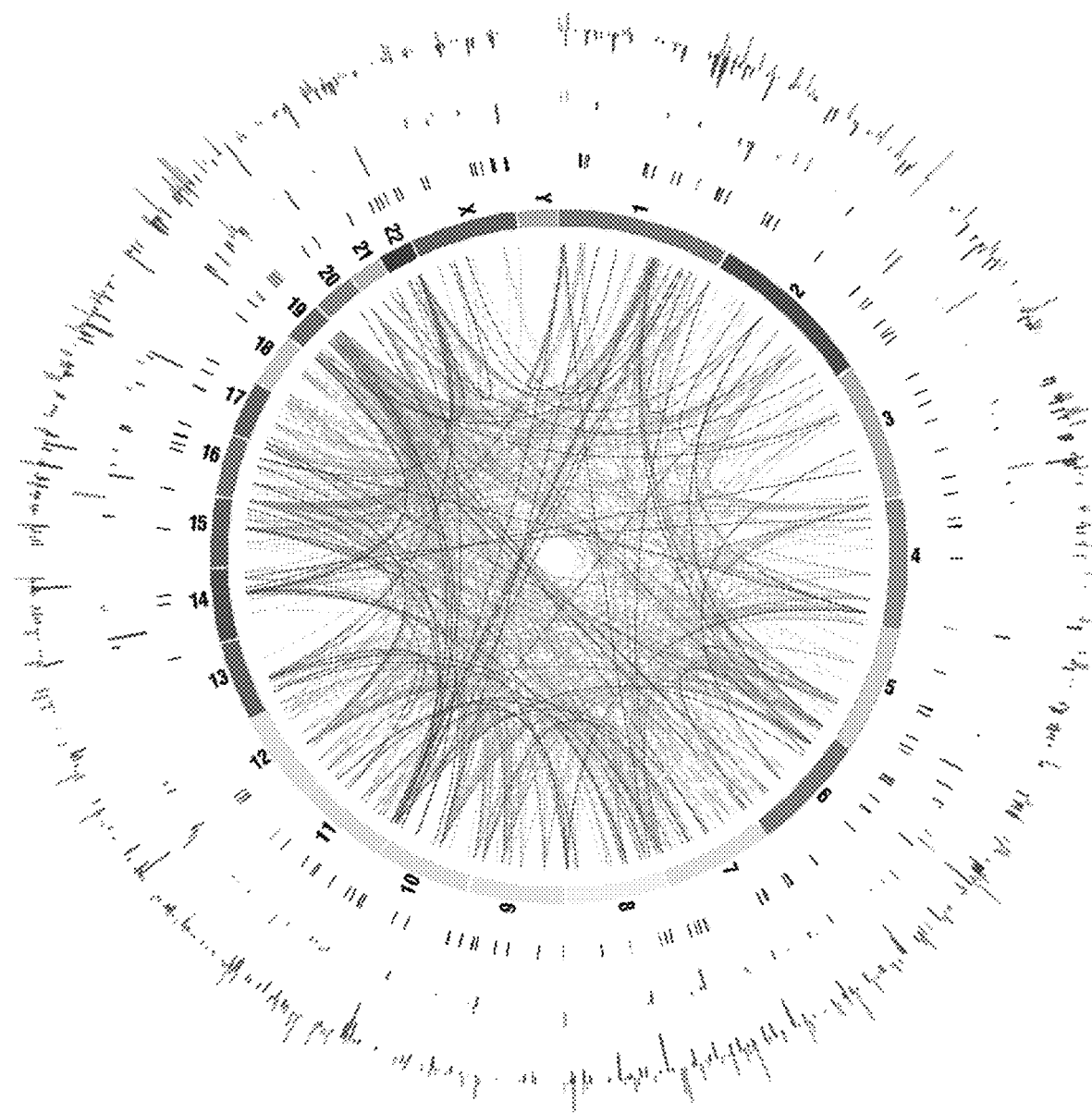
FIG. 1 shows a genomic map of differentially expressed genes in preeclampsia. Circos visualization shows Chromosomes with solid lines in the inner circle. Curved lines connect the genomic coordinates of genes and transcription regulatory genes that are significantly correlated. Significance was determined by fitting a linear model between the expression level of gene and transcription regulatory gene pairs in all samples while controlling for FDR at 5%. Curves represent positive and negative correlations. The second circle shows the genomic location of genes with predominant placental expression (PPE) (black lines: non differentially expressed; grey lines: up- or down-regulated). The third and fourth circles show the locations of differentially expressed transcription regulatory genes and non-regulatory genes, respectively with inward-oriented bars (down-regulated) and outward-oriented bars (up-regulated). The height of the bars in the third and fourth circles represents the magnitude of gene expression changes.

LGALS17A; MAPK13; NANOG; PAPPA; PAPPA2; PGF; PLAC1; POU5F1; SIGLEC6; TEAD3; TFAM; TFAP2A; TPBG; VDR; and ZNF554 respectively.

DETAILED DESCRIPTION

As described above, there have been several attempts carried out over the past few years to develop and validate biomarkers for the early prediction of preeclampsia and/or HELLP syndrome; however, their results were not satisfactory. A possible reason for this is that the early diagnosis of syndromes with a heterogeneous molecular background cannot be solved with the utilization of only one or two biomarker molecules.

The present disclosure describes the use of a multidisciplinary systems biological approach which led to the identification of a unique gene-, protein- and hormone biomarker panel, which are repeatedly detectable in the 7-9th weeks of gestation. This aim of the present disclosure was achieved by the inclusion of several high-dimensional techniques: 1) whole genome transcriptomics of the placenta; 2) high-throughput qRT-PCR expressional profiling of the placenta; 3) high-throughput tissue microarray protein expression profiling of the placenta; 4) neural network analysis to select best combinations of candidate biomarkers to predict blood pressure and birth weight; 5) linear discriminant analysis model to provide sensitivity and specificity measures for preeclampsia prediction and 6) 2D-DIGE proteomics of maternal sera in early-pregnancy.

Whole-genome transcriptomics study of 17 placentas identified placenta- and pregnancy-specific genes differentially expressed in the placenta in preeclampsia and/or HELLP syndrome. The products of this set of genes can be identified in the maternal serum in large amounts in pregnancy, and thus, their expression and differential regulation is pregnancy-specific. However, their changes may not only be specific for preeclampsia, but also for other obstetrical syndromes.

High-throughput qRT-PCR expressional profiling of 100 placentas validated selected putative preeclampsia biomarkers at the RNA level.

High-throughput tissue microarray protein expression profiling of 100 placentas validated selected putative preeclampsia biomarkers at the protein level.

Neural network analysis supported the selection of the best combinations of putative preeclampsia biomarker genes, which expression can predict blood pressure and birth weight.

The Linear Discriminant Analysis showed that the average sensitivity and specificity of transcriptomic biomarkers for the detection of preeclampsia was 91.5% and 75%, respectively.

2D-DIGE proteomics of maternal sera in early-pregnancy revealed that the proteome of first trimester maternal blood in women with early-onset or late-onset preeclampsia differs from that of normal pregnant women, and these differences are partially different in the two subtypes of preeclampsia. Although these inflammatory and/or metabolic markers are not specific for pregnancy, they can differentiate between the two subtypes of preeclampsia. The combination of these transcriptomic and proteomic biomarker candidates resulted in a panel of molecules, which can detect preeclampsia-specific changes in maternal blood, and can also differentiate between the different subtypes of preeclampsia.

A number of methods for obtaining expression data can be used singly or in combination for determining expression patterns and profiles in the context of the present disclosure. For example, DNA and RNA expression patterns can be evaluated by northern analysis, PCR, RT-PCR, quantitative real-time RT-PCR analysis with TaqMan assays, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening.

Gene expression changes can be related to epigenetic variations (e.g. DNA methylation). Epigenetic regulation mechanisms do not involve a change to the DNA sequence. Instead, epigenetic variations include covalent modification of DNA, RNA, and the proteins associated with DNA. These in turn can result in changes to the conformation of DNA and accessibility of regulators to the DNA. Such changes cannot be identified simply by gene sequencing. Janssen, B. G. et al., Particle and Fibre Toxicology, 10:22 (2013) studied methylation in placental tissue using methods published by Tabish, A. M. et al., *PLoS ONE* 2012, 7:e34674 and by Godderis, L. et al., Epigenomics 4:269-277 (2012). MS-MLPA (Methylation-specific Multiplex ligation-dependent probe amplification) can be used to study methylation status of specific genes, for example in Proctor, M. et al., Clin. Chem. 52:1276-1283 (2006). Materials and methods for MS-MLPA as used in published studies can be obtained from MRC-Holland, Amsterdam, The Netherlands. Additional methods are reviewed and compared in Shen, L. et al., Curr. Opin. Clin. Nutr. Metab. Care. 10:576-81 (2007); Gu H et al., Nature Methods 7:133-138 (2010); Bock C et al., Nature Biotech. 28:1106-1114 (2010); Harris R A et al., Nature Biotech. 28:1097-1105 (2010).

Protein expression patterns can be evaluated using any method that provides a quantitative measure and is suitable for evaluation of multiple markers extracted from samples. Exemplary methods include: ELISA sandwich assays, mass spectrometric detection, calorimetric assays, binding to a protein array (e.g., antibody array), or fluorescent activated cell sorting (FACS). Approaches can use labeled affinity reagents (e.g., antibodies, small molecules, etc.) that recognize epitopes of one or more protein products in an ELISA, antibody array, or FACS screen.

Typically, the term high-throughput refers to a format that performs at least about 100 assays, or at least about 500 assays, or at least about 1000 assays, or at least about 5000 assays, or at least about 10,000 assays, or more per day. When enumerating assays, either the number of samples or the number of protein markers assayed can be considered. Generally high-throughput expression analysis methods involve a logical or physical array of either the subject samples, or the protein markers, or both. Appropriate array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384, or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis.

Alternatively, a variety of solid phase arrays can also be employed to determine expression patterns. Exemplary formats include membrane or filter arrays (e.g., nitrocellulose, nylon), pin arrays, and bead arrays (e.g., in a liquid "slurry").

Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In one embodiment, arrays can include "chips" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138.

Microarray expression may be detected by scanning the microarray with a variety of laser or CCD-based scanners, and extracting features with software packages, for example, Imagene (Biodiscovery, Hawthorne, Calif.), Feature Extraction Software (Agilent), Scanalyze (Eisen, M. 1999. SCANALYZE User Manual; Stanford Univ., Stanford, Calif. Ver 2.32.), or GenePix (Axon Instruments).

In one embodiment, quantitative data obtained about the markers of interest and other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained dataset with a reference dataset, a linear algorithm, a quadratic algorithm, a decision tree algorithm, or a voting algorithm. The analytic process may set a threshold for determining the probability that a sample belongs to a given class. The probability preferably is at least 50%, or at least 60%, or at least 70%, or at least 80%, or at least 90% or higher.

The following examples further illustrate the present disclosure but should not be construed as limiting its scope in any way.

EXAMPLES

Example 1

Microarray Study

The research described in this Example was approved by the Health Science Board of Hungary and the Human Investigation Committee of Wayne State University. After obtaining informed consent, placental tissue samples were collected from Caucasian women at the First Department of Obstetrics and Gynecology, Semmelweis University. Specimens and data were stored anonymously. Pregnancies were dated to be between 8-12 weeks of gestation according to ultrasound scans. Patients with multiple pregnancies (twins, triplets, etc.) or fetuses having congenital or chromosomal abnormalities were excluded. Women were enrolled in the following homogenous groups: (1) preterm severe preeclampsia, with or without HELLP syndrome (n=12) and (2) preterm controls (n=5) (Table 1). Preeclampsia was defined according to the criteria set by the American College of Obstetricians and Gynecologists (Blood pressure: 140 mm Hg or higher systolic or 90 mm Hg or higher diastolic after 20 weeks of gestation in a woman with previously normal blood pressure; proteinuria: 0.3 g or more of protein in a 24-hour urine collection (usually corresponds with 1+ or greater on a urine dipstick test). Severe preeclampsia was defined according to Sibai et al., [Sibai, B et al. Preeclampsia. Lancet 2005; 365:785-99]. Preterm controls had no medical complications, clinical or histological signs of chorioamnionitis, and delivered neonates with a birth weight appropriate-for-gestational age (AGA). C-section was performed in all preeclampsia cases due to severe symptoms, as well as in all controls due to previous C-section or malpresentation before 37 weeks of gestation.

TABLE 1

| Groups | Preterm control (n = 5) | Preterm preeclampsia with/without HELLP syndrome (n = 12) |
|---|---|---|
| Maternal age (y)[b] | 31.6 (31.5-34.3) | 30.3 (26.1-35) |
| Primiparity[a] | 40 | 66.7 |
| Gestational age (week)[b] | 31.0 (30.9-34.0) | 31.2 (29.3-33.2) |
| Race[a] | | |
| Caucasian | 100 | 100 |
| African American | 0 | 0 |
| Other | 0 | 0 |
| Systolic BP (mmHg)[b] | 120 (120-120) | 163 (160-170)[c] |
| Diastolic BP (mmHg)[b] | 80 (70-80) | 100 (100-101)[c] |
| Proteinuria[a] | 0 | 100 |
| Birth weight (g)[b] | 1990 (1640-2210) | 1065 (990-1420) |
| Cesarean delivery[a] | 100 | 100 |

[a]Percentage
[b]Median (IQR)
[c]$p < 0.01$

RNA Isolation and Microarray Experiments

Placentas (n=17) were obtained immediately after delivery. Tissue specimens were excised from central cotyledons close to the umbilical cord in order to reduce the possible bias due to regional differences in gene expression, dissected from the choriodecidua on dry ice and stored at −80° C. Tissues were homogenized using a ThermoSavant FastPrep FP120 Homogenizer (Thermo Scientific, Wilmington, Del., USA) with Lysing MatrixD (MP Biomedicals, Illkirch, France). Total RNA was isolated using RNeasy Fibrous Tissue Mini Kit (Qiagen GmbH, Hilden, Germany), quantified with NanoDrop1000 (Thermo Scientific) and assessed by Agilent 2100 Bioanalyzer (Matriks A S, Oslo, Norway). Total RNAs (controls, n=5; preeclampsia, n=12) were labeled, and Cy3-RNAs were fragmented and hybridized to the Whole Human Genome Oligo Microarray G4112A on an Agilent scanner, (Agilent Technologies, Santa Clara, Calif., USA), and processed with Agilent Feature Extraction software v9.5 according to the manufacturer's guidelines.

Data Analysis

Demographics data were compared by the Fisher's exact test and Mann-Whitney test using SPSS version 12.0 (SPSS Inc., Chicago, Ill., USA). Microarray data analysis was performed using the R statistical language and environment (website r-project.org). Microarray expression intensities were background-corrected using the "minimum" method in the "backgroundCorrect" function of the "limma" package. After log 2 transformation, data were quantile-normalized. From the 41,093 probesets on the array, 93 were removed before differential expression analysis because of lacking annotation in the array definition file (Agilent Technologies). Subsequently, an expression filter was applied to retain probesets with intensity greater than log 2 in at least two samples, yielding a final matrix of 30,027 probesets (15,939 unique genes). Differential gene expression was assessed using a moderated t-test. P-values were adjusted using the false discovery rate (FDR) method. Target gene Entrez IDs for the probesets were determined using the R package "hgu4112a.db". For probesets without annotation in the package, Entrez IDs were taken from the array definition file (Agilent Technologies). Probesets remaining un-annotated (without Entrez ID and/or gene symbol) were removed from further analysis. Probesets were defined as differentially expressed (n=1409) in this example if they had a FDR of ≤0.2 and a fold-change of ≥1.5. As used herein, "differential expression", "significantly differentially expressed", and similar terms generally mean that expression of a gene is significantly different based on a statistical power analysis, the results of which can be validated by qPCR at a 95% confidence interval.

The human U133A/GNF1H microarray data on 79 human tissues, cells and cell lines from Symatlas microarray database [Su, Al et al. A gene atlas of the mouse and human protein-encoding transcriptomes. PNAS 2004; 101:6062-67] was downloaded to search for human genes with predominant placental expression. A probeset was defined as having predominant placental expression, if its placental expression was 1)≥1,000 fluorescence units; 2) six times higher than the $75^{th}$ quantile of values in 78 other tissue and cell sources; and 3) two times higher than its expression in the tissue with the second highest expression. The resulting 215 probesets corresponded to 153 unique genes. An additional eleven genes not present on the microarray platform (Affymetrix, Santa Clara, Calif., USA) used by Symatlas were added to this list based on their potential relevance. Out of 164 predominantly placental expressed genes, 157 were present on our Agilent array. These genes were tested for enrichment in differentially expressed genes compared to all genes on the array (1,409 out of 15,939) using Fisher's exact tests.

Chromosomal locations for all genes tested on the Agilent array were obtained from the R package "org.Hs.eg.db". Out of the 15,939 unique and 1,409 differentially expressed genes on the array, 15,935 and 1,408 could be assigned to chromosomes, respectively. Mapping the microarray probe sets on the Affymetrix human U133A/GNF1H chips to ENTREZ identifiers was performed using the Bioconductor hgu133a.db and hgfocus.db packages. Chromosomal locations of the resulting list of genes were obtained from the package org.Hs.eg.db and from NCBI for the eleven additional genes. Enrichment analyses for chromosomes among PPE genes, differentially expressed genes, and differentially expressed genes encoding for transcriptional regulators were tested by Fisher's exact test. Chromosomal locations of PPE genes and differentially expressed genes (transcription regulators and non-transcription regulators) were visualized by Circos (FIG. 1).

Weighted gene co-expression network analysis (WGCNA) was applied on the 1,409 differentially expressed genes across 17 samples to identify distinct regulation modules and prioritize candidate genes for qPCR verification. Gene pair-wise similarity (absolute Pearson correlation) matrix was first computed, then soft-thresholded by raising to the power of 10 (chosen based on the scalefree topology criterion) to obtain an adjacency matrix. The topology overlap matrix (TOM) was then derived from the adjacency matrix. The topology overlap measures the node interconnectedness within a network and was generalized to a weighted co-expression network. This measure defines similarity between two genes based on both correlations within themselves and outside with other genes. Gene distance matrix was defined as 1-TOM, and used for average linkage hierarchical clustering. A hybrid dynamic tree-cutting method was applied to obtain modules (tree clusters). Gene modules identified with this approach were further tested for enrichment in PPE genes using a Fisher's exact test. Transcription regulatory genes that were expressed at high levels (average log 2 intensity >9) and co-expressed (absolute Pearson coefficient >0.8) with the most genes among PPE genes were treated as candidates for hub-genes in the module.

Example 2

Validation Study

Study Groups, Clinical Definitions and Sample Collection

The research described in this Example was approved by the Institutional Review Boards of the Eunice Kennedy Shriver National Institute of Child Health and Human Development (NICHD), National Institutes of Health (NIH), Department of Health and Human Services (DHHS), and Wayne State University. After informed consent was obtained, placentas (n=100) were retrieved from the bank of biological specimen of the Perinatology Research Branch (NICHD, NIH, DHHS). Pregnancies were dated to be between 8-12 weeks according to ultrasound scans. Patients with multiple pregnancies (twins, triplets, etc.) or fetuses having congenital or chromosomal abnormalities were excluded. Specimens and data were stored anonymously.

For qRT-PCR, tissue microarray, mRNA in situ hybridization, and laser capture microdissection, placentas were used from women selected from a large cohort into the following, homogenous patient groups: (1) preterm severe preeclampsia (PE; ≤36 weeks; n=20); (2) preterm severe preeclampsia associated with small-for-gestational age (SGA) (PE-SGA; ≤36 weeks; n=20); (3) preterm controls (PTC; ≤36 weeks; n=20); (4) term severe preeclampsia (TPE; ≥37 weeks; n=10); (5) term severe preeclampsia associated with SGA (TPESGA; ≥37 weeks; n=10); and (6) term controls (TC; ≥37 weeks; n=20). Women in these groups were predominantly of African American origin (Table 2). Term controls, consisting of normal pregnant women with (n=10) or without (n=10) labor, and preterm controls with preterm labor and delivery (n=20) had no medical complications or clinical or histological signs of chorioamnionitis, and delivered AGA neonates. Labor was defined by the presence of regular uterine contractions at a frequency of at least two contractions every 10 minutes with cervical changes resulting in delivery. Preeclampsia was defined according to the criteria set by the American College of Obstetricians and Gynecologists. Severe preeclampsia was defined according to Sibai et al., see above. SGA was defined as neonatal birth-weight below the 10th percentile for gestational age. C-section was performed in all preeclampsia cases due to severe symptoms and in controls due to previous C-section or malpresentation.

3=strong. All villi in a random field of each of three cores were evaluated by both examiners, and scores within each

TABLE 2

| Groups | Preterm control (n = 20) | Preterm preeclampsia (n = 20) | Preterm preeclampsia with SGA (n = 20) | Term control (n = 20) | Term preeclampsia (n = 10) | Term preeclampsia with SGA (n = 10) |
|---|---|---|---|---|---|---|
| Maternal age (y)[b] | 22 (20-28.5) | 23.5 (21-27) | 22.5 (19.5-30) | 22 (21-32) | 19 (19-35) | 26.5 (19-31) |
| Primiparity[a] | 20 | 40 | 25 | 15 | 40 | 10 |
| Gestational age (week)[b] | 32.3 (28.2-34.9) | 31.4 (29.6-33.6) | 31.8 (29.7-34.4) | 38.6 (38-39.1) | 39.1 (38.6-39.6) | 38.4 (37.3-38.9) |
| Race[a] | | | | | | |
| Caucasian | 5 | 10 | 10 | 15 | 0 | 0 |
| African American | 95 | 90 | 90 | 80 | 100 | 100 |
| Other | 0 | 0 | 0 | 5 | 0 | 0 |
| Systolic BP (mmHg)[b] | 116 (110-125) | 177 (166-187)[c] | 171 (164-189)[c] | 121 (111-134) | 173 (165-178)[c] | 169 (164-190)[c] |
| Diastolic BP (mmHg)[b] | 65 (59-71) | 105 (103-111)[c] | 108 (94-118)[c] | 70 (64-73) | 106 (102-110)[c] | 102 (97-104)[c] |
| Proteinuria[b] | 0 | 3 (2-3)[c] | 3 (3-3)[c] | 0 | 3 (1-3)[c] | 3 (1-3)[c] |
| Birth weight (g)[b] | 1635 (1075-2715) | 1488 (1050-1908) | 1173 (908-1650) | 3215 (3110-3335) | 3123 (2990-3200) | 2405 (2205-2555)[c] |
| Birth weight percentile[b] | 40.5 (31.9-53.4) | 22.7 (18.3-32.9)[d] | 6.7 (1-8.6)[c] | 46 (37.2-63) | 37.1 (28.5-48.8) | 1.1 (1-3.5)[c] |
| Cesarean delivery[a] | 45 | 80[d] | 75 | 55 | 40 | 20 |

[a]Percentage;
[b]Median (IQR);
[c]p < 0.001;
[d]p < 0.05

Total RNA Isolation, cDNA Generation and Quantitative Real-Time RT-PCR

Total RNA was isolated from snap-frozen placental villous tissues (n=100) with TRIzol reagent (Invitrogen, Carlsbad, Calif., USA) and Qiagen RNeasy kit (Qiagen, Valencia, Calif., USA) according to the manufacturers' recommendations. The 28S/18S ratios and the RNA integrity numbers were assessed using an Agilent Bioanalyzer 2100 (Agilent Technologies), RNA concentrations were measured with NanoDrop1000 (Thermo Scientific). Five hundred ng of total RNA was reverse transcribed with High Capacity cDNA Reverse Transcription Kit using random hexamers (Applied Biosystems). TaqMan Assays (Applied Biosystems) were used for high-throughput gene expression profiling on the Biomark™ qRT-PCR system (Fluidigm, San Francisco, Calif., USA) according to the manufacturers' instructions.

Tissue Microarray (TMA) Construction, Immunostaining and Immunoscoring

TMAs were constructed from FFPE villous tissue blocks (n=100). Briefly, three 20×35 mm recipient blocks were made of Paraplast X-Tra tissue embedding media (Fisher Scientific, Pittsburgh, Pa., USA). One mm diameter cores from tissue blocks were transferred in triplicate into recipient paraffin blocks using an automated tissue arrayer (Beecher Instruments, Inc., Silver Spring, Md., USA). Five µm sections cut from TMAs were placed on silanized slides and stained with antibodies and reagents manually, or either on a Ventana Discovery autostainer (Ventana Medical Systems, Inc, Tucson, Ariz., USA) or a Leica BOND-MAX™ autostainer (Leica Microsystems, Wetzlar, Germany). Images were captured with an Olympus BX41 microscope (Olympus America Inc., Center Valley, Pa., USA). Immunostainings were semiquantitatively scored by two examiners blinded to the clinical information with a modified immunoreactive score. Immunostaining intensity was graded as follows: 0=negative, 1=weak, 2=intermediate, and core were averaged to represent target protein quantity of that core. Thus, each placenta had three scores corresponding to three cores examined, and group comparisons using these scores were conducted in a same way as for qRT-PCR data.

Histopathologic Evaluation of the Placenta

Placental tissue samples (n=100) were taken by systematic random sampling, fixed in 10% neutral-buffered formalin, and embedded in paraffin. Five µm sections were cut from the villous tissue blocks, stained with hematoxylin and eosin, and examined using bright-field light microscopy by two anatomic pathologists blinded to the clinical information. Histopathologic changes were defined according to published criteria. "Maternal underperfusion" and "fetal vascular thrombo-occlusive disease" scores were calculated by summing the number of different pathologic lesions consistent with these lesion categories present in a given placenta.

Statistical Analysis and Evaluation of qRT-PCR Data

Demographics data were compared by the Fisher's exact test and Mann-Whitney test using SPSS version 12.0 (SPSS). qPCR data were analyzed using the $\Delta\Delta Ct$ method in the R statistical environment (website r-project.org). Data was first normalized to the reference gene (RPLPO) and batch effect was adjusted through calibrator samples. Loge mRNA relative concentrations were obtained for each sample as $-\Delta Ct_{(gene)}=Ct_{(RPLPO)}-Ct_{(gene)}$. The surrogate gene expression values ($-\Delta Ct_{gene}$) were used to perform a hierarchical clustering with 1-Pearson correlation distance and average linkage. Between group comparisons (in which groups were predefined based on the clinical characteristics of the patients) were performed by fitting a linear model on $-\Delta Ct$ values, using as covariates the group variable indicator while allowing for an interaction between the group variable and the maturity status of the fetus (term vs. preterm).

Besides these group comparisons, the analysis was extended to include all 100 patients in the validation phase, to test for the association between gene expression and blood pressure as well as birth weight while adjusting for gestational age. All variables in the latter analysis were treated as continuous. P-values of <0.05 were considered significant.

A neural networks based approach was used to determine the best combination of 2-8 genes that would best predict blood pressure and birth weight at the same time based on qRT-PCR data. Samples (n=100) were randomly split into 10 equal and balanced (with respect to the presence of preeclampsia) cross-validation folds. At each fold, 90% of the samples were used to rank the genes in an univariate fashion for predicting blood pressure and birth weight separately, and the best 15 genes for each of the two outcomes were retained using simple linear model, adjusting for gender and maturity (term/preterm). Then all gene-combinations were used as inputs in a neural network model that was trained to predict both blood pressure and birth weight using the training data. The remaining 10% of the samples were used to determine the Average Absolute Relative prediction Error (AARE) of the neural network for each gene-combination. The cross-validation procedure was repeated 10 times, splitting therefore the data into 10 different 10-fold partitions, for a total of 100 training and 100 test sets of samples. The number of times that a given gene-combination was found in the top 5% of combinations (the smallest AARE) was recorded and used to rank the combinations of genes for their ability to predict both blood pressure and birth weight percentile. A linear discriminant analysis (LDA) model was used to provide a realistic measure of the sensitivity and specificity of a model predicting the disease status (preeclampsia vs controls). LDA was performed starting with six genes (FLT1, HSD17B1, LEP, LGALS14, PAPPA2, and PLAC1) chosen from the results of the neural network analysis as being top 2 best predictors and/or highly placenta specific genes, and then was also repeated with a restricted set of four genes (HSD17B1, LGALS14, PLAC1, and PAPPA2). The 100 samples were split repeatedly at random in two parts: a training part (80% of the samples) was used to fit a LDA model, and a test part (20% of the samples) was used to compute the sensitivity and specificity of the fitted model. The estimates for sensitivity and specificity were averaged over 100 such trials to give a robust estimate. At each trial, the genes considered were ranked using a t-test and the optimal number of them to be included in the LDA model is determined using the performance of LDA model via an internal 3-fold cross-validation process. The procedure is described in more detail elsewhere (Tarca, A. L., Than, N. G., & Romero, R. Methodological Approach from the Best Overall Team in the IMPROVER Diagnostic Signature Challenge. *Systems Biomedicine* submitted, (2013).

The model had two sets of parameters. The mean expressions values (−ΔCt values) of the four genes in the two groups were (m):

|  | HSD17B1 | LGALS14 | PLAC1 | PAPPA2 |
|---|---|---|---|---|
| $m_{Ctl}$ | 0.091715 | −1.77314 | −1.81852 | −0.65007 |
| $m_{PE}$ | −1.05794 | −2.8269 | −2.69142 | 1.092378 | and the variance-covariance matrix (Σ) was:

|  | HSD17B1 | LGALS14 | PLAC1 | PAPPA2 |
|---|---|---|---|---|
| HSD17B1 | 1.677801 | 1.583045 | 1.354269 | 0.26431 |
| LGALS14 | 1.583045 | 2.082332 | 1.533739 | 0.551178 |
| PLAC1 | 1.354269 | 1.533739 | 1.654183 | 0.331429 |
| PAPPA2 | 0.26431 | 0.551178 | 0.331429 | 1.904354 |

For any new individual we assumed that the expression profile x was available, e.g.

x=

| HSD17B1 | LGALS14 | PLAC1 | PAPPA2 |
|---|---|---|---|
| −1.29723 | −2.68723 | −2.9415 | 2.099069 |

The posterior probability for each patient class (preeclampsia vs. controls) was computed from the new profile values and model parameters using the multivariate normal formula:

$$p(x \mid Ctl) = \frac{1}{(2\pi)^{N/2}|\Sigma|^{1/2}} \exp\left(-\frac{1}{2}(x - \mu_{Ctl})^T \Sigma^{-1}(x - \mu_{Ctl})\right) = 0.00149$$

$$p(x \mid PE) = \frac{1}{(2\pi)^{N/2}|\Sigma|^{1/2}} \exp\left(-\frac{1}{2}(x - \mu_{PE})^T \Sigma^{-1}(x - \mu_{PE})\right) = 0.0196$$

When p(x|PE)>p(x|Ctl), the sample was classified as preeclampsia. When p(x|Ctl)>p(x|PE), the sample was classified as control.

The statistical R package was used to compute these probabilities using the following syntax, assuming that these parameters are loaded into R first, and the mvtnorm library is also loaded:

```
> x
           HSD17B1   LGALS14    PLAC1    PAPPA2
10796     -1.297228 -2.687228 -2.941502  2.099069
> m
           HSD17B1   LGALS14    PLAC1    PAPPA2
Control   0.091715 -1.773139 -1.818516 -0.6500658
PE       -1.057936 -2.826896 -2.691423  1.0923776
> sigma
           HSD17B1   LGALS14    PLAC1    PAPPA2
HSD17B1   1.6778008 1.5830448 1.3542685  0.2643097
LGALS14   1.5830448 2.0823321 1.5337394  0.5511775
PLAC1     1.3542685 1.5337394 1.6541829  0.3314286
PAPPA2    0.2643097 0.5511775 0.3314286  1.9043535
> pCtl=dmvnorm(nx, m[1,], sigma,log = FALSE)
> pPE=dmvnorm(nx, m[2,], sigma,log = FALSE)
> pCtl
    10796
0.001489049
> pPE
    10796
0.01960817
```

Example 3

Maternal Serum Proteomics

Study Groups, Clinical Definitions and Sample Collection

All women were enrolled in a prospective, longitudinal, multicenter study in prenatal community clinics of the Maccabi Healthcare Services, Israel between August 2002 and March 2003. Pregnancies were dated according to the last menstrual period and verified by first trimester ultrasound. Patients with multiple pregnancies (twins, triplets, etc.) or fetuses having congenital or chromosomal abnormalities were excluded. The collection and investigation of human clinical samples were approved by the Maccabi Institutional Review Board, experimental procedures and data analyses were approved by the Health Science Board of Hungary and the Human Investigation Committee of Wayne State University. Informed consent was obtained from women prior to sample collection. Specimens and data were stored anonymously.

Preeclampsia was defined as hypertension that developed after 20 weeks (systolic or diastolic blood pressure ≥140 or ≥90 mmHg, respectively, measured at two different time points, 4 h to 1 week apart) coupled with proteinuria (≥300 mg in a 24 h urine collection or ≥2+ on a dipstick) according to the International Society for the Study of Hypertension in Pregnancy. Preeclampsia was defined severe, if 1) severe hypertension (systolic or diastolic blood pressure ≥160 or ≥110 mmHg) was coupled with proteinuria; 2) if hypertension was coupled with severe proteinuria (≥5 g/24 h or ≥3 on a dipstick), or 3) if maternal multi-organ involvement was present, such as pulmonary edema, oliguria, abnormal liver function, epigastric or right upper-quadrant pain, thrombocytopenia, or severe central nervous symptoms including seizures. Small—for gestational age was defined as neonatal birth weight below the 10th percentile for gestational age. Healthy controls had no medical or obstetric complications and delivered a neonate with a birth-weight appropriate for gestational age.

Peripheral blood samples were obtained by venipuncture in the first trimester from women who subsequently developed preterm severe preeclampsia (<36 weeks; n=5), term severe preeclampsia (≥37 weeks; n=5), as well as healthy controls (≥37 weeks; n=10) matched for gestational age at blood draw (Table 3). Samples were kept for 1-2 h at room temperature (RT) and then centrifuged at 10,000 g for 10 min. Sera were collected, stored at 2-8° C. for up to 48 h until transferred to the Maccabi Central Laboratory, and then stored in aliquots at −20° C. until shipped on dry ice to Hungary.

nologies, Santa Clara, Calif., USA) according to the manufacturer's protocol. To improve the resolution of 2D gels, immunodepleted serum samples were liophylized, and then delipidated and salt depleted at Proteome Services, Ltd. (Budapest, Hungary). Briefly, one volume of all samples was mixed with four volumes of methanol and was thoroughly vortexed. Subsequently, one volume of chloroform was added to these mixtures, which were vortexed again followed by the incorporation of three volumes of water (HPLC grade). After centrifugation at 14,000 rpm for 5 min at 4° C., the upper phases were discarded. Three volumes of methanol were then added and the resultant mixtures were vortexed and centrifuged again. The supernatants were discarded and the pellets containing the precipitated plasma proteins were air-dried for 10 min. The delipidated and salt-depleted plasma protein samples were dissolved in lysis buffer (7M urea; 2M thiourea; 20 mM Tris; 5 mM magnesium acetate, 4% CHAPS) and their pH was adjusted to 8.0.

Fluorescent Labeling and Two-Dimensional Differential in-Gel Electrophoresis (2D-DIGE)

Protein concentrations of the immunodepleted, desalted and delipidated serum samples were between 2-4 µg/µl as determined with PlusOne Quant Kit (GE Healthcare, Pittsburgh, Pa., USA). Samples were equalized for protein content, and then 5 µg of each protein sample was labeled with CyDye DICE Fluor Labeling kit for Scarce Samples (saturation dye) (GE Healthcare) at a concentration of 4 nmol/5 µg protein according to the manufacturer's instructions. Individual samples from cases (n=10) and controls (n=10) were labeled with Cy5. An internal standard reference sample was pooled from equal amounts (2.5 µg) of all individual samples in this experimental set and was labeled with Cy3. Then, 5 µg of each Cy5-labeled individual sample was merged with 5 µg of the Cy3-labeled reference sample, and these 20 mixtures were run in 2×10 gels simultaneously. Briefly, labeled proteins were dissolved in IEF buffer containing 0.5% ampholytes, 0.5% DTT, 8M urea, 30% glycerin, 2% CHAPS and were rehydrated passively onto 24 cm IPG 20 strips (pH3-10, GE Healthcare) for at least 14 h at RT. After rehydration, the IPG strips were subjected to first dimension IEF for 24 h to attain a total of 80 kVh. Focused proteins were reduced by equilibrating with a buffer con-

TABLE 3

| Groups | Controls for PE with SGA | Preeclampsia with SGA | Controls for term PE | Term preeclampsia |
| --- | --- | --- | --- | --- |
| Number of cases | 5 | 5 | 5 | 5 |
| Gestational age at blood draw (week) | 10 (9-11) | 8 (8-9) | 8 (8-9) | 9 (8-10) |
| Gestational age at delivery (week) | 39.7 (38.6-40.0) | 34.9 (29.3-35.3) | 38.7 (38.6-41.0) | 38.1 (38.0-38.1) |
| Systolic BP (mmHg) | 105 (104-110) | 160 (150165) | 110 (110118) | 150 (140160) |
| Diastolic BP (mmHg) | 60 (60-70) | 100 (100-100) | 67 (63-68) | 100 (90-100) |
| Proteinuria | 0 | 4 (3-4) | — | 3 (3-4) |
| Birth weight (gram) | 2955 (2900-3100) | 1720 (975-1800) | 2955 (2900-3100) | 3200 (3150-3210) |

Median (IQR)

I. Discovery Phase
Sample Preparations, Immunodepletion of High-Abundance Serum Proteins Sera were immunodepleted at Biosystems International Ltd. (Debrecen, Hungary) for 14 highly abundant serum proteins on an Agilent 1100 HPLC system using Multiple Affinity Removal LC Column-Human 14 (Agilent Techtaining 1% mercaptoethanol for 20 min. After reduction, IPG strips were loaded onto 10% polyacrylamide gels (24×20 cm) and SDS-PAGE was conducted at 10 W/gel in the second dimension. Then, gels were scanned in a Typhoon TRIO+ scanner (GE Healthcare) using appropriate lasers and filters with the PMT biased at 600V. Images in different channels were overlaid using selected colors and the differences were visualized using Image Quant software (GE Healthcare). Differential protein analysis was performed using the Differential In-gel Analysis (DIA) and Biological Variance (BVA) modules of the DeCyder 6.0 software package (GE Healthcare).

Identification of Differentially Expressed Protein Spots

The internal standard reference sample representative of every protein present in all experiments was loaded equally in all gels, and thus, provided an average image for the normalization of individual samples. The determination of the relative abundance of the fluorescent signal between internal standards across all gels provided standardization between the gels, removing experimental variations and reducing gel-to-gel variations. According to the standard proteomic protocol, the threshold for differential expression was set at 1.05-fold minimum fold-change. A p-value was determined for each protein spot using the Student's t-test by the BVA module of the DeCyder software (GE Healthcare). A p-value of <0.05 was considered statistically significant.

II. Preparative Phase

Sample Preparation, Fluorescent Labeling, 2D-DIGE

The density of spots in the case of Colloidal Coomassie Blue labeling depends only the concentration of protein in the sample, however the density of spots in the case of saturation dyes labeling depends on the number of cysteines of the labeled proteins too, because the saturation dyes labeling method labels all available cysteines on each protein. This results in the same pattern with different density among samples on the analytical and the preparative gels rendering identification more difficult. To eliminate this problem for the exact identification of proteins in spots of interest, the preparative 2D electrophoresis was performed using CyDye saturation fluorescent labeling and Colloidal Coomassie Blue labeling in the same gel. A total of 800 µg of proteins per each of the two gels ran. Briefly, the 10-10 immunodepleted serum samples in the "preterm" and "term" comparisons were pooled together and the salt-depletion step was repeated three-times. Five µg protein from each of these two pooled samples was labeled with Cy3, merged with 800 µg of unlabeled proteins from the same sample and resolved in the dry-strip. After separation of the first dimension, focused proteins were first reduced by equilibrating with a buffer containing 1% mercaptoethanol for 20 min, and then alkylated with a buffer containing 2.5% iodoacetamide for 20 min. Following electrophoresis, gels were scanned in a Typhoon TRIO+ scanner as described above, the differentially expressed spots were matched among the "master" analytical and the fluorescent preparative gel image using Biological Variance (BVA) modules of the DeCyder 6.0 software package (GE Healthcare). The resolved protein spots were visualized by the Colloidal Coomassie Blue G-250 staining protocol. Differentially expressed individual spots were excised from the gels to compare the images.

III. Identification Phase

In-Gel Digestion

The excised protein spots were analyzed at the Proteomics Research Group of the Biological Research Center of the Hungarian Academy of Sciences (Szeged, Hungary); the detailed protocol is entitled "In-Gel Digest Procedure" described in the website "msfacility.ucsf.edu/ingel.html" and reproduced below: Briefly, salts, SDS and Coomassie brilliant blue were washed out, disulfide bridges were reduced with dithiothreitol, and then free sulfhydryls were alkylated with iodoacetamide. Digestion with side-chain protected porcine trypsin (Promega) proceeded at 37° C. for 4 h, and the resulting peptides were extracted.

In-Gel Digest Procedure

1. Wearing gloves and sleeve protectors, wipe down ALL surfaces in the hood with methanol/water moistened lint-free cloth, including the outside of all your tubes (make sure to not wipe off the labeling!), the outside and inside of the Speed Vac and centrifuge, tube racks, bottles etc. Wipe razor blades with methanol-soaked lint-free cloth.
2. Prepare the following solutions:
   25 mM $NH_4HCO_3$ (100 mg/50 ml)
   25 mM $NH_4HCO_3$ in 50% ACN
   50% ACN/5% formic acid (may substitute TFA or acetic acid)
   12.5 ng/µL trypsin in 25 mM $NH_4HCO_3$ (freshly diluted)
3. Dice each gel slice into small pieces (1 mm2) and place into 0.65 mL siliconized tubes (PGC Scientific).
4. Add ~100 µL (or enough to cover) of 25 mM $NH_4HCO_3$/50% ACN and vortex for 10 min.
5. Using gel loading pipet tip, extract the supernatant and discard.
6. Repeat steps 3 and 4 once or twice.
7. Speed Vac the gel pieces to complete dryness (~20 min).
   For low-level proteins (<1 pmol), especially those separated by 1-D SDS-PAGE, reduction and alkylation is recommended. These procedures are performed after step 6.
   a. Prepare fresh solutions:
      10 mM DTT in 25 mM $NH_4HCO_3$ (1.5 mg/mL)
      55 mM iodoacetamide in 25 mM $NH_4HCO_3$ (10 mg/mL)
   b. Add 25 µL (or enough to cover) 10 mM DTT in 25 mM $NH_4HCO_3$ to dried gels. Vortex and spin briefly. Allow reaction to proceed at 56° C. for 1 hr.
   c. Remove supernatant, add 25 µl 55 mM iodoacetamide to the gel pieces. Vortex and spin briefly. Allow reaction to proceed in the dark for 45 min. at room temperature.
   d. Remove supernatant (discard). Wash gels with ~100 µl $NH_4HCO_3$, vortex 10 min, spin.
   e. Remove supernatant (discard). Dehydrate gels with ~100 µL (or enough to cover) of 25 mM $NH_4HCO_3$ in 50% ACN, vortex 5 min, spin. Repeat one time.
   f. Speed Vac the gel pieces to complete dryness (~20 min). Proceed with trypsin digest.
8. Add trypsin solution to just barely cover the gel pieces. Estimate the gel volume and add about 3× volume of trypsin solution. This volume will vary from sample to sample, but on average ~5-25 µL is sufficient.
9. Rehydrate the gel pieces on ice or at 4° C. for 10 min. Spin. Add 25 mM $NH_4HCO_3$ as needed to cover the gel pieces.
10. Spin briefly and incubate at 37° C. for 4 hours—overnight.

Extraction of Peptides

1. Transfer the digest solution (aqueous extraction) into a clean 0.65 mL siliconized tube.
2. To the gel pieces, add 30 µL (enough to cover) of 50% ACN/5% formic acid, vortex 20-30 min., spin, sonicate 5 min. Repeat.
3. Vortex the extracted digests, spin and Speed Vac to reduce volume to 10 µL.
4. Either proceed with C18 ZipTip (Millipore) cleanup or analyze with LC-MS. Add 2-5 µL of 5% formic acid.

When analyzing low levels of protein, concentrate the peptides by eluting from ZipTips using 3 μL of elution solution, into a clean 0.65 mL siliconized tube.

5. Use 1 μL of the unseparated digests for analysis by MALDI.

Matrices for Unseparated Digests:
α-cyano-4-hydroxycinammic acid in 50% ACN/1% TFA (10 mg/mL).
2,5-dihydroxybenzoic acid (DHB), saturated solution in water.

REFERENCES

Rosenfeld, et al., Anal. Biochem. (1992) 203(1), 173-179.
Hellman, et al., Anal. Biochem. (1995) 224(1), 451-455.

LC-MS/MS

Samples were analyzed on a Waters Acquity nanoUPLC system online coupled to an ion trap tandem mass spectrometer (LCQ Fleet, ThermoScientific) in information-dependent acquisition mode, where MS acquisitions (1 s survey scans) were followed by CID analyses (3 s MS/MS scans) on computer-selected multiply charged ions. HPLC conditions included in-line trapping onto a nanoACQUITY UPLC trapping column (Symmetry, C18 5 μm, 180 μm×20 mm) (15 μl/min with 3% solvent B) followed by a linear gradient of solvent B (10 to 50% in 40 min, flow rate: 250 nl/min; nanoACQUITY UPLC BEH C18 Column, 1.7 μm, 75 μm×200 mm). Solvent A: 0.1% formic acid in water, solvent B: 0.1% formic acid in acetonitrile. LC-MS/MS analysis was performed in "triple play" mode in the mass range of m/z: 450-1600.

Database Search and Data Interpretation

Raw data files were converted into searchable peak list Mascot generic files (*.mgf) with the Mascot Distiller software v2.1.1.0. (Matrix Science, Inc, London, UK). The resulting peak lists were searched against a human subdatabase of the non-redundant protein database of the National Center for Biotechnology Information (NCBInr Jul. 18, 2008, Bethesda, Md., USA; 6,833,826 sequences) in MS/MS ion search mode on an in-house Mascot server v2.2.04 using Mascot Daemon software v2.2.2. (Matrix Science Inc). Monoisotopic masses with peptide mass tolerance of ±50 ppm and fragment mass tolerance of ±0.1 Da were submitted. Carbamidomethylation of Cys was set as fixed modification, and acetylation of protein N-termini, methionine oxidation, and pyroglutamic acid formation from peptide N-terminal Gln residues were permitted as variable modifications. Acceptance criteria was set to at least two significant (peptide score>40, p<0.05) individual peptides per protein.

Results

I. Differentially Expressed Genes in Preeclampsia are Enriched Among Predominantly Placental Expressed Genes and on Three Chromosomes Because the pathogenesis of preeclampsia originates from the placenta, new biomarker candidates predominantly expressed in the placenta as well as gene-regulatory networks involved in the placental pathogenesis of preeclampsia with a systems biological approach were sought. Analysis of a microarray dataset revealed 1,409 differentially expressed unique genes in preterm preeclampsia compared to preterm controls. From these differentially expressed genes, 137 were found to encode for proteins with functions in transcription regulation (transcription factors, co-activators, or co-repressors). Analysis of BioGPS microarray data and previous evidence revealed 164 unique genes predominantly expressed in the placenta, from which 157 were present on our microarray platform.

Differentially expressed genes in preeclampsia were highly enriched (OR=3.4, p=6.9×10$^{-9}$) in PPE genes (38 out of 157) when compared to all genes on the array. When investigating chromosomal locations of genes of interest, it was found that differentially expressed genes were enriched in genes located on Chromosomes 6 and 7 (OR=1.54, pFDR=1.6×10$^{-3}$, and OR=1.42, pFDR=0.02, respectively). Interestingly, Chromosome 19 was over-represented in differentially expressed transcription regulatory genes (OR=2.6, pFDR=0.02), and genes with predominant placental expression (OR=2.5, p=1×10$^{-4}$). These enrichments are in accordance with the fact that Chromosome 19 harbors large primate and placenta-specific gene families (e.g. CGBs, LGALSs, PSGs) and zinc finger transcription factor gene families. Visualization of gene expression and co-expression data supports a potential regulatory "hub" role for Chromosome 19 in placental gene expression in primates and its dysregulation in preeclampsia.

FIG. 1. Genomic map of differentially expressed genes in preeclampsia. Circos visualization shows Chromosomes with solid lines in the inner circle. Curved lines connect the genomic coordinates of genes and transcription regulatory genes that are significantly correlated. Significance was determined by fitting a linear model between the expression level of gene and transcription regulatory gene pairs in all samples while controlling for FDR at 5%. Curves represent positive and negative correlations. The second circle shows the genomic location of PPE genes (black lines: non differentially expressed; grey lines: up- or down-regulated). The third and fourth circles show the locations of differentially expressed transcription regulatory genes and non-regulatory genes, respectively with inward-oriented bars (down-regulated) and outward oriented bars (up-regulated). The height of the bars in the third and fourth circles represents the magnitude of gene expression changes.

Figure 2A:
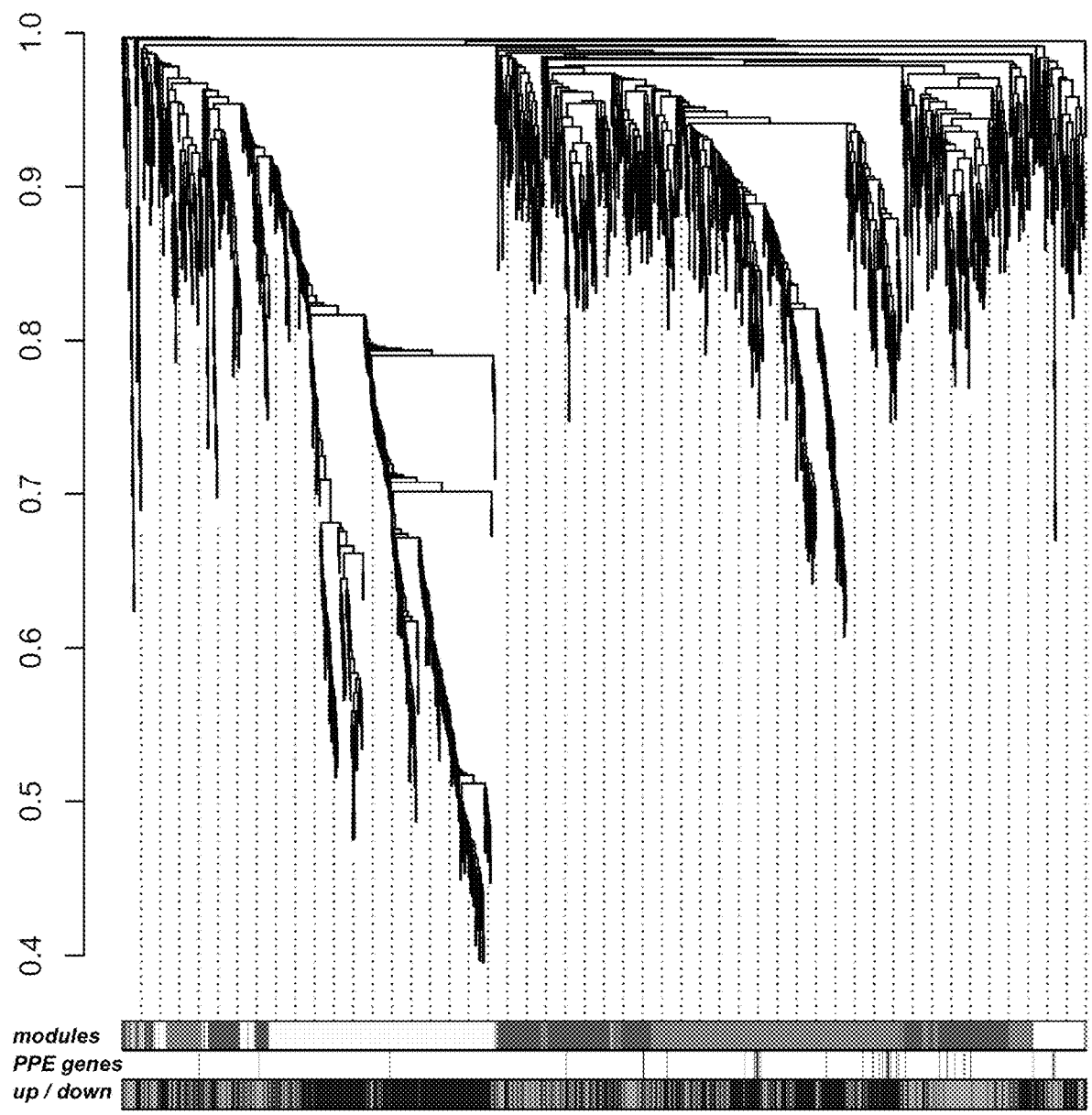
FIG. 2A-2C shows that two gene modules in preeclampsia are enriched in PPE genes and are associated with mean arterial blood pressure and birth weight percentile. 2A) Gene modules identified from WGCNA analysis of microarray data. Dysregulated placental gene expression could be characterized by five gene modules within the 1,409 differentially expressed genes in preeclampsia, marked with different shades of grey. The height plotted on the y-axis represents the distance metric (1-TOM) used by WGCNA. Out of 38 PPE genes (black vertical lines), 33 belonged to the grey-scale modules (lighter grey; n=22 and darker grey; n=11). These two modules were also enriched in up-regulated and down-regulated genes marked under the modules with grey or black lines, respectively. 2B) Hierarchical clustering of qRT-PCR data obtained with 100 samples and selected 47 genes. Genes from light and dark grey modules clustered together in the validation sample-set. Importantly, 34 out of 60 samples from women with preeclampsia clustered tightly together. Pearson correlation was used for distance, and average for linkage. Samples (column leafs) were shaded according to patient groups and maturity status. 2C) Association of gene expression with mean arterial blood pressure and birth weight percentile. For each gene, a linear model was fitted (expression-blood pressure+birth weight percentile+gender+maturity status). The significance p-values ($-\log_{10}$ of) for the two coefficients (blood pressure and birth weight percentile) were plotted for all 47 genes. Genes were shaded according to module membership (except black color for those not differentially expressed on the microarray). Filled circles represent PPE genes, dashed lines the significance threshold at p=0.05. Note that 7 out of 9 genes related to birth weight percentile are from the light grey module, while 10 out of 15 genes related to blood pressure are from the dark grey module.

FIG. 2. Two gene modules in preeclampsia are enriched in PPE genes and are associated with mean arterial blood pressure and birth weight percentile. 2A) Gene modules identified from WGCNA analysis of microarray data. Dysregulated placental gene expression could be characterized by five gene modules within the 1,409 differentially expressed genes in preeclampsia, marked with different shades of grey. The height plotted on the y-axis represents the distance metric (1-TOM) used by WGCNA. Out of 38 PPE genes (black vertical lines), 33 belonged to the grey-scale modules (lighter grey; n=22 and darker grey; n=11). These two modules were also enriched in up-regulated and down-regulated genes marked under the modules with grey or black lines, respectively). 2B) Hierarchical clustering of qRT-PCR data obtained with 100 samples and selected 47 genes. Genes from light and dark grey modules clustered together in the validation sample-set. Importantly, 34 out of 60 samples from women with preeclampsia clustered tightly together. Pearson correlation was used for distance, and average for linkage. Samples (column leafs) were shaded according to patient groups and maturity status. 2C) Association of gene expression with mean arterial blood pressure and birth weight percentile. For each gene, a linear model was fitted (expression~blood pressure+birth weight percentile+gender+maturity status). The significance p-values ($-\log_{10}$ of) for the two coefficients (blood pressure and birth weight percentile) were plotted for all 47 genes. Genes were shaded according to module membership (except black color for those not differentially expressed on the microarray). Filled circles represent PPE genes, dashed lines the significance threshold at p=0.05. Note that 7 out of 9 genes related to birth weight percentile are from the light grey module, while 10 out of 15 genes related to blood pressure are from the dark grey module.

II. Differentially Expressed Genes in Preeclampsia Cluster into Major Regulatory Modules In order to identify regulatory modules of genes and transcription regulatory genes, which may drive dysregulated placental gene expression, a WGCNA analysis with the differentially expressed genes on the microarray was conducted. Out of 1,409, 1,403 genes were assigned to four modules containing 506, 442, 381, and 74 genes. Of interest, 33 out of 38 genes with predominant placental expression belonged to the light grey (n=22) and dark grey (n=11) modules. The light grey module was enriched in down-regulated (OR=1.88, p=$2.59 \times 10^{-8}$), while the dark grey module was enriched in up-regulated (OR=6.47, p<$2.2 \times 10^{-16}$) genes, suggesting the presence of distinct dysregulated gene-networks in preterm preeclampsia.

Among up-regulated genes in the dark grey module was FLT1, which has a pathogenic role in preeclampsia by producing increased amounts of soluble Flt-1 and driving blood pressure elevation. Up-regulated genes with predominant placental expression included CRH, LEP, PAPPA2, SIGLEC6 and novel biomarker candidates. Among down-regulated, PPE genes in the light grey module were regulators of fetal growth (CSH1, HSD11B2), metabolism (ES-RRG), estrogen synthesis (HSD17B1), stress hormone metabolism (HSD11B2) and immune regulation of placentation (LGALS14).

III. Differentially Expressed Genes in the Dark Grey and Light Grey Modules are Associated with Blood Pressure and Birth-Weight Percentile, Respectively To validate the described results on a large patient population with different ethnic origin and with various subtypes of preeclampsia (preterm and term, with or without SGA), 47 genes for high-throughput expression profiling were selected, if they were: 1) differentially expressed on the microarray, predominantly placental expressed, specifically by the syncytiotrophoblast, and potentially secreted; 2) transcription regulatory genes with high co-expression with PPE genes; and 3) other genes with relevant role in trophoblast differentiation (e.g. GCM1), trophoblast-specific gene expression (e.g. TEAD3) or pathogenesis of preeclampsia (e.g. ENG, LGALS13).

Figure 2B:
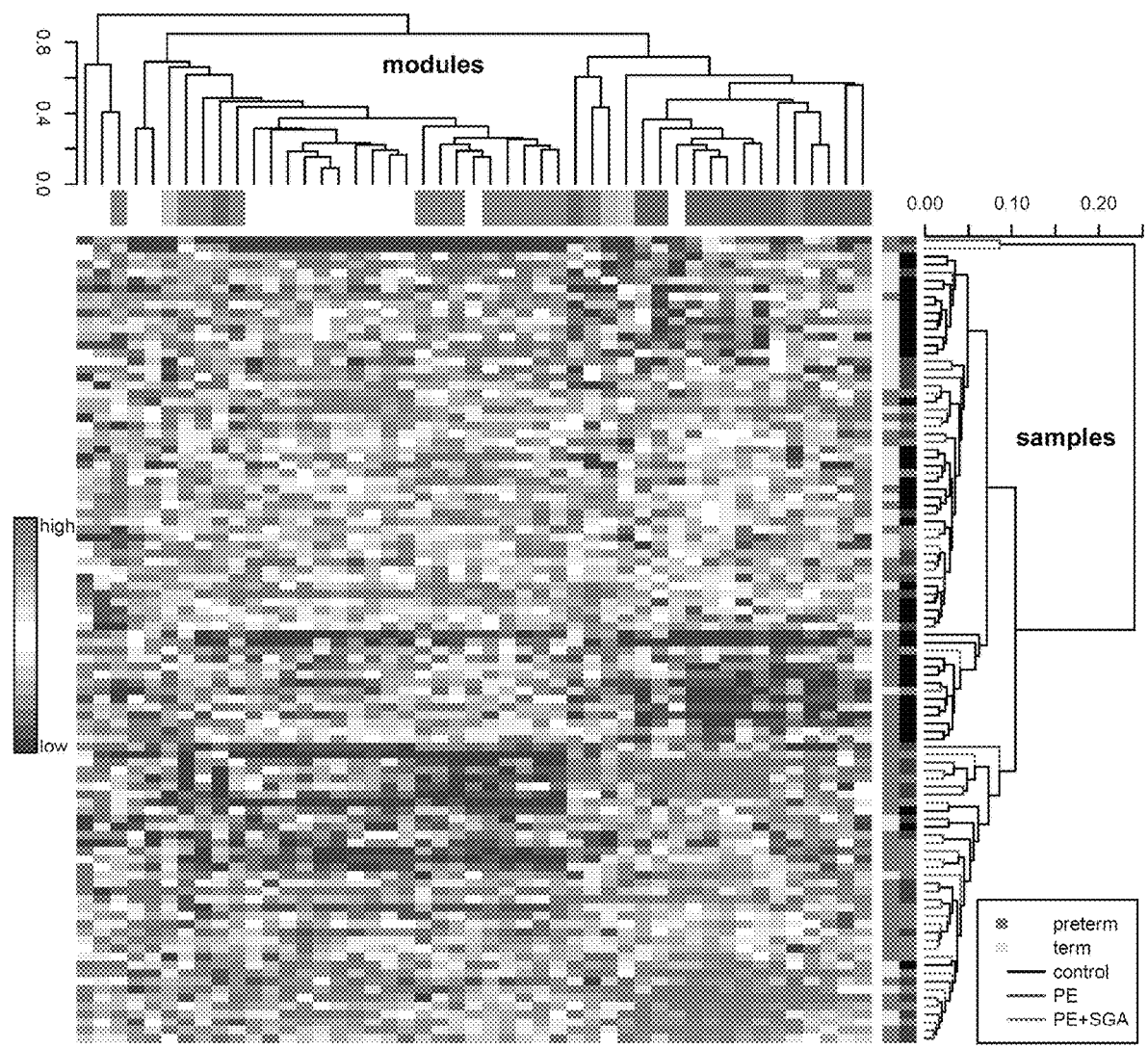
Figure 2C:
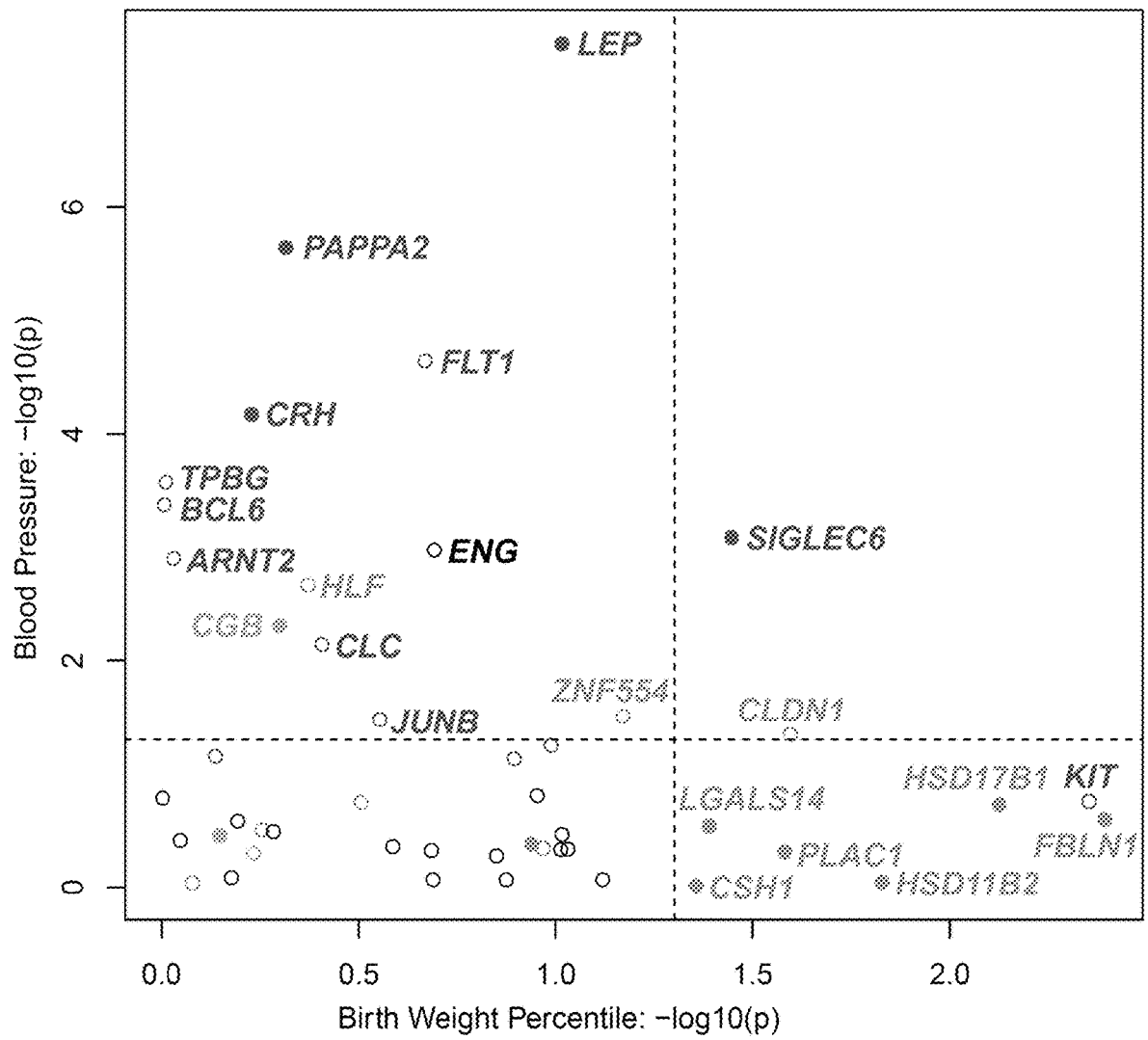

Hierarchical clustering of qRT-PCR data showed that 34 out of 60 placentas from women with preeclampsia clustered together. This was also true for the genes belonging to the light and dark grey modules (FIG. 2B). Based on the possible involvement of these modules in distinct pathogenic pathways, revealing their biological relevance in a novel way was attempted. "Phenotype analysis" showed that 7 out of 9 genes related to birth weight percentile were from the light grey module, while 10 out of 15 genes related to blood pressure were from the dark grey module (FIG. 2C).

Placental histopathologic data was also assessed. It was found that the expression of genes in the dark grey module was significantly associated with the presence of "fetal vascular thrombo-occlusive disease" (SIGLEC6, ENG, TPBG) and "maternal underperfusion" (top associations: LEP, FLT1, TPBG, ENG), conditions consistent with placental hypoxia and/or ischaemia. The majority of the light grey module genes (top associations: CLDN1, HSD17B1, CSH1, PLAC1, LGALS14) was significantly associated with the presence of "maternal underperfusion".

In addition, using a classical approach, group comparisons between controls and two groups of preeclampsia at term and preterm separately were performed. It was found that qRT-PCR data validated microarray results in 72% (34/47 genes). Tissue microarray immunostainings for four selected proteins validated the microarray data at the protein level for this module.

Figure 3:
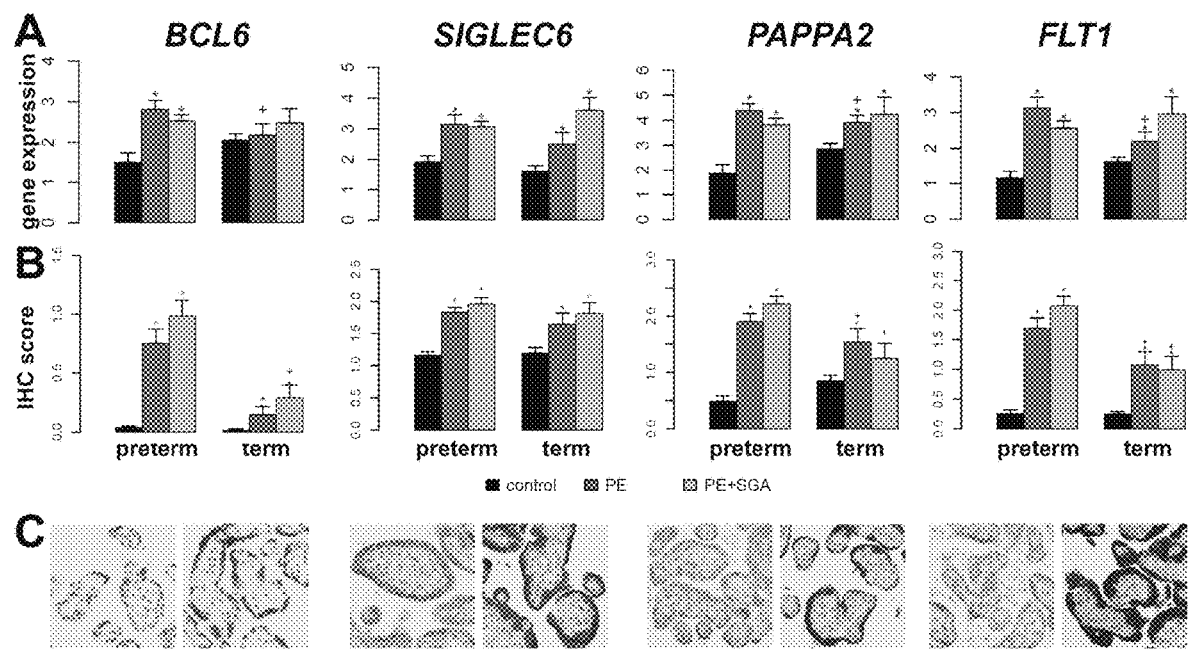
FIG. 3.

FIG. 3. The expression of dark grey module genes changes in the same direction in preeclampsia subgroups. 3A-B) In each barplot, the left and right panels show significant differences ("*") in preterm and term preeclampsia samples, respectively. Gene expression 3A) and protein immunostainings 3B) show similar patterns in sub-groups of preeclampsia. When the change with preeclampsia in the preterm samples was significantly different than the change with preeclampsia in the term samples, a "+" sign indicates this interaction. Semiquantitative immunoscorings for four proteins 3B) validated gene expression data. 3C) Representative images from the four immunostainings. The same placenta from a preterm control (left, 29 weeks) and from a patient with preterm preeclampsia with SGA (right, 31 weeks) is shown for the four immunostainings (40× magnifications).

In the light grey module, gene expression changes were also more severe in the preterm groups of preeclampsia than in term. Some genes had significant dysregulation both at term and preterm (e.g. LGALS13, LGALS14), while others only at preterm (e.g. CSH1). These data also reflect to the heterogeneous placental pathology behind the pathogenesis of preeclampsia, and the more severe pathologies in preterm.

Figure 4A:
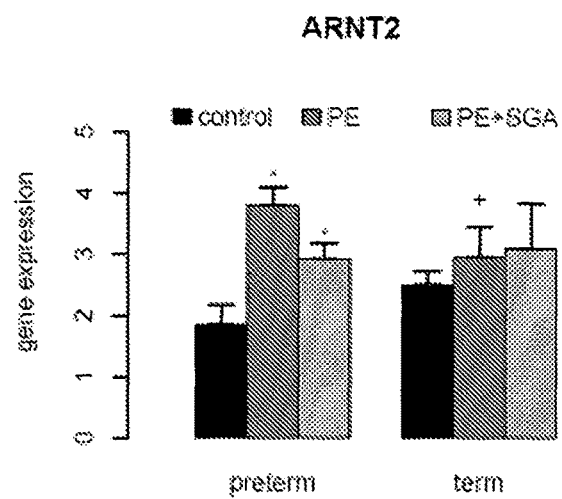
FIG. 4A-4UU show gene comparisons for ARNT2; BCL3; BCL6; BTG2; CDKN1A; CGB3; CLC; CLDN1; CRH; CSH1; CYP19A1; DUSP1; ENG; ERVFRDE1; ERVWE1; ESRRG; FBLN1; FLT1; GATA2; GCM1; GH2; HLF; HSD11B2; HSD17B1; IKBKB; INSL4; JUNB; KIT; LEP; LGALS13; LGALS14; LGALS16.
Figure 4B:
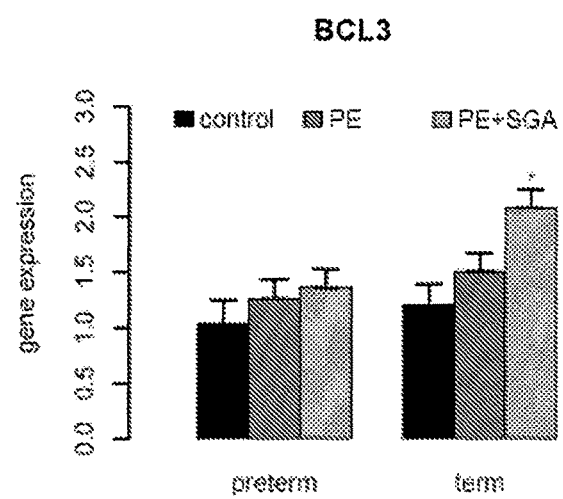
FIG. 4.
Figure 4C:
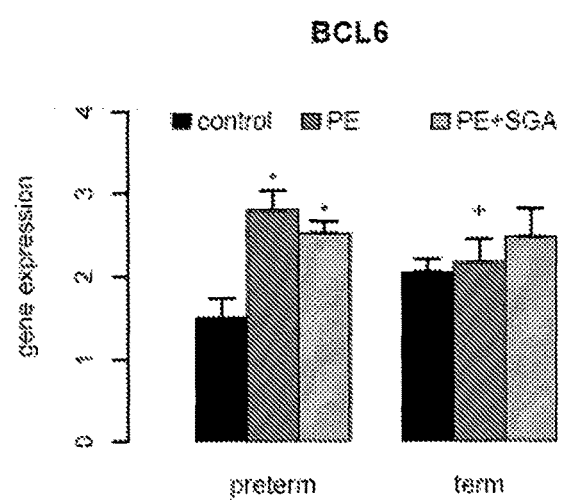
Figure 4D:
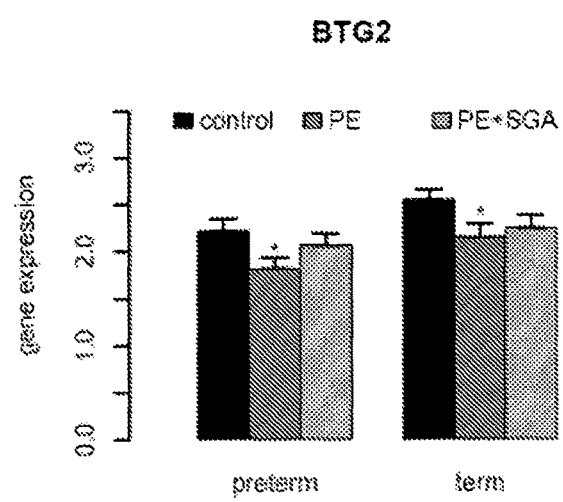
Figure 4E:
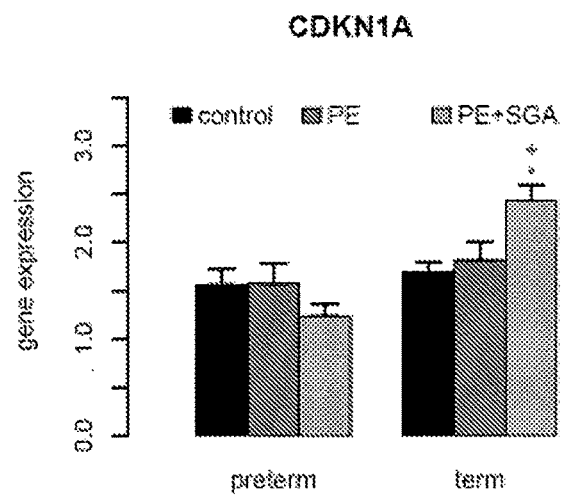
Figure 4F:
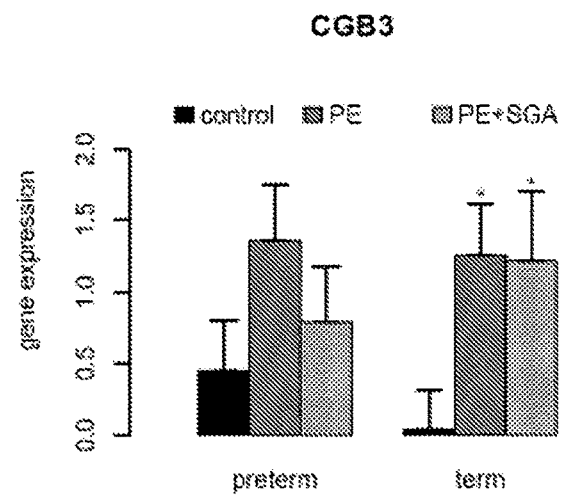
Figure 4G:
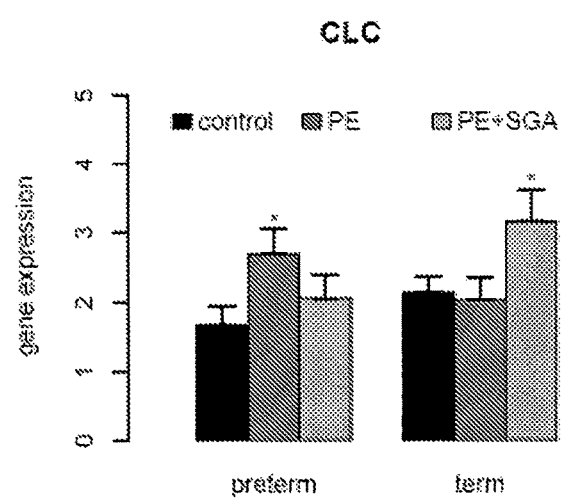
Figure 4H:
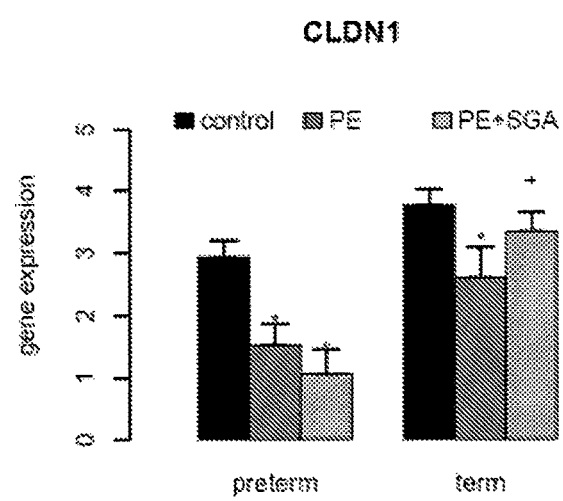
Figure 4I:
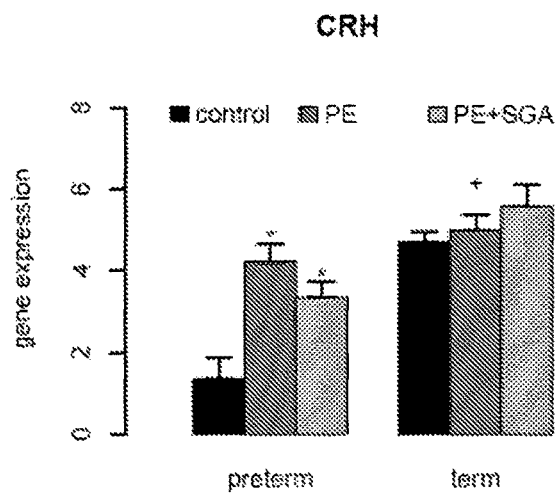
Figure 4J:
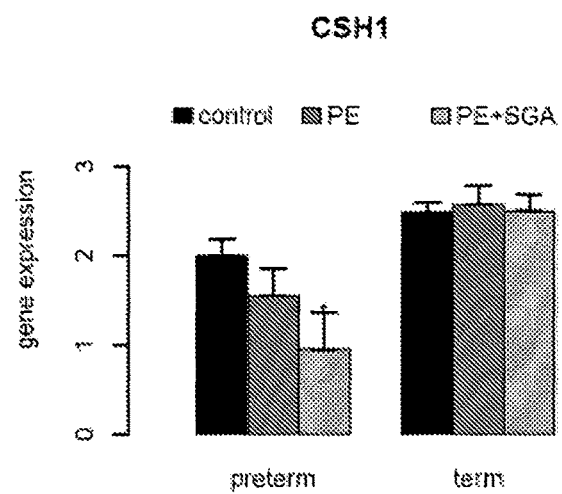
Figure 4K:
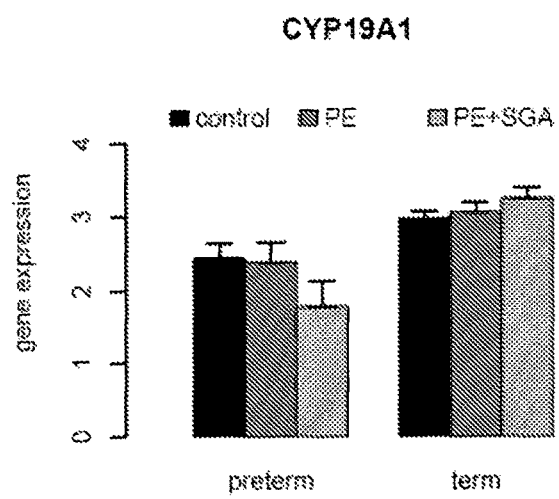
Figure 4L:
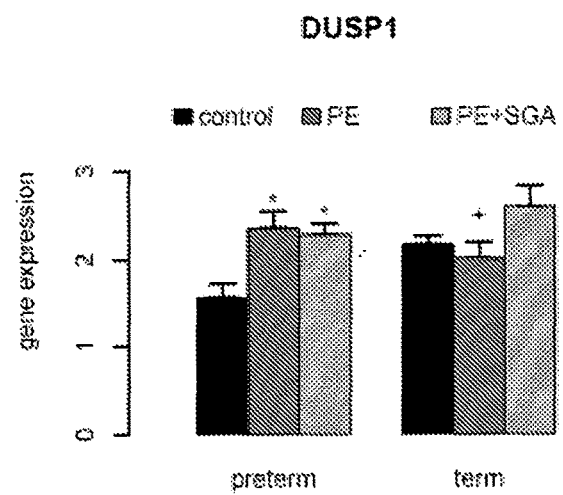
Figure 4M:
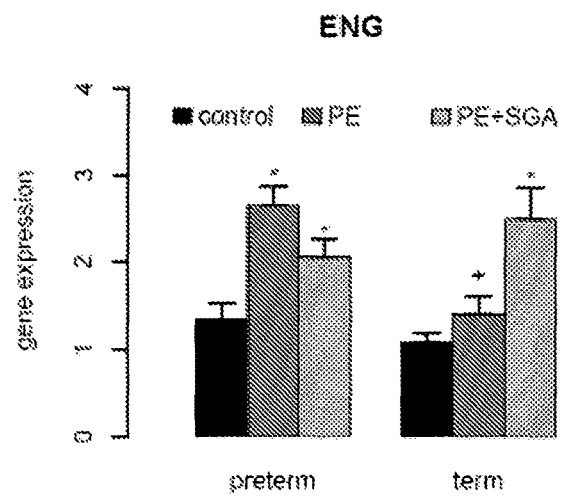
Figure 4N:
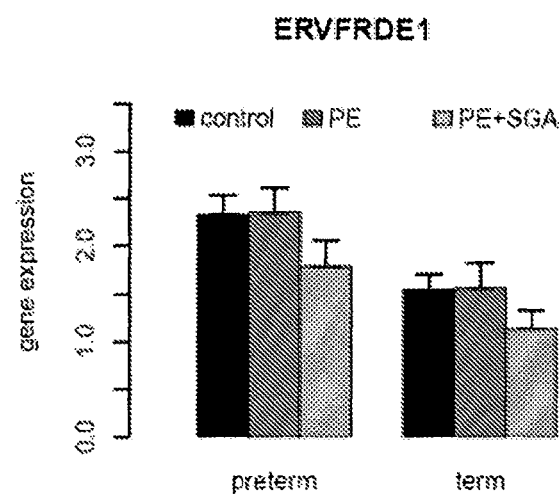
Figure 4O:
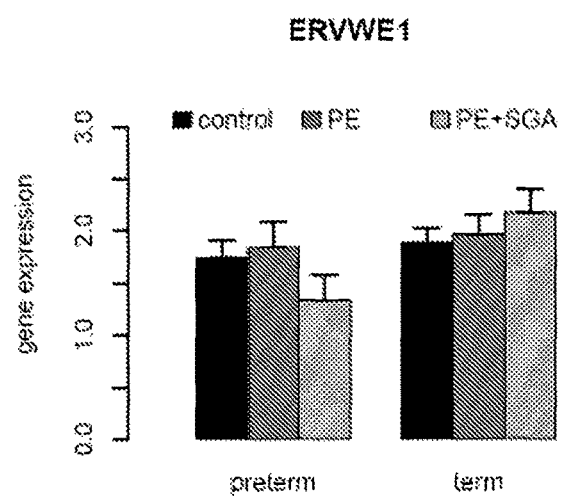
Figure 4P:
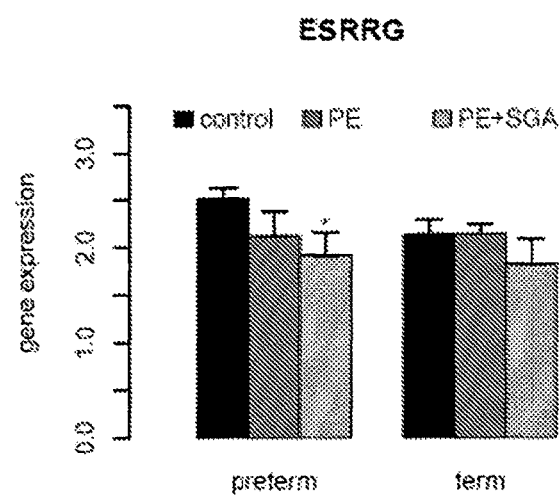
Figure 4Q:
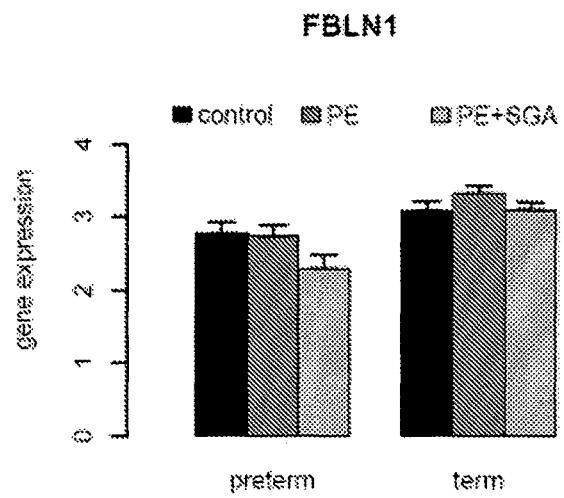
Figure 4R:
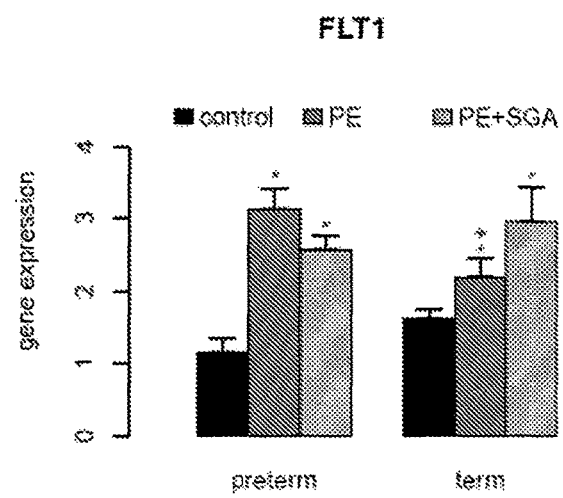
Figure 4S:
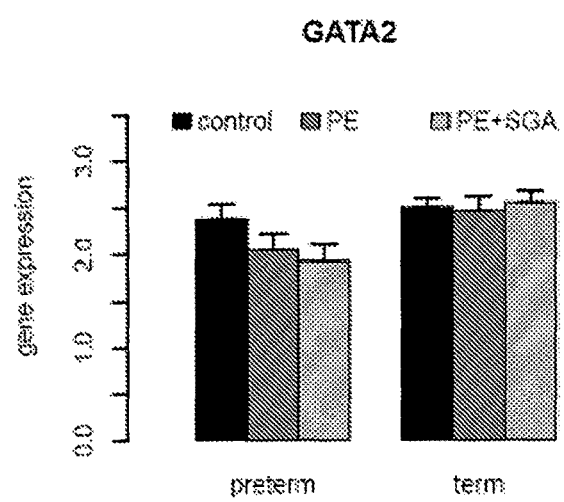
Figure 4T:
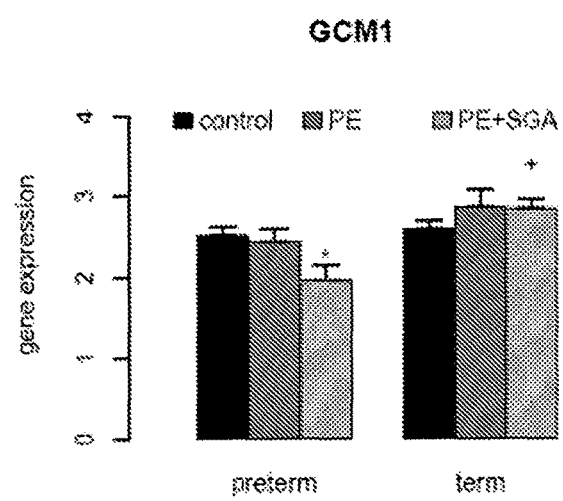
Figure 4U:
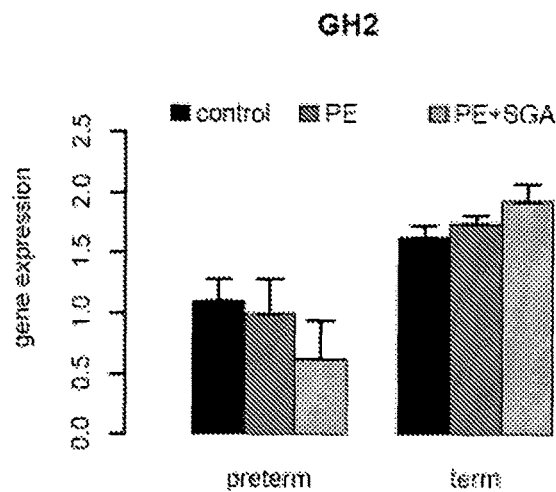
Figure 4V:
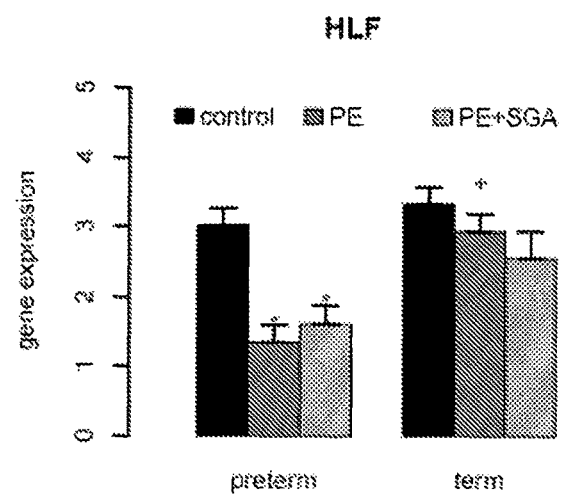
Figure 4W:
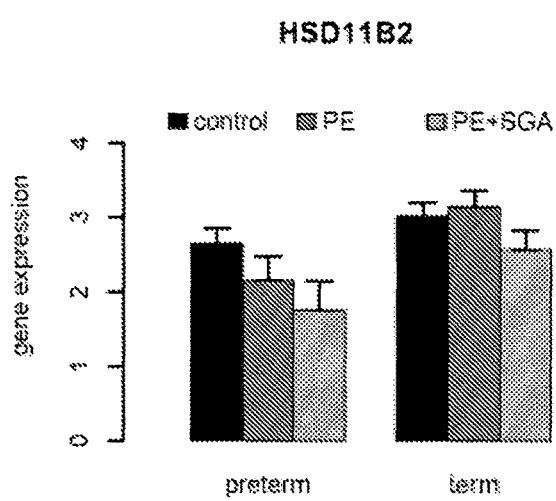
Figure 4X:
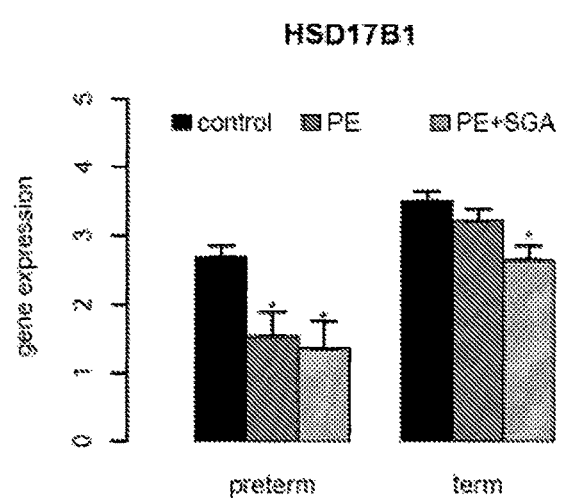
Figure 4Y:
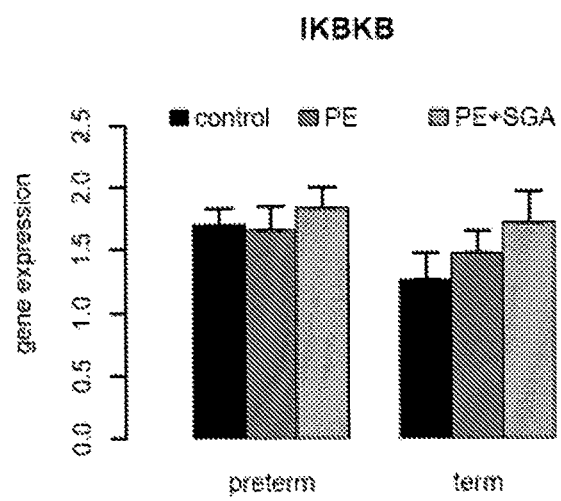
Figure 4Z:
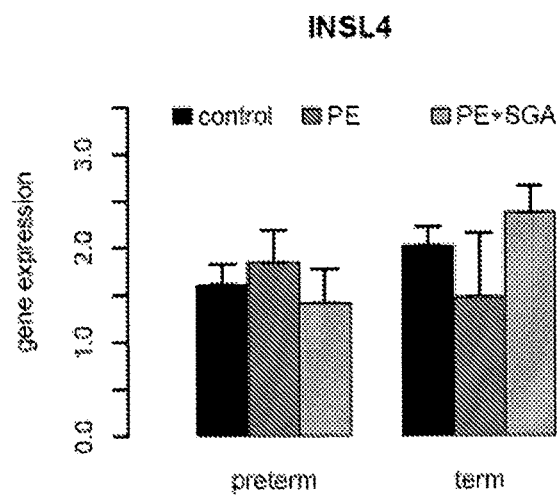
Figure 4A:
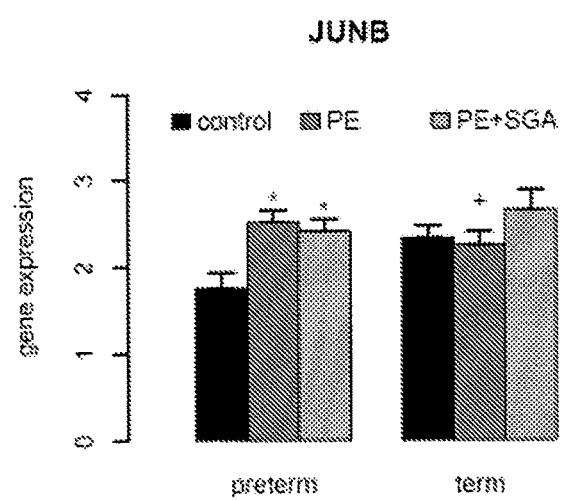
Figure 4B:
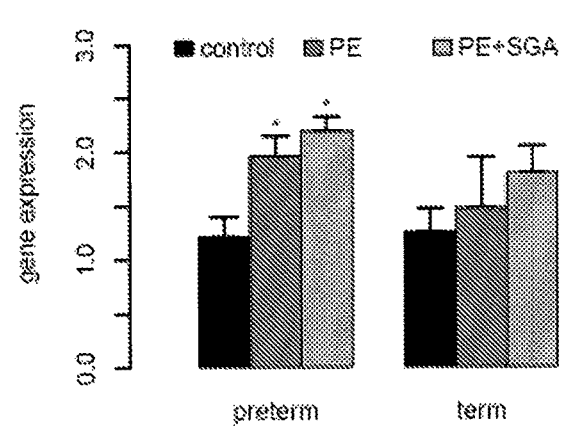
Figure 4C:
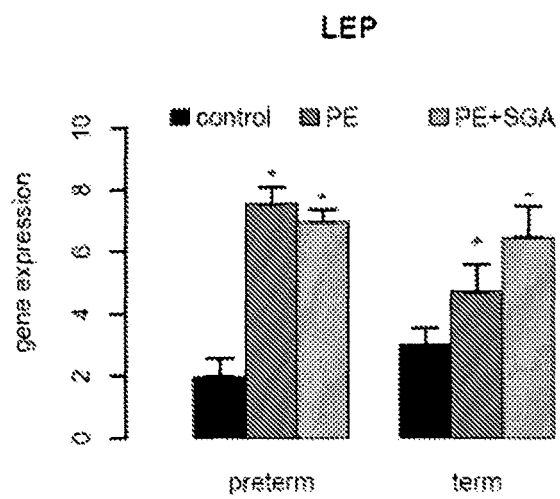
Figure 4D:
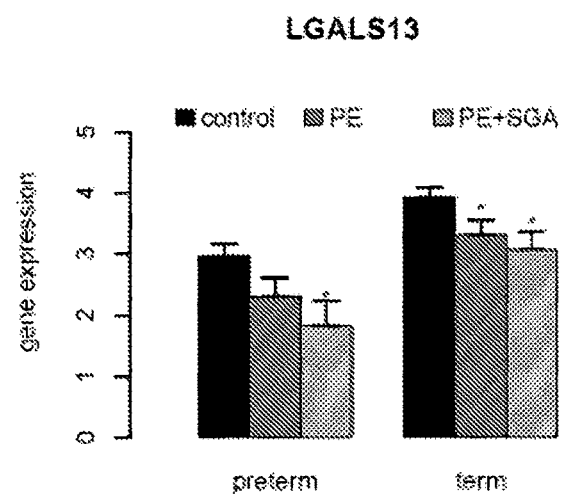
Figure 4E:
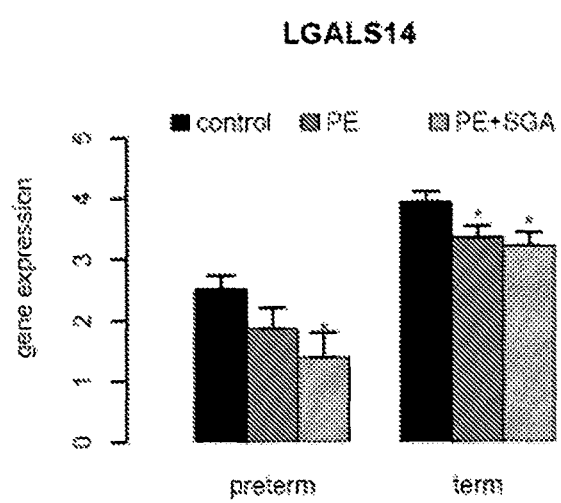
Figure 4F:
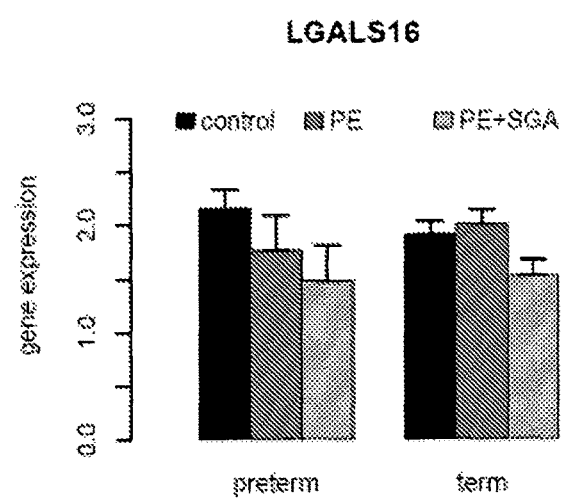
Figure 4G:
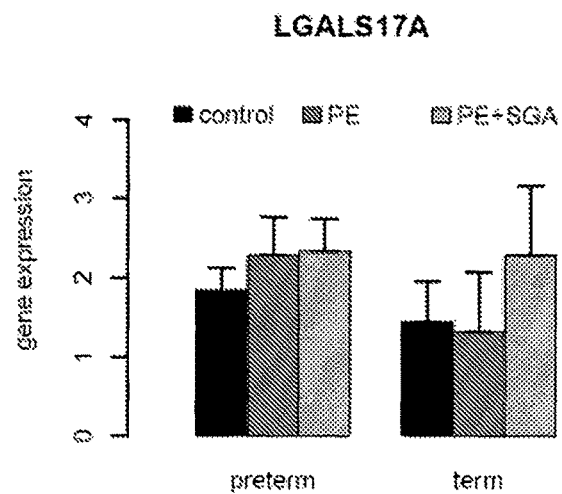
Figure 4H:
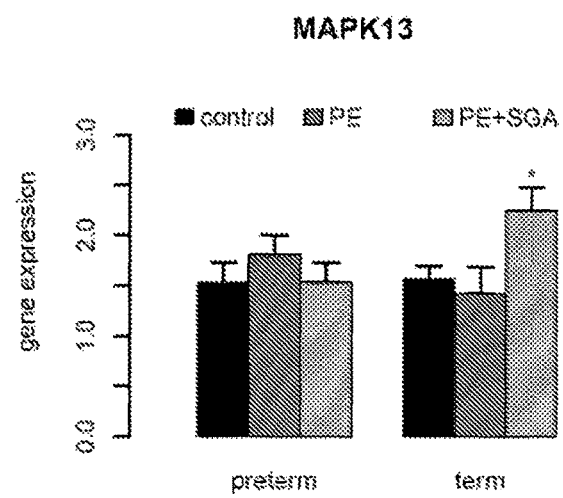
Figure 4I:
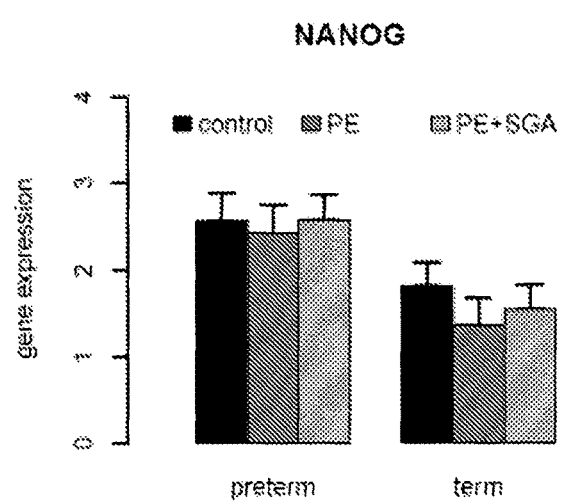
Figure 4J:
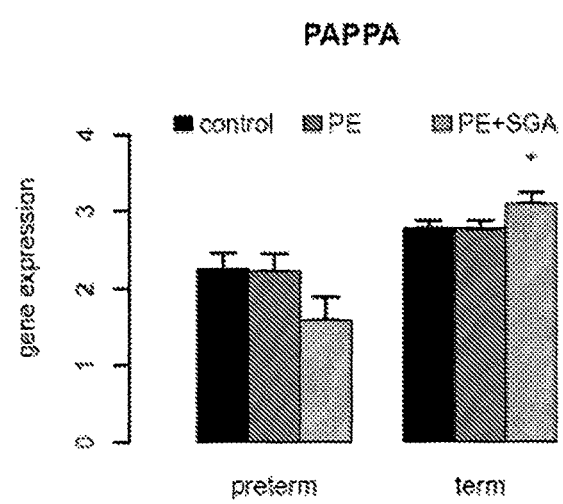
Figure 4K:
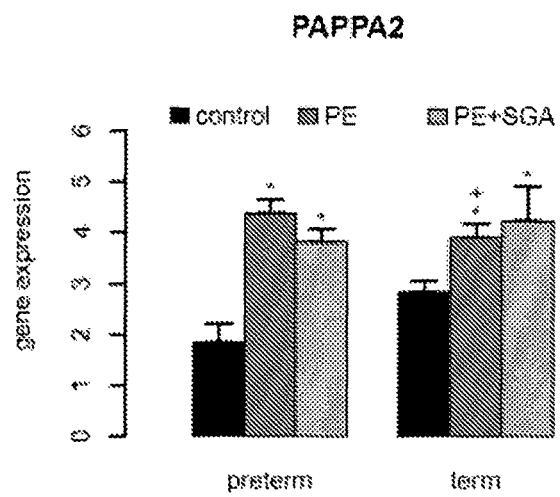
Figure 4L:
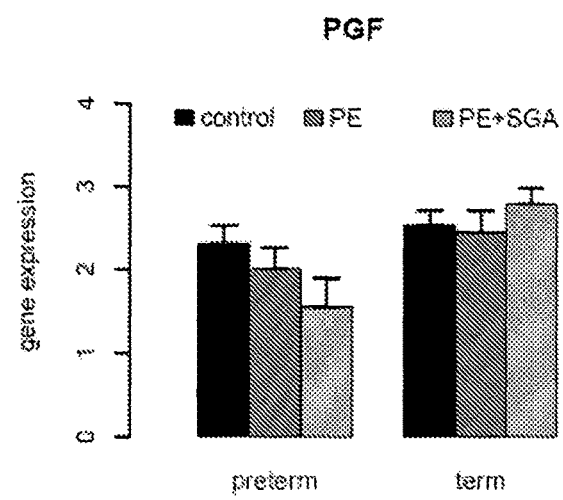
Figure 4M:
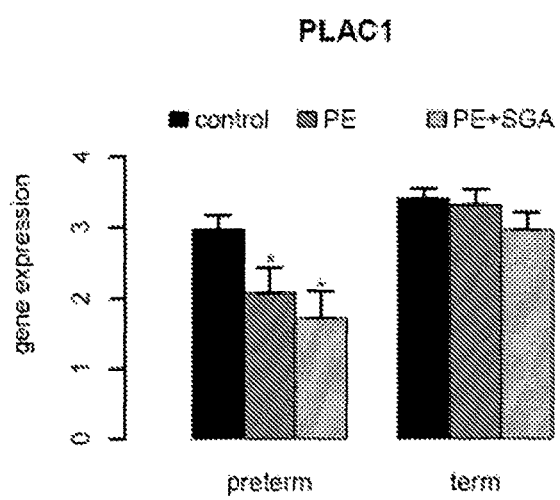
Figure 4N:
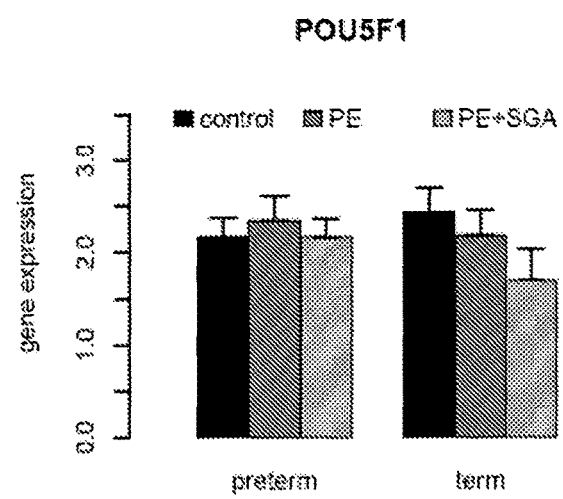

FIG. 4A-UU show gene comparisons for ARNT2; BCL3; BCL6; BTG2; CDKN1A; CGB3; CLC; CLDN1; CRH; CSH1; CYP19A1; DUSP1; ENG; ERVFRDE1; ERVWE1; ESRRG; FBLN1; FLT1; GATA2; GCM1; GH2; HLF; HSD11B2; HSD17B1; IKBKB; INSL4; JUNB; KIT; LEP; LGALS13; LGALS14; LGALS16; LGALS17A; MAPK13; NANOG; PAPPA; PAPPA2; PGF; PLAC1; POU5F1; SIGLEC6; TEAD3; TFAM; TFAP2A; TPBG; VDR; and ZNF554 respectively.

IV. Transcriptomic Biomarkers

The results of the neural network based analysis was a set of combinations of 2 to 8 genes, as assessed by the number of times they were retained as best predictors of blood pressure and birth-weight percentile when using different subsets of the training samples (Table 4). From these sets of combinations, six genes (FLT1, HSD17B1, LEP, LGALS14, PAPPA2, and PLAC1) were selected as being top 2 best predictors and/or highly placenta specific genes.

TABLE 4

| Best 2 predictors | X times out of 100 training-test sessions in top 5% |
|---|---|
| HSD17B1/PAPPA2 | 52 |
| HSD17B1/LEP | 35 |

TABLE 4-continued

| | X times out of 100 training-test sessions in top 5% |
|---|---|
| LEP/LGALS13 | 32 |
| LGALS14/PAPPA2 | 30 |
| LEP/LGALS14 | 26 |
| FLT1/HSD17B1 | 25 |
| ENG/LGALS13 | 23 |
| CRH/LGALS14 | 21 |
| CSH1/PAPPA2 | 21 |
| FLT1/LGALS14 | 19 |
| Best 3 predictors | |
| | |
| HSD17B1/KIT/PAPPA2 | 38 |
| CRH/HSD17B1/PAPPA2 | 35 |
| CSH1/HSD17B1/PAPPA2 | 35 |
| HSD17B1/LGALS13/PAPPA2 | 35 |
| CLC/HSD17B1/PAPPA2 | 33 |
| CLDN1/HSD17B1/PAPPA2 | 33 |
| FBLN1/HSD17B1/PAPPA2 | 33 |
| CGB3/HSD17B1/PAPPA2 | 32 |
| HSD17B1/PAPPA2/PLAC1 | 31 |
| CSH1/LEP/SIGLEC6 | 30 |
| Best 4 predictors | |
| | |
| FBLN1/HSD17B1/LEP/SIGLEC6 | 34 |
| CRH/HSD11B2/HSD17B1/LGALS14 | 33 |
| CLC/HSD17B1/KIT/PAPPA2 | 31 |
| CLC/HSD17B1/LGALS13/PAPPA2 | 31 |
| CRH/HSD17B1/LGALS14/PAPPA2 | 29 |
| HSD17B1/LEP/LGALS13/PAPPA2 | 28 |
| CRH/LGALS14/PAPPA2/TPBG | 26 |
| CLC/CRH/LGALS14/PAPPA2 | 25 |
| CRH/HSD17B1/KIT/PAPPA2 | 25 |
| CRH/HSD17B1/LEP/LGALS14 | 25 |
| Best 5 predictors | |
| | |
| HSD17B1/LEP/LGALS13/PAPPA2/SIGLEC6 | 32 |
| CRH/HSD11B2/HSD17B1/LGALS14/PAPPA2 | 31 |
| CLC/CRH/KIT/LGALS14/PAPPA2 | 30 |
| CSH1/FLT1/HSD17B1/LEP/SIGLEC6 | 29 |
| HSD11B2/HSD17B1/LEP/LGALS13/SIGLEC6 | 29 |
| CRH/CSH1/ENG/LGALS14/PAPPA2 | 28 |
| CRH/CSH1/LGALS14/PAPPA2/TPBG | 28 |
| CRH/HSD11B2/HSD17B1/LGALS13/TPBG | 28 |
| FBLN1/LEP/LGALS14/PAPPA2/SIGLEC6 | 28 |
| FLT1/HSD11B2/LEP/LGALS13/SIGLEC6 | 28 |
| Best 6 predictors | |
| | |
| CRH/HSD11B2/HSD17B1/LGALS13/LGALS14/TPBG | 37 |
| CRH/CSH1/HSD11B2/HSD17B1/LGALS14/PAPPA2 | 33 |
| CLC/CRH/CSH1/KIT/LGALS14/PAPPA2 | 31 |
| HSD11B2/KIT/LEP/LGALS14/SIGLEC6/TPBG | 30 |
| CRH/CSH1/HSD11B2/LGALS14/PAPPA2/TPBG | 29 |
| CSH1/FBLN1/HSD17B1/LEP/PAPPA2/SIGLEC6 | 29 |
| CLC/CRH/CSH1/FBLN1/LGALS14/PAPPA2 | 28 |
| CRH/CSH1/HSD11B2/HSD17B1/LGALS14/SIGLEC6 | 28 |
| CRH/HSD11B2/HSD17B1/KIT/LGALS14/PAPPA2 | 28 |
| ENG/FBLN1/HSD17B1/LEP/PAPPA2/SIGLEC6 | 28 |
| Best 7 predictors | |
| | |
| CRH/HSD11B2/HSD17B1/LGALS13/LGALS14/PAPPA2/TPBG | 40 |
| CRH/CSH1/HSD11B2/HSD17B1/LGALS13/LGALS14/PAPPA2 | 36 |
| CRH/HSD11B2/HSD17B1/KIT/LGALS13/LGALS14/TPBG | 34 |
| CGB3/CRH/HSD11B2/HSD17B1/LGALS13/LGALS14/TPBG | 31 |
| CRH/CSH1/FLT1/HSD11B2/HSD17B1/LGALS14/PAPPA2 | 31 |
| CLC/CRH/CSH1/FBLN1/LGALS14/PAPPA2/PLAC1 | 30 |
| CRH/CSH1/HSD11B2/HSD17B1/LGALS14/PAPPA2/PLAC1 | 30 |
| CRH/CSH1/HSD11B2/LGALS13/LGALS14/PAPPA2/TPBG | 30 |
| CRH/CSH1/LGALS13/LGALS14/PAPPA2/PLAC1/TPBG | 30 |
| CRH/CSH1/ENG/HSD11B2/HSD17B1/LGALS14/PAPPA2 | 29 |
| Best 8 predictors | |
| | |
| CRH/CSH1/HSD11B2/HSD17B1/LGALS13/LGALS14/PAPPA2/TPBG | 47 |
| CRH/CSH1/FLT1/HSD11B2/HSD17B1/LGALS13/LGALS14/TPBG | 37 |
| CGB3/CRH/HSD11B2/HSD17B1/LGALS13/LGALS14/PAPPA2/TPBG | 34 |
| CLC/CRH/HSD11B2/HSD17B1/KIT/LGALS13/LGALS14/TPBG | 33 |
| CRH/FLT1/HSD11B2/HSD17B1/LGALS13/LGALS14/PAPPA2/TPBG | 33 |
| CLC/CRH/CSH1/FBLN1/FLT1/KIT/LGALS14/PAPPA2 | 32 |

TABLE 4-continued

|  | X times out of 100 training-test sessions in top 5% |
|---|---|
| CRH/CSH1/HSD11B2/HSD17B1/LGALS13/LGALS14/SIGLEC6/TPBG | 32 |
| CRH/CSH1/FBLN1/HSD11B2/HSD17B1/LGALS13/LGALS14/TPBG | 31 |
| CRH/CSH1/FLT1/HSD11B2/HSD17B1/LGALS13/LGALS14/PAPPA2 | 31 |
| CLC/CLDN1/CRH/FBLN1/HSD11B2/HSD17B1/KIT/LGALS14 | 30 |

The Linear Discriminant Analysis showed that the average sensitivity and specificity of the selected set of transcriptomic biomarkers for the detection of preeclampsia was 91.5% and 75%, respectively.

V. Differentially Expressed Proteins in Maternal Serum in Preeclampsia

In the discovery phase, in the comparison of samples taken from healthy pregnant women with normal pregnancy outcome and those who subsequently developed preterm severe preeclampsia, 2080-2460 protein spots were identified on the gels. There were 39 protein spots, which were differentially expressed (29 down-regulated and 10 up-regulated) in at least 3 out of the 5 disease samples. The biggest difference in disease samples was 3.1-fold up-regulation and 3.1-fold down-regulation.

In the comparison of samples taken from healthy pregnant women with normal pregnancy outcome and those who subsequently developed term severe preeclampsia, 2130-2380 protein spots were identified on the gels. There were 20 protein spots, which were differentially expressed (11 down-regulated and 9 up-regulated) in at least 3 out of the 5 disease samples. The biggest difference in disease samples was a 3.9-fold up-regulation and a 4.5-fold down-regulation.

In the preparative phase, in the comparison of samples taken from healthy pregnant women with normal pregnancy outcome and those who subsequently developed preterm severe preeclampsia, there were ~2380 protein spots identified on the gels. From the 39 previously identified differentially expressed spots in preterm preeclampsia, 29 (25 down-regulated and 4 up-regulated) was identified and excised from the gels.

In the comparison of samples taken from healthy pregnant women with normal pregnancy outcome and those who subsequently developed term severe preeclampsia, there were ~2350 protein spots identified on the gels. From the 20 previously identified differentially expressed spots, 18 (11 down-regulated and 7 up-regulated) was identified and excised from the gels.

In the identification phase, the following differentially expressed proteins could be identified:

A) Preterm preeclampsia

| No | Direction | Gene symbol | ID | Protein Name |
|---|---|---|---|---|
| 1 | DOWNinPE | A1BG | gi\|21071030 | alpha 1B-glycoprotein precursor |
| 2 | DOWNinPE | AGT | gi\|532198 | Angiotensinogen |
| 3 | DOWNinPE | APOA4 | gi\|178757 | apolipoprotein A-IV precursor |
| 4 | DOWNinPE | APOL1 | gi\|12408013 | apolipoprotein L-I |
| 5 | DOWNinPE | CP | gi\|4557485 | ceruloplasmin precursor |
| 6 | DOWNinPE | C1QB | gi\|399140 | complement C1q subcomponent subunit B precursor |
| 7 | DOWNinPE | C7 | gi\|45580688 | complement component 7 precursor |
| 8 | DOWNinPE | C4 | gi\|2347136 | complement component C4 |
| 9 | DOWNinPE | CFB | gi\|291922 | complement factor B |
| 10 | DOWNinPE | CFH | gi\|148745112 | complement factor H |
| 11 | DOWNinPE | GSN | gi\|4504165 | gelsolin isoform a precursor |
| 12 | DOWNinPE | HPX | gi\|386789 | hemopexin precursor |
| 13 | DOWNinPE | HRG | gi\|4504489 | histidine-rich glycoprotein precursor |
| 14 | DOWNinPE | IGFALS | gi\|4826772 | insulin-like growth factor binding protein, acid labile subunit |
| 15 | DOWNinPE | KNG1 | gi\|37748641 | kininogen 1 |
| 16 | DOWNinPE | PLG | gi\|387026 | Plasminogen |
| 17 | DOWNinPE | PAEP | gi\|182093 | pregnancy-associated endometrial alpha2-globulin |
| 18 | DOWNinPE | GC | gi\|139641 | vitamin D-binding protein precursor |
| 19 | UPinPE | APOH | gi\|153266841 | apolipoprotein H precursor |
| 20 | UPinPE | C4 | gi\|2347136 | complement component C4 |

B) Term preeclampsia

| No | Direction | Gene symbol | ID | Protein Name |
|---|---|---|---|---|
| 1 | DOWNinPE | SERPINA3 | gi\|177809 | alpha-1-antichymotrypsin |
| 2 | DOWNinPE | CP | gi\|4557485 | ceruloplasmin precursor |
| 3 | DOWNinPE | C7 | gi\|45580688 | complement component 7 precursor |
| 4 | DOWNinPE | CFB | gi\|291922 | complement factor B |
| 5 | DOWNinPE | GSN | gi\|4504165 | gelsolin isoform a precursor |
| 6 | DOWNinPE | HRNR | gi\|28557150 | hornerin |
| 7 | DOWNinPE | ITIH2 | gi\|55958063 | inter-alpha (globulin) inhibitor H2 |
| 8 | UPinPE | AGT | gi\|532198 | angiotensinogen |
| 9 | UPinPE | CFB | gi\|291922 | complement factor B |
| 10 | UPinPE | FETUB | gi\|49902016 | fetuin B (alpha-2 Heremans-Schmid glycoprotein) |

| B) Term preeclampsia | | | |
|---|---|---|---|
| No Direction | Gene symbol | ID | Protein Name |
| 11 UPinPE | GSN | gi|4504165 | gelsolin isoform a precursor |
| 12 UPinPE | ITIH4 | gi|31542984 | inter-alpha (globulin) inhibitor H4 |
| 13 UPinPE | CD14 | gi|3983127 | monocyte antigen CD14 precursor |
| 14 UPinPE | PEDF | gi|189778 | pigment epithelial-differentiating factor |
| 15 UPinPE | PLG | gi|387026 | plasminogen |
| 16 UPinPE | GC | gi|139641 | vitamin D-binding protein precursor |

In each two comparisons, those candidates were selected which were differentially expressed in all disease specimens, had the highest fold-change, and the strongest p-value: complement factor B, gelsolin isoform a precursor, hornerin, fetuin B, hemopexin precursor, and apolipoprotein H precursor.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually, or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety. In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method for treating preeclampsia or HELLP syndrome, said method comprising:
   administering an effective amount of an agent which prevents or reduces symptoms of preeclampsia or HELLP syndrome in a female and/or fetus subject, said administering taking place before said symptoms manifest in the female and/or fetus, wherein the subject has been identified by a method comprising:
   obtaining a biological sample from a pregnant human female before the 15$^{th}$ week of pregnancy;
   determining levels of three or more biomarkers in the biological sample in a panel, wherein the panel comprises apolipoprotein H precursor and at least two other biomarkers selected from the group consisting of complement factor B, gelsolin isoform a precursor, hornerin, fetuin B, hemopexin precursor, fms-related tyrosine kinase 1, hydroxysteroid (17-β) dehydrogenase 1, leptin, lectin galactoside-binding soluble 14, pappalysin 2, and placenta-specific 1;
   generating a dataset based on the determined levels; and
   diagnosing the presence or risk of developing preeclampsia or HELLP syndrome in the subject based on a biostatistical analysis and comparison of the dataset to a reference dataset corresponding to known presence.

2. The method of claim 1 for treating preeclampsia wherein the panel comprises apolipoprotein H precursor and at least two other biomarkers selected from the group consisting of complement factor B, hornerin, hemopexin precursor, hydroxysteroid (17-β) dehydrogenase 1, lectin galactoside-binding soluble 14, and pappalysin 2; wherein the administering of the agent prevents or reduces symptoms of preeclampsia in the subject.

3. A method according to claim 1, wherein the biological sample is a blood sample.

4. A method according to claim 1, wherein the biological sample is a body fluid, secretion, or excretion sample other than blood.

5. A method according to claim 1, wherein the biological sample is an amniotic fluid sample.

6. A method according to claim 1, wherein the biological sample is fetal cells obtained invasively or non-invasively.

7. A method according to claim 1, wherein the biological sample is a placental sample.

8. A method according to claim 1, wherein the biological sample is obtained before the 14$^{th}$ week of pregnancy, before the 13$^{th}$ week of pregnancy, before the 12$^{th}$ week of pregnancy, before the 11$^{th}$ week of pregnancy, before the 10$^{th}$ week of pregnancy, before the 9$^{th}$ week of pregnancy, before the 8$^{th}$ week of pregnancy, before the 7$^{th}$ week of pregnancy, or before the 6$^{th}$ week of pregnancy.

9. The method of claim 1 wherein the levels of the three or more biomarkers are determined by a protein-based assay method.

10. The method of claim 1 wherein the levels of the three or more biomarkers are determined by using specific antibodies produced against the biomarkers whereby the biological sample is contacted with the antibodies and binding between the biomarkers and the antibodies is detected.

11. The method of claim 1 wherein the accuracy of risk assessment is more than 75%.

12. A method according to claim 1, wherein the biological sample is a cervicovaginal fluid, saliva, or urine sample.

13. A method according to claim 1, said administering taking place before the 16$^{th}$ week of pregnancy.

* * * * *

SEQUENCE LISTING

<160> NUMBER OF SEQ ID NOS: 27

<210> SEQ ID NO 1
<211> LENGTH: 495
<212> TYPE: PRT

<213> ORGANISM: Homo sapiens

<400> SEQUENCE: 1

```
Met Ser Met Leu Val Phe Leu Leu Trp Gly Val Thr Trp Gly
1               5                   10                  15

Pro Val Thr Glu Ala Ala Ile Phe Tyr Glu Thr Gln Pro Ser Leu Trp
                20                  25                  30

Ala Glu Ser Glu Ser Leu Leu Lys Pro Leu Ala Asn Val Thr Leu Thr
            35                  40                  45

Cys Gln Ala His Leu Glu Thr Pro Asp Phe Gln Leu Phe Lys Asn Gly
    50                  55                  60

Val Ala Gln Glu Pro Val His Leu Asp Ser Pro Ala Ile Lys His Gln
65                  70                  75                  80

Phe Leu Leu Thr Gly Asp Thr Gln Gly Arg Tyr Arg Cys Arg Ser Gly
                85                  90                  95

Leu Ser Thr Gly Trp Thr Gln Leu Ser Lys Leu Leu Glu Leu Thr Gly
                100                 105                 110

Pro Lys Ser Leu Pro Ala Pro Trp Leu Ser Met Ala Pro Val Ser Trp
            115                 120                 125

Ile Thr Pro Gly Leu Lys Thr Thr Ala Val Cys Arg Gly Val Leu Arg
130                 135                 140

Gly Val Thr Phe Leu Leu Arg Arg Glu Gly Asp His Glu Phe Leu Glu
145                 150                 155                 160

Val Pro Glu Ala Gln Glu Asp Val Glu Ala Thr Phe Pro Val His Gln
                165                 170                 175

Pro Gly Asn Tyr Ser Cys Ser Tyr Arg Thr Asp Gly Glu Gly Ala Leu
            180                 185                 190

Ser Glu Pro Ser Ala Thr Val Thr Ile Glu Glu Leu Ala Ala Pro Pro
            195                 200                 205

Pro Pro Val Leu Met His His Gly Glu Ser Ser Gln Val Leu His Pro
210                 215                 220

Gly Asn Lys Val Thr Leu Thr Cys Val Ala Pro Leu Ser Gly Val Asp
225                 230                 235                 240

Phe Gln Leu Arg Arg Gly Glu Lys Glu Leu Leu Val Pro Arg Ser Ser
                245                 250                 255

Thr Ser Pro Asp Arg Ile Phe Phe His Leu Asn Ala Val Ala Leu Gly
            260                 265                 270

Asp Gly Gly His Tyr Thr Cys Arg Tyr Arg Leu His Asp Asn Gln Asn
            275                 280                 285

Gly Trp Ser Gly Asp Ser Ala Pro Val Glu Leu Ile Leu Ser Asp Glu
290                 295                 300

Thr Leu Pro Ala Pro Glu Phe Ser Pro Glu Pro Glu Ser Gly Arg Ala
305                 310                 315                 320

Leu Arg Leu Arg Cys Leu Ala Pro Leu Glu Gly Ala Arg Phe Ala Leu
                325                 330                 335

Val Arg Glu Asp Arg Gly Gly Arg Arg Val His Arg Phe Gln Ser Pro
                340                 345                 350

Ala Gly Thr Glu Ala Leu Phe Glu Leu His Asn Ile Ser Val Ala Asp
            355                 360                 365

Ser Ala Asn Tyr Ser Cys Val Tyr Val Asp Leu Lys Pro Pro Phe Gly
            370                 375                 380

Gly Ser Ala Pro Ser Glu Arg Leu Glu Leu His Val Asp Gly Pro Pro
385                 390                 395                 400
```

```
Pro Arg Pro Gln Leu Arg Ala Thr Trp Ser Gly Ala Val Leu Ala Gly
            405                 410                 415

Arg Asp Ala Val Leu Arg Cys Glu Gly Pro Ile Pro Asp Val Thr Phe
            420                 425                 430

Glu Leu Leu Arg Glu Gly Glu Thr Lys Ala Val Lys Thr Val Arg Thr
            435                 440                 445

Pro Gly Ala Ala Ala Asn Leu Glu Leu Ile Phe Val Gly Pro Gln His
450                 455                 460

Ala Gly Asn Tyr Arg Cys Arg Tyr Arg Ser Trp Val Pro His Thr Phe
465                 470                 475                 480

Glu Ser Glu Leu Ser Asp Pro Val Glu Leu Leu Val Ala Glu Ser
            485                 490                 495

<210> SEQ ID NO 2
<211> LENGTH: 485
<212> TYPE: PRT
<213> ORGANISM: Homo sapiens

<400> SEQUENCE: 2

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
            35                  40                  45

Ser Thr Cys Glu Gln Leu Ala Lys Ala Asn Ala Gly Lys Pro Lys Asp
        50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
            115                 120                 125

His Gly Ala Thr Val Leu Ser Pro Thr Ala Val Phe Gly Thr Leu Ala
        130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
            195                 200                 205

Val Gly Val Phe Thr Ala Pro Gly Leu His Leu Lys Gln Pro Phe Val
        210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
            275                 280                 285
```

-continued

Lys Gly Phe Ser Leu Leu Ala Glu Pro Gln Glu Phe Trp Val Asp Asn
        290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Glu Val Pro Phe
                325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
        355                 360                 365

Met Lys Lys Leu Ser Pro Arg Thr Ile His Leu Thr Met Pro Gln Leu
    370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
        435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
                485

<210> SEQ ID NO 3
<211> LENGTH: 396
<212> TYPE: PRT
<213> ORGANISM: Homo sapiens

<400> SEQUENCE: 3

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln

```
                165                 170                 175
Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Thr Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 4
<211> LENGTH: 414
<212> TYPE: PRT
<213> ORGANISM: Homo sapiens

<400> SEQUENCE: 4

Met Arg Phe Lys Ser His Thr Val Glu Leu Arg Arg Pro Cys Ser Asp
1               5                   10                  15

Met Glu Gly Ala Ala Leu Leu Arg Val Ser Val Leu Cys Ile Trp Met
            20                  25                  30

Ser Ala Leu Phe Leu Gly Val Arg Val Arg Ala Glu Leu Ala Gly Ala
        35                  40                  45

Arg Val Gln Gln Asn Val Pro Ser Gly Thr Asp Thr Gly Asp Pro Gln
    50                  55                  60

Ser Lys Pro Leu Gly Asp Trp Ala Ala Gly Thr Met Asp Pro Glu Ser
65                  70                  75                  80

Ser Ile Phe Ile Glu Asp Ala Ile Lys Tyr Phe Lys Glu Lys Val Ser
                85                  90                  95

Thr Gln Asn Leu Leu Leu Leu Leu Thr Asp Asn Glu Ala Trp Asn Gly
            100                 105                 110

Phe Val Ala Ala Ala Glu Leu Pro Arg Asn Glu Ala Asp Glu Leu Arg
        115                 120                 125

Lys Ala Leu Asp Asn Leu Ala Arg Gln Met Ile Met Lys Asp Lys Asn
    130                 135                 140
```

```
Trp His Asp Lys Gly Gln Gln Tyr Arg Asn Trp Phe Leu Lys Glu Phe
145                 150                 155                 160

Pro Arg Leu Lys Ser Lys Leu Glu Asp Asn Ile Arg Arg Leu Arg Ala
            165                 170                 175

Leu Ala Asp Gly Val Gln Lys Val His Lys Gly Thr Thr Ile Ala Asn
        180                 185                 190

Val Val Ser Gly Ser Leu Ser Ile Ser Ser Gly Ile Leu Thr Leu Val
    195                 200                 205

Gly Met Gly Leu Ala Pro Phe Thr Glu Gly Gly Ser Leu Val Leu Leu
210                 215                 220

Glu Pro Gly Met Glu Leu Gly Ile Thr Ala Ala Leu Thr Gly Ile Thr
225                 230                 235                 240

Ser Ser Thr Ile Asp Tyr Gly Lys Lys Trp Trp Thr Gln Ala Gln Ala
                245                 250                 255

His Asp Leu Val Ile Lys Ser Leu Asp Lys Leu Lys Glu Val Lys Glu
            260                 265                 270

Phe Leu Gly Glu Asn Ile Ser Asn Phe Leu Ser Leu Ala Gly Asn Thr
        275                 280                 285

Tyr Gln Leu Thr Arg Gly Ile Gly Lys Asp Ile Arg Ala Leu Arg Arg
    290                 295                 300

Ala Arg Ala Asn Leu Gln Ser Val Pro His Ala Ser Ala Ser Arg Pro
305                 310                 315                 320

Arg Val Thr Glu Pro Ile Ser Ala Glu Ser Gly Glu Gln Val Glu Arg
                325                 330                 335

Val Asn Glu Pro Ser Ile Leu Glu Met Ser Arg Gly Val Lys Leu Thr
            340                 345                 350

Asp Val Ala Pro Val Ser Phe Phe Leu Val Leu Asp Val Val Tyr Leu
        355                 360                 365

Val Tyr Glu Ser Lys His Leu His Glu Gly Ala Lys Ser Glu Thr Ala
    370                 375                 380

Glu Glu Leu Lys Lys Val Ala Gln Glu Leu Glu Glu Lys Leu Asn Ile
385                 390                 395                 400

Leu Asn Asn Asn Tyr Lys Ile Leu Gln Ala Asp Gln Glu Leu
                405                 410

<210> SEQ ID NO 5
<211> LENGTH: 1065
<212> TYPE: PRT
<213> ORGANISM: Homo sapiens

<400> SEQUENCE: 5

Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr
            20                  25                  30

Trp Asp Tyr Ala Ser Asp His Gly Glu Lys Lys Leu Ile Ser Val Asp
        35                  40                  45

Thr Glu His Ser Asn Ile Tyr Leu Gln Asn Gly Pro Asp Arg Ile Gly
    50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110
```

```
Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140

Ala Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
            165                 170                 175

Arg Ile Tyr His Ser His Ile Asp Ala Pro Lys Asp Ile Ala Ser Gly
                180                 185                 190

Leu Ile Gly Pro Leu Ile Ile Cys Lys Lys Asp Ser Leu Asp Lys Glu
            195                 200                 205

Lys Glu Lys His Ile Asp Arg Glu Phe Val Val Met Phe Ser Val Val
        210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
            260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
    290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
            340                 345                 350

Gln Val Gln Glu Cys Asn Lys Ser Ser Ser Lys Asp Asn Ile Arg Gly
        355                 360                 365

Lys His Val Arg His Tyr Tyr Ile Ala Ala Glu Ile Ile Trp Asn
    370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415

Gly Gly Ser Tyr Lys Lys Leu Val Tyr Arg Glu Tyr Thr Asp Ala Ser
            420                 425                 430

Phe Thr Asn Arg Lys Glu Arg Gly Pro Glu Glu Glu His Leu Gly Ile
        435                 440                 445

Leu Gly Pro Val Ile Trp Ala Glu Val Gly Asp Thr Ile Arg Val Thr
    450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
            500                 505                 510

Glu Thr Phe Thr Tyr Glu Trp Thr Val Pro Lys Glu Val Gly Pro Thr
        515                 520                 525
```

-continued

Asn Ala Asp Pro Val Cys Leu Ala Lys Met Tyr Tyr Ser Ala Val Asp
530                     535                     540

Pro Thr Lys Asp Ile Phe Thr Gly Leu Ile Gly Pro Met Lys Ile Cys
545                     550                     555                     560

Lys Lys Gly Ser Leu His Ala Asn Gly Arg Gln Lys Asp Val Asp Lys
                565                     570                     575

Glu Phe Tyr Leu Phe Pro Thr Val Phe Asp Glu Asn Glu Ser Leu Leu
                580                     585                     590

Leu Glu Asp Asn Ile Arg Met Phe Thr Thr Ala Pro Asp Gln Val Asp
                595                     600                     605

Lys Glu Asp Glu Asp Phe Gln Glu Ser Asn Lys Met His Ser Met Asn
610                     615                     620

Gly Phe Met Tyr Gly Asn Gln Pro Gly Leu Thr Met Cys Lys Gly Asp
625                     630                     635                     640

Ser Val Val Trp Tyr Leu Phe Ser Ala Gly Asn Glu Ala Asp Val His
                645                     650                     655

Gly Ile Tyr Phe Ser Gly Asn Thr Tyr Leu Trp Arg Gly Glu Arg Arg
                660                     665                     670

Asp Thr Ala Asn Leu Phe Pro Gln Thr Ser Leu Thr Leu His Met Trp
                675                     680                     685

Pro Asp Thr Glu Gly Thr Phe Asn Val Glu Cys Leu Thr Thr Asp His
690                     695                     700

Tyr Thr Gly Gly Met Lys Gln Lys Tyr Thr Val Asn Gln Cys Arg Arg
705                     710                     715                     720

Gln Ser Glu Asp Ser Thr Phe Tyr Leu Gly Glu Arg Thr Tyr Tyr Ile
                725                     730                     735

Ala Ala Val Glu Val Glu Trp Asp Tyr Ser Pro Gln Arg Glu Trp Glu
                740                     745                     750

Lys Glu Leu His His Leu Gln Glu Gln Asn Val Ser Asn Ala Phe Leu
                755                     760                     765

Asp Lys Gly Glu Phe Tyr Ile Gly Ser Lys Tyr Lys Lys Val Val Tyr
770                     775                     780

Arg Gln Tyr Thr Asp Ser Thr Phe Arg Val Pro Val Glu Arg Lys Ala
785                     790                     795                     800

Glu Glu Glu His Leu Gly Ile Leu Gly Pro Gln Leu His Ala Asp Val
                805                     810                     815

Gly Asp Lys Val Lys Ile Ile Phe Lys Asn Met Ala Thr Arg Pro Tyr
                820                     825                     830

Ser Ile His Ala His Gly Val Gln Thr Glu Ser Ser Thr Val Thr Pro
                835                     840                     845

Thr Leu Pro Gly Glu Thr Leu Thr Tyr Val Trp Lys Ile Pro Glu Arg
850                     855                     860

Ser Gly Ala Gly Thr Glu Asp Ser Ala Cys Ile Pro Trp Ala Tyr Tyr
865                     870                     875                     880

Ser Thr Val Asp Gln Val Lys Asp Leu Tyr Ser Gly Leu Ile Gly Pro
                885                     890                     895

Leu Ile Val Cys Arg Arg Pro Tyr Leu Lys Val Phe Asn Pro Arg Arg
                900                     905                     910

Lys Leu Glu Phe Ala Leu Leu Phe Leu Val Phe Asp Glu Asn Glu Ser
                915                     920                     925

Trp Tyr Leu Asp Asp Asn Ile Lys Thr Tyr Ser Asp His Pro Glu Lys
930                     935                     940

Val Asn Lys Asp Asp Glu Glu Phe Ile Glu Ser Asn Lys Met His Ala

```
                  945                 950                 955                 960
Ile Asn Gly Arg Met Phe Gly Asn Leu Gln Gly Leu Thr Met His Val
                    965                 970                 975

Gly Asp Glu Val Asn Trp Tyr Leu Met Gly Met Gly Asn Glu Ile Asp
                    980                 985                 990

Leu His Thr Val His Phe His Gly His Ser Phe Gln Tyr Lys His Arg
                    995                1000                1005

Gly Val Tyr Ser Ser Asp Val Phe Asp Ile Phe Pro Gly Thr Tyr
           1010                1015                1020

Gln Thr Leu Glu Met Phe Pro Arg Thr Pro Gly Ile Trp Leu Leu
           1025                1030                1035

His Cys His Val Thr Asp His Ile His Ala Gly Met Glu Thr Thr
           1040                1045                1050

Tyr Thr Val Leu Gln Asn Glu Asp Thr Lys Ser Gly
           1055                1060                1065

<210> SEQ ID NO 6
<211> LENGTH: 251
<212> TYPE: PRT
<213> ORGANISM: Homo sapiens

<400> SEQUENCE: 6

Met Lys Ile Pro Trp Gly Ser Ile Pro Val Leu Met Leu Leu Leu
1               5                  10                  15

Leu Gly Leu Ile Asp Ile Ser Gln Ala Gln Leu Ser Cys Thr Gly Pro
            20                  25                  30

Pro Ala Ile Pro Gly Ile Pro Gly Ile Pro Gly Thr Pro Gly Pro Asp
                35                  40                  45

Gly Gln Pro Gly Thr Pro Gly Ile Lys Gly Glu Lys Gly Leu Pro Gly
    50                  55                  60

Leu Ala Gly Asp His Gly Glu Phe Gly Glu Lys Gly Asp Pro Gly Ile
65                  70                  75                  80

Pro Gly Asn Pro Gly Lys Val Gly Pro Lys Gly Pro Met Gly Pro Lys
                85                  90                  95

Gly Gly Pro Gly Ala Pro Gly Ala Pro Gly Pro Lys Gly Glu Ser Gly
            100                 105                 110

Asp Tyr Lys Ala Thr Gln Lys Ile Ala Phe Ser Ala Thr Arg Thr Ile
        115                 120                 125

Asn Val Pro Leu Arg Arg Asp Gln Thr Ile Arg Phe Asp His Val Ile
    130                 135                 140

Thr Asn Met Asn Asn Asn Tyr Glu Pro Arg Ser Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Leu Met Arg Gly Arg Glu Arg Ala Gln Lys Val
            180                 185                 190

Val Thr Phe Cys Asp Tyr Ala Tyr Asn Thr Phe Gln Val Thr Thr Gly
        195                 200                 205

Gly Met Val Leu Lys Leu Glu Gln Gly Glu Asn Val Phe Leu Gln Ala
    210                 215                 220

Thr Asp Lys Asn Ser Leu Leu Gly Met Glu Gly Ala Asn Ser Ile Phe
225                 230                 235                 240

Ser Gly Phe Leu Leu Phe Pro Asp Met Glu Ala
                245                 250
```

<210> SEQ ID NO 7
<211> LENGTH: 843
<212> TYPE: PRT
<213> ORGANISM: Homo sapiens

<400> SEQUENCE: 7

```
Met Lys Val Ile Ser Leu Phe Ile Leu Val Gly Phe Ile Gly Glu Phe
1               5                   10                  15

Gln Ser Phe Ser Ser Ala Ser Ser Pro Val Asn Cys Gln Trp Asp Phe
            20                  25                  30

Tyr Ala Pro Trp Ser Glu Cys Asn Gly Cys Thr Lys Thr Gln Thr Arg
        35                  40                  45

Arg Arg Ser Val Ala Val Tyr Gly Gln Tyr Gly Gly Gln Pro Cys Val
50                  55                  60

Gly Asn Ala Phe Glu Thr Gln Ser Cys Glu Pro Thr Arg Gly Cys Pro
65                  70                  75                  80

Thr Glu Glu Gly Cys Gly Glu Arg Phe Arg Cys Phe Ser Gly Gln Cys
                85                  90                  95

Ile Ser Lys Ser Leu Val Cys Asn Gly Asp Ser Asp Cys Asp Glu Asp
            100                 105                 110

Ser Ala Asp Glu Asp Arg Cys Glu Asp Ser Glu Arg Arg Pro Ser Cys
        115                 120                 125

Asp Ile Asp Lys Pro Pro Asn Ile Glu Leu Thr Gly Asn Gly Tyr
130                 135                 140

Asn Glu Leu Thr Gly Gln Phe Arg Asn Arg Val Ile Asn Thr Lys Ser
145                 150                 155                 160

Phe Gly Gly Gln Cys Arg Lys Val Phe Ser Gly Asp Gly Lys Asp Phe
                165                 170                 175

Tyr Arg Leu Ser Gly Asn Val Leu Ser Tyr Thr Phe Gln Val Lys Ile
            180                 185                 190

Asn Asn Asp Phe Asn Tyr Glu Phe Tyr Asn Ser Thr Trp Ser Tyr Val
        195                 200                 205

Lys His Thr Ser Thr Glu His Thr Ser Ser Arg Lys Arg Ser Phe
    210                 215                 220

Phe Arg Ser Ser Ser Ser Ser Arg Ser Tyr Thr Ser His Thr Asn
225                 230                 235                 240

Glu Ile His Lys Gly Lys Ser Tyr Gln Leu Leu Val Val Glu Asn Thr
                245                 250                 255

Val Glu Val Ala Gln Phe Ile Asn Asn Asn Pro Glu Phe Leu Gln Leu
            260                 265                 270

Ala Glu Pro Phe Trp Lys Glu Leu Ser His Leu Pro Ser Leu Tyr Asp
        275                 280                 285

Tyr Ser Ala Tyr Arg Arg Leu Ile Asp Gln Tyr Gly Thr His Tyr Leu
290                 295                 300

Gln Ser Gly Ser Leu Gly Gly Glu Tyr Arg Val Leu Phe Tyr Val Asp
305                 310                 315                 320

Ser Glu Lys Leu Lys Gln Asn Asp Phe Asn Ser Val Glu Glu Lys Lys
                325                 330                 335

Cys Lys Ser Ser Gly Trp His Phe Val Val Lys Phe Ser Ser His Gly
            340                 345                 350

Cys Lys Glu Leu Glu Asn Ala Leu Lys Ala Ala Ser Gly Thr Gln Asn
        355                 360                 365

Asn Val Leu Arg Gly Glu Pro Phe Ile Arg Gly Gly Gly Ala Gly Phe
370                 375                 380
```

-continued

```
Ile Ser Gly Leu Ser Tyr Leu Glu Leu Asp Asn Pro Ala Gly Asn Lys
385                 390                 395                 400

Arg Arg Tyr Ser Ala Trp Ala Glu Ser Val Thr Asn Leu Pro Gln Val
                405                 410                 415

Ile Lys Gln Lys Leu Thr Pro Leu Tyr Glu Leu Val Lys Glu Val Pro
            420                 425                 430

Cys Ala Ser Val Lys Lys Leu Tyr Leu Lys Trp Ala Leu Glu Glu Tyr
        435                 440                 445

Leu Asp Glu Phe Asp Pro Cys His Cys Arg Pro Cys Gln Asn Gly Gly
    450                 455                 460

Leu Ala Thr Val Glu Gly Thr His Cys Leu Cys His Cys Lys Pro Tyr
465                 470                 475                 480

Thr Phe Gly Ala Ala Cys Glu Gln Gly Val Leu Val Gly Asn Gln Ala
                485                 490                 495

Gly Gly Val Asp Gly Gly Trp Ser Cys Trp Ser Ser Trp Ser Pro Cys
            500                 505                 510

Val Gln Gly Lys Lys Thr Arg Ser Arg Glu Cys Asn Asn Pro Pro Pro
        515                 520                 525

Ser Gly Gly Gly Arg Ser Cys Val Gly Glu Thr Thr Glu Ser Thr Gln
    530                 535                 540

Cys Glu Asp Glu Glu Leu Glu His Leu Arg Leu Leu Glu Pro His Cys
545                 550                 555                 560

Phe Pro Leu Ser Leu Val Pro Thr Glu Phe Cys Pro Ser Pro Pro Ala
                565                 570                 575

Leu Lys Asp Gly Phe Val Gln Asp Glu Gly Thr Met Phe Pro Val Gly
            580                 585                 590

Lys Asn Val Val Tyr Thr Cys Asn Glu Gly Tyr Ser Leu Ile Gly Asn
        595                 600                 605

Pro Val Ala Arg Cys Gly Glu Asp Leu Arg Trp Leu Val Gly Glu Met
    610                 615                 620

His Cys Gln Lys Ile Ala Cys Val Leu Pro Val Leu Met Asp Gly Ile
625                 630                 635                 640

Gln Ser His Pro Gln Lys Pro Phe Tyr Thr Val Gly Glu Lys Val Thr
                645                 650                 655

Val Ser Cys Ser Gly Gly Met Ser Leu Glu Gly Pro Ser Ala Phe Leu
            660                 665                 670

Cys Gly Ser Ser Leu Lys Trp Ser Pro Glu Met Lys Asn Ala Arg Cys
        675                 680                 685

Val Gln Lys Glu Asn Pro Leu Thr Gln Ala Val Pro Lys Cys Gln Arg
    690                 695                 700

Trp Glu Lys Leu Gln Asn Ser Arg Cys Val Cys Lys Met Pro Tyr Glu
705                 710                 715                 720

Cys Gly Pro Ser Leu Asp Val Cys Ala Gln Asp Glu Arg Ser Lys Arg
                725                 730                 735

Ile Leu Pro Leu Thr Val Cys Lys Met His Val Leu His Cys Gln Gly
            740                 745                 750

Arg Asn Tyr Thr Leu Thr Gly Arg Asp Ser Cys Thr Leu Pro Ala Ser
        755                 760                 765

Ala Glu Lys Ala Cys Gly Ala Cys Pro Leu Trp Gly Lys Cys Asp Ala
    770                 775                 780

Glu Ser Ser Lys Cys Val Cys Arg Glu Ala Ser Glu Cys Glu Glu Glu
785                 790                 795                 800
```

```
Gly Phe Ser Ile Cys Val Glu Val Asn Gly Lys Glu Gln Thr Met Ser
                805                 810                 815

Glu Cys Glu Ala Gly Ala Leu Arg Cys Arg Gly Gln Ser Ile Ser Val
            820                 825                 830

Thr Ser Ile Arg Pro Cys Ala Ala Glu Thr Gln
        835                 840

<210> SEQ ID NO 8
<211> LENGTH: 1744
<212> TYPE: PRT
<213> ORGANISM: Homo sapiens

<400> SEQUENCE: 8

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335
```

```
Arg Leu Tyr Val Ala Ala Ile Ile Glu Tyr Pro Gly Gly Glu Met
             340                 345                 350
Glu Glu Ala Glu Leu Thr Ser Trp Tyr Phe Val Ser Ser Pro Phe Ser
             355                 360                 365
Leu Asp Leu Ser Lys Thr Lys Arg His Leu Val Pro Gly Ala Pro Phe
    370                 375                 380
Leu Leu Gln Ala Leu Val Arg Glu Met Ser Gly Ser Pro Ala Ser Gly
385                 390                 395                 400
Ile Pro Val Lys Val Ser Ala Thr Val Ser Ser Pro Gly Ser Val Pro
             405                 410                 415
Glu Val Gln Asp Ile Gln Gln Asn Thr Asp Gly Ser Gly Gln Val Ser
             420                 425                 430
Ile Pro Ile Ile Ile Pro Gln Thr Ile Ser Glu Leu Gln Leu Ser Val
             435                 440                 445
Ser Ala Gly Ser Pro His Pro Ala Ile Ala Arg Leu Thr Val Ala Ala
             450                 455                 460
Pro Pro Ser Gly Gly Pro Gly Phe Leu Ser Ile Glu Arg Pro Asp Ser
465                 470                 475                 480
Arg Pro Pro Arg Val Gly Asp Thr Leu Asn Leu Asn Leu Arg Ala Val
                    485                 490                 495
Gly Ser Gly Ala Thr Phe Ser His Tyr Tyr Tyr Met Ile Leu Ser Arg
             500                 505                 510
Gly Gln Ile Val Phe Met Asn Arg Glu Pro Lys Arg Thr Leu Thr Ser
             515                 520                 525
Val Ser Val Phe Val Asp His His Leu Ala Pro Ser Phe Tyr Phe Val
    530                 535                 540
Ala Phe Tyr Tyr His Gly Asp His Pro Val Ala Asn Ser Leu Arg Val
545                 550                 555                 560
Asp Val Gln Ala Gly Ala Cys Glu Gly Lys Leu Glu Leu Ser Val Asp
                565                 570                 575
Gly Ala Lys Gln Tyr Arg Asn Gly Glu Ser Val Lys Leu His Leu Glu
             580                 585                 590
Thr Asp Ser Leu Ala Leu Val Ala Leu Gly Ala Leu Asp Thr Ala Leu
    595                 600                 605
Tyr Ala Ala Gly Ser Lys Ser His Lys Pro Leu Asn Met Gly Lys Val
610                 615                 620
Phe Glu Ala Met Asn Ser Tyr Asp Leu Gly Cys Gly Pro Gly Gly Gly
625                 630                 635                 640
Asp Ser Ala Leu Gln Val Phe Gln Ala Ala Gly Leu Ala Phe Ser Asp
                645                 650                 655
Gly Asp Gln Trp Thr Leu Ser Arg Lys Arg Leu Ser Cys Pro Lys Glu
             660                 665                 670
Lys Thr Thr Arg Lys Lys Arg Asn Val Asn Phe Gln Lys Ala Ile Asn
             675                 680                 685
Glu Lys Leu Gly Gln Tyr Ala Ser Pro Thr Ala Lys Arg Cys Cys Gln
             690                 695                 700
Asp Gly Val Thr Arg Leu Pro Met Met Arg Ser Cys Glu Gln Arg Ala
705                 710                 715                 720
Ala Arg Val Gln Gln Pro Asp Cys Arg Glu Pro Phe Leu Ser Cys Cys
             725                 730                 735
Gln Phe Ala Glu Ser Leu Arg Lys Lys Ser Arg Asp Lys Gly Gln Ala
             740                 745                 750
```

-continued

Gly Leu Gln Arg Ala Leu Glu Ile Leu Gln Glu Asp Leu Ile Asp
            755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
            805                 810                 815

Lys Gly Leu Cys Val Ala Thr Pro Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
        850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
            885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Leu
            930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
            965                 970                 975

Tyr Val Arg Val Thr Ala Ser Asp Pro Leu Asp Thr Leu Gly Ser Glu
            980                 985                 990

Gly Ala Leu Ser Pro Gly Gly Val Ala Ser Leu Leu Arg Leu Pro Arg
            995                 1000                1005

Gly Cys Gly Glu Gln Thr Met Ile Tyr Leu Ala Pro Thr Leu Ala
    1010                1015                1020

Ala Ser Arg Tyr Leu Asp Lys Thr Glu Gln Trp Ser Thr Leu Pro
    1025                1030                1035

Pro Glu Thr Lys Asp His Ala Val Asp Leu Ile Gln Lys Gly Tyr
    1040                1045                1050

Met Arg Ile Gln Gln Phe Arg Lys Ala Asp Gly Ser Tyr Ala Ala
    1055                1060                1065

Trp Leu Ser Arg Gly Ser Ser Thr Trp Leu Thr Ala Phe Val Leu
    1070                1075                1080

Lys Val Leu Ser Leu Ala Gln Glu Gln Val Gly Ser Pro Glu
    1085                1090                1095

Lys Leu Gln Glu Thr Ser Asn Trp Leu Leu Ser Gln Gln Gln Ala
    1100                1105                1110

Asp Gly Ser Phe Gln Asp Leu Ser Pro Val Ile His Arg Ser Met
    1115                1120                1125

Gln Gly Gly Leu Val Gly Asn Asp Glu Thr Val Ala Leu Thr Ala
    1130                1135                1140

Phe Val Thr Ile Ala Leu His His Gly Leu Ala Val Phe Gln Asp
    1145                1150                1155

Glu Gly Ala Glu Pro Leu Lys Gln Arg Val Glu Ala Ser Ile Ser

```
             1160                1165                1170
Lys Ala Ser Ser Phe Leu Gly Glu Lys Ala Ser Ala Gly Leu Leu
     1175                1180                1185
Gly Ala His Ala Ala Ala Ile Thr Ala Tyr Ala Leu Thr Leu Thr
     1190                1195                1200
Lys Ala Pro Ala Asp Leu Arg Gly Val Ala His Asn Asn Leu Met
     1205                1210                1215
Ala Met Ala Gln Glu Thr Gly Asp Asn Leu Tyr Trp Gly Ser Val
     1220                1225                1230
Thr Gly Ser Gln Ser Asn Ala Val Ser Pro Thr Pro Ala Pro Arg
     1235                1240                1245
Asn Pro Ser Asp Pro Met Pro Gln Ala Pro Ala Leu Trp Ile Glu
     1250                1255                1260
Thr Thr Ala Tyr Ala Leu Leu His Leu Leu Leu His Glu Gly Lys
     1265                1270                1275
Ala Glu Met Ala Asp Gln Ala Ala Ala Trp Leu Thr Arg Gln Gly
     1280                1285                1290
Ser Phe Gln Gly Gly Phe Arg Ser Thr Gln Asp Thr Val Ile Ala
     1295                1300                1305
Leu Asp Ala Leu Ser Ala Tyr Trp Ile Ala Ser His Thr Thr Glu
     1310                1315                1320
Glu Arg Gly Leu Asn Val Thr Leu Ser Ser Thr Gly Arg Asn Gly
     1325                1330                1335
Phe Lys Ser His Ala Leu Gln Leu Asn Asn Arg Gln Ile Arg Gly
     1340                1345                1350
Leu Glu Glu Glu Leu Gln Phe Ser Leu Gly Ser Lys Ile Asn Val
     1355                1360                1365
Lys Val Gly Gly Asn Ser Lys Gly Thr Leu Lys Val Leu Arg Thr
     1370                1375                1380
Tyr Asn Val Leu Asp Met Lys Asn Thr Thr Cys Gln Asp Leu Gln
     1385                1390                1395
Ile Glu Val Thr Val Lys Gly His Val Glu Tyr Thr Met Glu Ala
     1400                1405                1410
Asn Glu Asp Tyr Glu Asp Tyr Glu Tyr Asp Glu Leu Pro Ala Lys
     1415                1420                1425
Asp Asp Pro Asp Ala Pro Leu Gln Pro Val Thr Pro Leu Gln Leu
     1430                1435                1440
Phe Glu Gly Arg Arg Asn Arg Arg Arg Arg Glu Ala Pro Lys Val
     1445                1450                1455
Val Glu Glu Gln Glu Ser Arg Val His Tyr Thr Val Cys Ile Trp
     1460                1465                1470
Arg Asn Gly Lys Val Gly Leu Ser Gly Met Ala Ile Ala Asp Val
     1475                1480                1485
Thr Leu Leu Ser Gly Phe His Ala Leu Arg Ala Asp Leu Glu Lys
     1490                1495                1500
Leu Thr Ser Leu Ser Asp Arg Tyr Val Ser His Phe Glu Thr Glu
     1505                1510                1515
Gly Pro His Val Leu Leu Tyr Phe Asp Ser Val Pro Thr Ser Arg
     1520                1525                1530
Glu Cys Val Gly Phe Glu Ala Val Gln Glu Val Pro Val Gly Leu
     1535                1540                1545
Val Gln Pro Ala Ser Ala Thr Leu Tyr Asp Tyr Tyr Asn Pro Glu
     1550                1555                1560
```

```
Arg Arg Cys Ser Val Phe Tyr Gly Ala Pro Ser Lys Ser Arg Leu
    1565                1570                1575

Leu Ala Thr Leu Cys Ser Ala Glu Val Cys Gln Cys Ala Glu Gly
    1580                1585                1590

Lys Cys Pro Arg Gln Arg Ala Leu Glu Arg Gly Leu Gln Asp
    1595                1600                1605

Glu Asp Gly Tyr Arg Met Lys Phe Ala Cys Tyr Tyr Pro Arg Val
    1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val

<210> SEQ ID NO 9
<211> LENGTH: 764
<212> TYPE: PRT
<213> ORGANISM: Homo sapiens

<400> SEQUENCE: 9

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Gln
                20                  25                  30

Pro Gln Gly Ser Cys Ser Leu Glu Gly Val Glu Ile Lys Gly Gly Ser
            35                  40                  45

Phe Arg Leu Leu Gln Glu Gly Gln Ala Leu Glu Tyr Val Cys Pro Ser
        50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175
```

```
Val Gly Ser Gln Tyr Arg Leu Glu Asp Ser Val Thr Tyr His Cys Ser
            180                 185                 190

Arg Gly Leu Thr Leu Arg Gly Ser Gln Arg Thr Cys Gln Glu Gly
            195                 200             205

Gly Ser Trp Ser Gly Thr Glu Pro Ser Cys Gln Asp Ser Phe Met Tyr
            210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
            290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
            355                 360                 365

Pro Asp Asp Val Pro Pro Glu Gly Trp Asn Arg Thr Arg His Val Ile
            370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
            450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
            515                 520                 525

Thr Val Asp Asp Lys Glu His Ser Ile Lys Val Ser Val Gly Gly Glu
            530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590
```

-continued

Arg Pro Ile Cys Leu Pro Cys Thr Glu Gly Thr Thr Arg Ala Leu Arg
            595                 600                 605

Leu Pro Pro Thr Thr Thr Cys Gln Gln Gln Lys Glu Glu Leu Leu Pro
610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
            645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
            675                 680                 685

Tyr Ala Asp Pro Asn Thr Cys Arg Gly Asp Ser Gly Gly Pro Leu Ile
            690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Val Pro Ala
            725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
            755                 760

<210> SEQ ID NO 10
<211> LENGTH: 1231
<212> TYPE: PRT
<213> ORGANISM: Homo sapiens

<400> SEQUENCE: 10

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

```
Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620
```

```
Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Glu
            645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705             710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785             790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
            885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
        980                 985                 990

Pro Ser Phe Glu Asn Ala Ile Pro Met Gly Glu Lys Lys Asp Val Tyr
            995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
```

-continued

```
               1040                1045                1050
Val Gln Asn Ala Tyr Ile Val Ser Arg Gln Met Ser Lys Tyr Pro
        1055                1060                1065

Ser Gly Glu Arg Val Arg Tyr Gln Cys Arg Ser Pro Tyr Glu Met
        1070                1075                1080

Phe Gly Asp Glu Glu Val Met Cys Leu Asn Gly Asn Trp Thr Glu
        1085                1090                1095

Pro Pro Gln Cys Lys Asp Ser Thr Gly Lys Cys Gly Pro Pro Pro
        1100                1105                1110

Pro Ile Asp Asn Gly Asp Ile Thr Ser Phe Pro Leu Ser Val Tyr
        1115                1120                1125

Ala Pro Ala Ser Ser Val Glu Tyr Gln Cys Gln Asn Leu Tyr Gln
        1130                1135                1140

Leu Glu Gly Asn Lys Arg Ile Thr Cys Arg Asn Gly Gln Trp Ser
        1145                1150                1155

Glu Pro Pro Lys Cys Leu His Pro Cys Val Ile Ser Arg Glu Ile
        1160                1165                1170

Met Glu Asn Tyr Asn Ile Ala Leu Arg Trp Thr Ala Lys Gln Lys
        1175                1180                1185

Leu Tyr Ser Arg Thr Gly Glu Ser Val Glu Phe Val Cys Lys Arg
        1190                1195                1200

Gly Tyr Arg Leu Ser Ser Arg Ser His Thr Leu Arg Thr Thr Cys
        1205                1210                1215

Trp Asp Gly Lys Leu Glu Tyr Pro Thr Cys Ala Lys Arg
        1220                1225                1230
```

<210> SEQ ID NO 11
<211> LENGTH: 782
<212> TYPE: PRT
<213> ORGANISM: Homo sapiens

<400> SEQUENCE: 11

```
Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Gly Gly Val Ala Ser Gly Phe
                165                 170                 175
```

-continued

```
Lys His Val Val Pro Asn Glu Val Val Val Gln Arg Leu Phe Gln Val
                180                 185                 190

Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
        210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
        435                 440                 445

Ile Trp Arg Ile Glu Gly Ser Asn Lys Val Pro Val Asp Pro Ala Thr
450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
```

```
                    595                 600                 605
    Gly Ala Ser Glu Ala Glu Lys Thr Gly Ala Gln Glu Leu Leu Arg Val
                    610                 615                 620

Leu Arg Ala Gln Pro Val Gln Val Ala Glu Gly Ser Glu Pro Asp Gly
    625                 630                 635                 640

Phe Trp Glu Ala Leu Gly Gly Lys Ala Ala Tyr Arg Thr Ser Pro Arg
                    645                 650                 655

Leu Lys Asp Lys Lys Met Asp Ala His Pro Pro Arg Leu Phe Ala Cys
                    660                 665                 670

Ser Asn Lys Ile Gly Arg Phe Val Ile Glu Glu Val Pro Gly Glu Leu
                    675                 680                 685

Met Gln Glu Asp Leu Ala Thr Asp Val Met Leu Leu Asp Thr Trp
                    690                 695                 700

Asp Gln Val Phe Val Trp Val Gly Lys Asp Ser Gln Glu Glu Glu Lys
    705                 710                 715                 720

Thr Glu Ala Leu Thr Ser Ala Lys Arg Tyr Ile Glu Thr Asp Pro Ala
                    725                 730                 735

Asn Arg Asp Arg Arg Thr Pro Ile Thr Val Val Lys Gln Gly Phe Glu
                    740                 745                 750

Pro Pro Ser Phe Val Gly Trp Phe Leu Gly Trp Asp Asp Tyr Trp
                    755                 760                 765

Ser Val Asp Pro Leu Asp Arg Ala Met Ala Glu Leu Ala Ala
                    770                 775                 780

<210> SEQ ID NO 12
<211> LENGTH: 461
<212> TYPE: PRT
<213> ORGANISM: Homo sapiens

<400> SEQUENCE: 12

Ala Arg Val Leu Gly Ala Pro Val Ala Leu Gly Leu Trp Ser Leu Cys
    1               5                   10                  15

Trp Ser Leu Ala Ile Ala Thr Pro Leu Pro Thr Ser Ala His Gly
                    20                  25                  30

Asn Val Ala Glu Gly Glu Thr Lys Pro Asp Pro Asp Val Thr Glu Arg
                    35                  40                  45

Cys Ser Asp Gly Trp Ser Phe Asp Ala Thr Thr Leu Asp Asp Asn Gly
                    50                  55                  60

Thr Met Leu Phe Phe Lys Gly Glu Phe Val Trp Lys Ser His Lys Trp
    65                  70                  75                  80

Asp Arg Glu Leu Ile Ser Glu Arg Trp Lys Asn Phe Pro Ser Pro Val
                    85                  90                  95

Asp Ala Ala Phe Arg Gln Gly His Asn Ser Val Phe Leu Ile Lys Gly
                    100                 105                 110

Asp Lys Val Trp Val Tyr Pro Pro Glu Lys Lys Glu Lys Gly Tyr Pro
                    115                 120                 125

Lys Leu Leu Gln Asp Glu Phe Pro Gly Ile Pro Ser Pro Leu Asp Ala
                    130                 135                 140

Ala Val Glu Cys His Arg Gly Glu Cys Gln Ala Glu Gly Val Leu Phe
    145                 150                 155                 160

Phe Gln Gly Asp Arg Glu Trp Phe Trp Asp Leu Ala Thr Gly Thr Met
                    165                 170                 175

Lys Glu Arg Ser Trp Pro Ala Val Gly Asn Cys Ser Ser Ala Leu Arg
                    180                 185                 190
```

```
Trp Leu Gly Arg Tyr Tyr Cys Phe Gln Gly Asn Gln Phe Leu Arg Phe
            195                 200                 205

Asp Pro Val Arg Gly Glu Val Pro Pro Arg Tyr Pro Arg Asp Val Arg
210                 215                 220

Asp Tyr Phe Met Pro Cys Pro Arg Gly His Gly His Arg Asn Gly
225                 230                 235                 240

Thr Gly His Gly Asn Ser Thr His His Gly Pro Glu Tyr Met Arg Cys
            245                 250                 255

Ser Pro His Leu Val Leu Ser Ala Leu Thr Ser Asp Asn His Gly Ala
            260                 265                 270

Thr Tyr Ala Phe Ser Gly Thr His Tyr Trp Arg Leu Asp Thr Ser Arg
            275                 280                 285

Asp Gly Trp His Ser Trp Pro Ile Ala His Gln Trp Pro Gln Gly Pro
290                 295                 300

Ser Ala Val Asp Ala Ala Phe Ser Trp Glu Glu Lys Leu Tyr Leu Val
305                 310                 315                 320

Gln Gly Thr Gln Val Tyr Val Phe Leu Thr Lys Gly Gly Tyr Thr Leu
            325                 330                 335

Val Ser Gly Tyr Pro Lys Arg Leu Glu Lys Glu Val Gly Thr Pro His
            340                 345                 350

Gly Ile Ile Leu Asp Ser Val Asp Ala Ala Phe Ile Cys Pro Gly Ser
            355                 360                 365

Ser Arg Leu His Ile Met Ala Gly Arg Arg Leu Trp Trp Leu Asp Leu
            370                 375                 380

Lys Ser Gly Ala Gln Ala Thr Trp Thr Glu Leu Pro Trp Pro His Glu
385                 390                 395                 400

Lys Val Asp Gly Ala Leu Cys Met Glu Lys Ser Leu Gly Pro Asn Ser
                    405                 410                 415

Cys Ser Ala Asn Gly Pro Gly Leu Tyr Leu Ile His Gly Pro Asn Leu
                    420                 425                 430

Tyr Cys Tyr Ser Asp Val Glu Lys Leu Asn Ala Ala Lys Ala Leu Pro
            435                 440                 445

Gln Pro Gln Asn Val Thr Ser Leu Leu Gly Cys Thr His
    450                 455                 460

<210> SEQ ID NO 13
<211> LENGTH: 525
<212> TYPE: PRT
<213> ORGANISM: Homo sapiens

<400> SEQUENCE: 13

Met Lys Ala Leu Ile Ala Ala Leu Leu Leu Ile Thr Leu Gln Tyr Ser
1               5                   10                  15

Cys Ala Val Ser Pro Thr Asp Cys Ser Ala Val Glu Pro Glu Ala Glu
                20                  25                  30

Lys Ala Leu Asp Leu Ile Asn Lys Arg Arg Asp Gly Tyr Leu Phe
            35                  40                  45

Gln Leu Leu Arg Ile Ala Asp Ala His Leu Asp Arg Val Glu Asn Thr
    50                  55                  60

Thr Val Tyr Tyr Leu Val Leu Asp Val Gln Glu Ser Asp Cys Ser Val
65                  70                  75                  80

Leu Ser Arg Lys Tyr Trp Asn Asp Cys Glu Pro Pro Asp Ser Arg Arg
                85                  90                  95

Pro Ser Glu Ile Val Ile Gly Gln Cys Lys Val Ile Ala Thr Arg His
                100                 105                 110
```

```
Ser His Glu Ser Gln Asp Leu Arg Val Ile Asp Phe Asn Cys Thr Thr
        115                 120                 125

Ser Ser Val Ser Ser Ala Leu Ala Asn Thr Lys Asp Ser Pro Val Leu
    130                 135                 140

Ile Asp Phe Phe Glu Asp Thr Glu Arg Tyr Arg Lys Gln Ala Asn Lys
145                 150                 155                 160

Ala Leu Glu Lys Tyr Lys Glu Glu Asn Asp Asp Phe Ala Ser Phe Arg
                165                 170                 175

Val Asp Arg Ile Glu Arg Val Ala Arg Val Arg Gly Gly Glu Gly Thr
                180                 185                 190

Gly Tyr Phe Val Asp Phe Ser Val Arg Asn Cys Pro Arg His His Phe
            195                 200                 205

Pro Arg His Pro Asn Val Phe Gly Phe Cys Arg Ala Asp Leu Phe Tyr
        210                 215                 220

Asp Val Glu Ala Leu Asp Leu Glu Ser Pro Lys Asn Leu Val Ile Asn
225                 230                 235                 240

Cys Glu Val Phe Asp Pro Gln Glu His Glu Asn Ile Asn Gly Val Pro
                245                 250                 255

Pro His Leu Gly His Pro Phe Trp Gly His Glu Arg Ser Ser
            260                 265                 270

Thr Thr Lys Pro Pro Phe Lys Pro His Gly Ser Arg Asp His His His
        275                 280                 285

Pro His Lys Pro His Glu His Gly Pro Pro Pro Pro Asp Glu Arg
        290                 295                 300

Asp His Ser His Gly Pro Leu Pro Gln Gly Pro Pro Leu Leu
305                 310                 315                 320

Pro Met Ser Cys Ser Cys Gln His Ala Thr Phe Gly Thr Asn Gly
                325                 330                 335

Ala Gln Arg His Ser His Asn Asn Ser Ser Asp Leu His Pro His
            340                 345                 350

Lys His His Ser His Glu Gln His Pro His Gly His His Pro His Ala
        355                 360                 365

His His Pro His Glu His Asp Thr His Arg Gln His Pro His Gly His
    370                 375                 380

His Pro His Gly His His Pro His Gly His His Pro His Gly His His
385                 390                 395                 400

Pro His Gly His His Pro His Cys His Asp Phe Gln Asp Tyr Gly Pro
                405                 410                 415

Cys Asp Pro Pro Pro His Asn Gln Gly His Cys Cys His Gly His Gly
                420                 425                 430

Pro Pro Pro Gly His Leu Arg Arg Gly Pro Gly Lys Gly Pro Arg
            435                 440                 445

Pro Phe His Cys Arg Gln Ile Gly Ser Val Tyr Arg Leu Pro Pro Leu
        450                 455                 460

Arg Lys Gly Glu Val Leu Pro Leu Pro Glu Ala Asn Phe Pro Ser Phe
465                 470                 475                 480

Pro Leu Pro His His Lys His Pro Leu Lys Pro Asp Asn Gln Pro Phe
                485                 490                 495

Pro Gln Ser Val Ser Glu Ser Cys Pro Gly Lys Phe Lys Ser Gly Phe
            500                 505                 510

Pro Gln Val Ser Met Phe Phe Thr His Thr Phe Pro Lys
        515                 520                 525
```

<210> SEQ ID NO 14
<211> LENGTH: 605
<212> TYPE: PRT
<213> ORGANISM: Homo sapiens

<400> SEQUENCE: 14

| Met | Ala | Leu | Arg | Lys | Gly | Gly | Leu | Ala | Leu | Ala | Leu | Leu | Leu | Leu | Ser |
|---|---|---|---|---|---|---|---|---|---|---|---|---|---|---|---|
| 1 | | | | 5 | | | | | 10 | | | | | 15 | |

| Trp | Val | Ala | Leu | Gly | Pro | Arg | Ser | Leu | Glu | Gly | Ala | Asp | Pro | Gly | Thr |
|---|---|---|---|---|---|---|---|---|---|---|---|---|---|---|---|
| | | | 20 | | | | | 25 | | | | | 30 | | |

| Pro | Gly | Glu | Ala | Glu | Gly | Pro | Ala | Cys | Pro | Ala | Ala | Cys | Val | Cys | Ser |
|---|---|---|---|---|---|---|---|---|---|---|---|---|---|---|---|
| | | | | 35 | | | | | 40 | | | | 45 | | |

| Tyr | Asp | Asp | Ala | Asp | Glu | Leu | Ser | Val | Phe | Cys | Ser | Ser | Arg | Asn |
|---|---|---|---|---|---|---|---|---|---|---|---|---|---|---|
| 50 | | | | | 55 | | | | 60 | | | | | |

| Leu | Thr | Arg | Leu | Pro | Asp | Gly | Val | Pro | Gly | Thr | Gln | Ala | Leu | Trp |
|---|---|---|---|---|---|---|---|---|---|---|---|---|---|---|
| 65 | | | | 70 | | | | | 75 | | | | | 80 |

| Leu | Asp | Gly | Asn | Asn | Leu | Ser | Ser | Val | Pro | Pro | Ala | Ala | Phe | Gln | Asn |
|---|---|---|---|---|---|---|---|---|---|---|---|---|---|---|---|
| | | | | 85 | | | | | 90 | | | | | 95 | |

| Leu | Ser | Ser | Leu | Gly | Phe | Leu | Asn | Leu | Gln | Gly | Gly | Gln | Leu | Gly | Ser |
|---|---|---|---|---|---|---|---|---|---|---|---|---|---|---|---|
| | | | | 100 | | | | | 105 | | | | | 110 | |

| Leu | Glu | Pro | Gln | Ala | Leu | Leu | Gly | Leu | Glu | Asn | Leu | Cys | His | Leu | His |
|---|---|---|---|---|---|---|---|---|---|---|---|---|---|---|---|
| | | | 115 | | | | | 120 | | | | | 125 | | |

| Leu | Glu | Arg | Asn | Gln | Leu | Arg | Ser | Leu | Ala | Leu | Gly | Thr | Phe | Ala | His |
|---|---|---|---|---|---|---|---|---|---|---|---|---|---|---|---|
| | 130 | | | | | 135 | | | | | 140 | | | | |

| Thr | Pro | Ala | Leu | Ala | Ser | Leu | Gly | Leu | Ser | Asn | Asn | Arg | Leu | Ser | Arg |
|---|---|---|---|---|---|---|---|---|---|---|---|---|---|---|---|
| 145 | | | | | 150 | | | | | 155 | | | | | 160 |

| Leu | Glu | Asp | Gly | Leu | Phe | Glu | Gly | Leu | Gly | Ser | Leu | Trp | Asp | Leu | Asn |
|---|---|---|---|---|---|---|---|---|---|---|---|---|---|---|---|
| | | | | 165 | | | | | 170 | | | | | 175 | |

| Leu | Gly | Trp | Asn | Ser | Leu | Ala | Val | Leu | Pro | Asp | Ala | Ala | Phe | Arg | Gly |
|---|---|---|---|---|---|---|---|---|---|---|---|---|---|---|---|
| | | | 180 | | | | | 185 | | | | | 190 | | |

| Leu | Gly | Ser | Leu | Arg | Glu | Leu | Val | Leu | Ala | Gly | Asn | Arg | Leu | Ala | Tyr |
|---|---|---|---|---|---|---|---|---|---|---|---|---|---|---|---|
| | | | 195 | | | | | 200 | | | | | 205 | | |

| Leu | Gln | Pro | Ala | Leu | Phe | Ser | Gly | Leu | Ala | Glu | Leu | Arg | Glu | Leu | Asp |
|---|---|---|---|---|---|---|---|---|---|---|---|---|---|---|---|
| | 210 | | | | | 215 | | | | | 220 | | | | |

| Leu | Ser | Arg | Asn | Ala | Leu | Arg | Ala | Ile | Lys | Ala | Asn | Val | Phe | Val | Gln |
|---|---|---|---|---|---|---|---|---|---|---|---|---|---|---|---|
| 225 | | | | | 230 | | | | | 235 | | | | | 240 |

| Leu | Pro | Arg | Leu | Gln | Lys | Leu | Tyr | Leu | Asp | Arg | Asn | Leu | Ile | Ala | Ala |
|---|---|---|---|---|---|---|---|---|---|---|---|---|---|---|---|
| | | | | 245 | | | | | 250 | | | | | 255 | |

| Val | Ala | Pro | Gly | Ala | Phe | Leu | Gly | Leu | Lys | Ala | Leu | Arg | Trp | Leu | Asp |
|---|---|---|---|---|---|---|---|---|---|---|---|---|---|---|---|
| | | | 260 | | | | | 265 | | | | | 270 | | |

| Leu | Ser | His | Asn | Arg | Val | Ala | Gly | Leu | Leu | Glu | Asp | Thr | Phe | Pro | Gly |
|---|---|---|---|---|---|---|---|---|---|---|---|---|---|---|---|
| | | | 275 | | | | | 280 | | | | | 285 | | |

| Leu | Leu | Gly | Leu | Arg | Val | Leu | Arg | Leu | Ser | His | Asn | Ala | Ile | Ala | Ser |
|---|---|---|---|---|---|---|---|---|---|---|---|---|---|---|---|
| | 290 | | | | | 295 | | | | | 300 | | | | |

| Leu | Arg | Pro | Arg | Thr | Phe | Lys | Asp | Leu | His | Phe | Leu | Glu | Glu | Leu | Gln |
|---|---|---|---|---|---|---|---|---|---|---|---|---|---|---|---|
| 305 | | | | | 310 | | | | | 315 | | | | | 320 |

| Leu | Gly | His | Asn | Arg | Ile | Arg | Gln | Leu | Ala | Glu | Arg | Ser | Phe | Glu | Gly |
|---|---|---|---|---|---|---|---|---|---|---|---|---|---|---|---|
| | | | | 325 | | | | | 330 | | | | | 335 | |

| Leu | Gly | Gln | Leu | Glu | Val | Leu | Thr | Leu | Asp | His | Asn | Gln | Leu | Gln | Glu |
|---|---|---|---|---|---|---|---|---|---|---|---|---|---|---|---|
| | | | 340 | | | | | 345 | | | | | 350 | | |

| Val | Lys | Ala | Gly | Ala | Phe | Leu | Gly | Leu | Thr | Asn | Val | Ala | Val | Met | Asn |
|---|---|---|---|---|---|---|---|---|---|---|---|---|---|---|---|
| | | 355 | | | | | 360 | | | | | 365 | | | |

| Leu | Ser | Gly | Asn | Cys | Leu | Arg | Asn | Leu | Pro | Glu | Gln | Val | Phe | Arg | Gly |
|---|---|---|---|---|---|---|---|---|---|---|---|---|---|---|---|
| | 370 | | | | | 375 | | | | | 380 | | | | |

```
Leu Gly Lys Leu His Ser Leu His Leu Glu Gly Ser Cys Leu Gly Arg
385                 390                 395                 400

Ile Arg Pro His Thr Phe Thr Gly Leu Ser Gly Leu Arg Arg Leu Phe
            405                 410                 415

Leu Lys Asp Asn Gly Leu Val Gly Ile Glu Glu Gln Ser Leu Trp Gly
        420                 425                 430

Leu Ala Glu Leu Leu Glu Leu Asp Leu Thr Ser Asn Gln Leu Thr His
    435                 440                 445

Leu Pro His Arg Leu Phe Gln Gly Leu Gly Lys Leu Glu Tyr Leu Leu
450                 455                 460

Leu Ser Arg Asn Arg Leu Ala Glu Leu Pro Ala Asp Ala Leu Gly Pro
465                 470                 475                 480

Leu Gln Arg Ala Phe Trp Leu Asp Val Ser His Asn Arg Leu Glu Ala
            485                 490                 495

Leu Pro Asn Ser Leu Leu Ala Pro Leu Gly Arg Leu Arg Tyr Leu Ser
        500                 505                 510

Leu Arg Asn Asn Ser Leu Arg Thr Phe Thr Pro Gln Pro Pro Gly Leu
    515                 520                 525

Glu Arg Leu Trp Leu Glu Gly Asn Pro Trp Asp Cys Gly Cys Pro Leu
530                 535                 540

Lys Ala Leu Arg Asp Phe Ala Leu Gln Asn Pro Ser Ala Val Pro Arg
545                 550                 555                 560

Phe Val Gln Ala Ile Cys Glu Gly Asp Asp Cys Gln Pro Pro Ala Tyr
            565                 570                 575

Thr Tyr Asn Asn Ile Thr Cys Ala Ser Pro Pro Glu Val Val Gly Leu
        580                 585                 590

Asp Leu Arg Asp Leu Ser Glu Ala His Phe Ala Pro Cys
    595                 600                 605

<210> SEQ ID NO 15
<211> LENGTH: 427
<212> TYPE: PRT
<213> ORGANISM: Homo sapiens

<400> SEQUENCE: 15

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
            85                  90                  95

Lys Asp Ala Ala Lys Ala Ala Thr Gly Glu Cys Thr Ala Thr Val Gly
        100                 105                 110

Lys Arg Ser Ser Thr Lys Phe Ser Val Ala Thr Gln Thr Cys Gln Ile
    115                 120                 125

Thr Pro Ala Glu Gly Pro Val Val Thr Ala Gln Tyr Asp Cys Leu Gly
130                 135                 140

Cys Val His Pro Ile Ser Thr Gln Ser Pro Asp Leu Glu Pro Ile Leu
```

```
           145                 150                 155                 160
       Arg His Gly Ile Gln Tyr Phe Asn Asn Thr Gln His Ser Ser Leu
                       165                 170                 175

Phe Met Leu Asn Glu Val Lys Arg Ala Gln Arg Gln Val Val Ala Gly
                   180                 185                 190

Leu Asn Phe Arg Met Thr Tyr Ser Ile Val Gln Thr Asn Cys Ser Lys
                   195                 200                 205

Glu Asn Phe Leu Phe Leu Thr Pro Asp Cys Lys Ser Leu Trp Asn Gly
                   210                 215                 220

Asp Thr Gly Glu Cys Thr Asp Asn Ala Tyr Ile Asp Ile Gln Leu Arg
       225                 230                 235                 240

Ile Ala Ser Phe Ser Gln Asn Cys Asp Ile Tyr Pro Gly Lys Asp Phe
                       245                 250                 255

Val Gln Pro Pro Thr Lys Ile Cys Val Gly Cys Pro Arg Asp Ile Pro
                   260                 265                 270

Thr Asn Ser Pro Glu Leu Glu Glu Thr Leu Thr His Thr Ile Thr Lys
                   275                 280                 285

Leu Asn Ala Glu Asn Asn Ala Thr Phe Tyr Phe Lys Ile Asp Asn Val
                   290                 295                 300

Lys Lys Ala Arg Val Gln Val Val Ala Gly Lys Lys Tyr Phe Ile Asp
       305                 310                 315                 320

Phe Val Ala Arg Glu Thr Thr Cys Ser Lys Glu Ser Asn Glu Glu Leu
                       325                 330                 335

Thr Glu Ser Cys Glu Thr Lys Lys Leu Gly Gln Ser Leu Asp Cys Asn
                       340                 345                 350

Ala Glu Val Tyr Val Val Pro Trp Glu Lys Lys Ile Tyr Pro Thr Val
                       355                 360                 365

Asn Cys Gln Pro Leu Gly Met Ile Ser Leu Met Lys Arg Pro Pro Gly
                       370                 375                 380

Phe Ser Pro Phe Arg Ser Arg Ile Gly Glu Ile Lys Glu Glu Thr
       385                 390                 395                 400

Thr Ser His Leu Arg Ser Cys Glu Tyr Lys Gly Arg Pro Pro Lys Ala
                       405                 410                 415

Gly Ala Glu Pro Ala Ser Glu Arg Glu Val Ser
                       420                 425

<210> SEQ ID NO 16
<211> LENGTH: 810
<212> TYPE: PRT
<213> ORGANISM: Homo sapiens

<400> SEQUENCE: 16

Met Glu His Lys Glu Val Val Leu Leu Leu Leu Phe Leu Lys Ser
       1               5                   10                  15

Gly Gln Gly Glu Pro Leu Asp Asp Tyr Val Asn Thr Gln Gly Ala Ser
                   20                  25                  30

Leu Phe Ser Val Thr Lys Lys Gln Leu Gly Ala Gly Ser Ile Glu Glu
                       35                  40                  45

Cys Ala Ala Lys Cys Glu Glu Asp Glu Glu Phe Thr Cys Arg Ala Phe
                   50                  55                  60

Gln Tyr His Ser Lys Glu Gln Gln Cys Val Ile Met Ala Glu Asn Arg
       65                  70                  75                  80

Lys Ser Ser Ile Ile Ile Arg Met Arg Asp Val Val Leu Phe Glu Lys
                       85                  90                  95
```

-continued

Lys Val Tyr Leu Ser Glu Cys Lys Thr Gly Asn Gly Lys Asn Tyr Arg
            100                 105                 110
Gly Thr Met Ser Lys Thr Lys Asn Gly Ile Thr Cys Gln Lys Trp Ser
        115                 120                 125
Ser Thr Ser Pro His Arg Pro Arg Phe Ser Pro Ala Thr His Pro Ser
    130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
            180                 185                 190
Tyr Asp Gly Lys Ile Ser Lys Thr Met Ser Gly Leu Glu Cys Gln Ala
        195                 200                 205
Trp Asp Ser Gln Ser Pro His Ala His Gly Tyr Ile Pro Ser Lys Phe
    210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Pro Ser Ser Gly Pro Thr
            260                 265                 270
Tyr Gln Cys Leu Lys Gly Thr Gly Glu Asn Tyr Arg Gly Asn Val Ala
        275                 280                 285
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asn Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys

```
            515                 520                 525
Asn Tyr Cys Arg Asn Pro Asp Gly Asp Val Gly Gly Pro Trp Cys Tyr
        530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                    565                 570                 575

Cys Pro Gly Arg Val Val Gly Cys Val Ala His Pro His Ser Trp
                580                 585                 590

Pro Trp Gln Val Ser Leu Arg Thr Arg Phe Gly Met His Phe Cys Gly
                595                 600                 605

Gly Thr Leu Ile Ser Pro Glu Trp Val Leu Thr Ala Ala His Cys Leu
        610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                    645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
        690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                    725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
        770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                    805                 810

<210> SEQ ID NO 17
<211> LENGTH: 158
<212> TYPE: PRT
<213> ORGANISM: Homo sapiens

<400> SEQUENCE: 17

Met Leu Cys Leu Leu Leu Thr Leu Gly Val Ala Leu Val Cys Gly Val
1               5                   10                  15

Pro Ala Met Asp Ile Pro Gln Thr Lys Gln Asp Leu Glu Leu Pro Lys
                20                  25                  30

Ala Pro Leu Arg Val His Ile Thr Ser Leu Leu Pro Thr Pro Glu Asp
            35                  40                  45

Asn Leu Glu Ile Val Leu His Arg Trp Glu Asn Asn Ser Cys Val Glu
        50                  55                  60

Lys Lys Val Leu Gly Glu Lys Thr Glu Asn Pro Lys Lys Phe Lys Ile
65                  70                  75                  80
```

```
Asn Tyr Thr Val Ala Asn Glu Ala Thr Leu Asp Thr Asp Tyr Asp
                85                  90                  95

Asn Phe Leu Phe Leu Cys Leu Gln Asp Thr Thr Thr Pro Ile Gln Ser
            100                 105                 110

Met Met Cys Gln Tyr Leu Ala Arg Val Leu Val Glu Asp Asp Glu Ile
            115                 120                 125

Met Gln Gly Phe Ile Arg Ala Phe Arg Pro Leu Pro Arg His Leu Trp
            130                 135                 140

Tyr Leu Leu Asp Leu Lys Gln Met Glu Glu Pro Cys Arg Phe
145                 150                 155

<210> SEQ ID NO 18
<211> LENGTH: 474
<212> TYPE: PRT
<213> ORGANISM: Homo sapiens

<400> SEQUENCE: 18

Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
            115                 120                 125

Gln Pro Gln Glu Phe Pro Thr Tyr Val Glu Pro Thr Asn Asp Glu Ile
            130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
            195                 200                 205

Leu Ser Leu Leu Thr Thr Leu Ser Asn Arg Val Cys Ser Gln Tyr Ala
            210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
            275                 280                 285

Leu Ser Thr Lys Asn Ser Lys Phe Glu Asp Cys Cys Gln Glu Lys Thr
            290                 295                 300
```

```
Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
                340                 345                 350

Arg Thr His Leu Pro Glu Val Phe Leu Ser Lys Val Leu Glu Pro Thr
            355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
                420                 425                 430

Ala Thr Pro Lys Glu Leu Ala Lys Leu Val Asn Lys Arg Ser Asp Phe
            435                 440                 445

Ala Ser Asn Cys Cys Ser Ile Asn Ser Pro Leu Tyr Cys Asp Ser
450                 455                 460

Glu Ile Asp Ala Glu Leu Lys Asn Ile Leu
465                 470

<210> SEQ ID NO 19
<211> LENGTH: 345
<212> TYPE: PRT
<213> ORGANISM: Homo sapiens

<400> SEQUENCE: 19

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
                20                  25                  30

Thr Val Val Pro Leu Lys Thr Phe Tyr Glu Pro Gly Glu Glu Ile Thr
                35                  40                  45

Tyr Ser Cys Lys Pro Gly Tyr Val Ser Arg Gly Gly Met Arg Lys Phe
50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
                100                 105                 110

Gly Phe Tyr Leu Asn Gly Ala Asp Ser Ala Lys Cys Thr Glu Glu Gly
            115                 120                 125

Lys Trp Ser Pro Glu Leu Pro Val Cys Ala Pro Ile Ile Cys Pro Pro
130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
```

```
            195                 200                 205
Ser Arg Pro Asp Asn Gly Phe Val Asn Tyr Pro Ala Lys Pro Thr Leu
210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                    245                 250                 255

Met Pro Ser Cys Lys Ala Ser Cys Lys Val Pro Val Lys Lys Ala Thr
                260                 265                 270

Val Val Tyr Gln Gly Glu Arg Val Lys Ile Gln Glu Lys Phe Lys Asn
            275                 280                 285

Gly Met Leu His Gly Asp Lys Val Ser Phe Phe Cys Lys Asn Lys Glu
        290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                    325                 330                 335

Thr Asp Ala Ser Asp Val Lys Pro Cys
                340                 345

<210> SEQ ID NO 20
<211> LENGTH: 1744
<212> TYPE: PRT
<213> ORGANISM: Homo sapiens

<400> SEQUENCE: 20

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
210                 215                 220
```

-continued

```
Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
            245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
            275                 280                 285

Glu Asp Gly Lys Lys Thr Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
            325                 330                 335

Arg Leu Tyr Val Ala Ala Ile Ile Glu Tyr Pro Gly Gly Glu Met
            340                 345                 350

Glu Glu Ala Glu Leu Thr Ser Trp Tyr Phe Val Ser Ser Pro Phe Ser
            355                 360                 365

Leu Asp Leu Ser Lys Thr Lys Arg His Leu Val Pro Gly Ala Pro Phe
370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Pro Gly Ser Val Pro
            405                 410                 415

Glu Val Gln Asp Ile Gln Gln Asn Thr Asp Gly Ser Gln Val Ser
            420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
            450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
            485                 490                 495

Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
            565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
            610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
```

```
            645                 650                 655
Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
                725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Glu Asp Leu Ile Asp
            755                 760                 765

Glu Asp Asp Ile Pro Val Arg Ser Phe Phe Pro Glu Asn Trp Leu Trp
            770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
            850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Glu Leu
            930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
                980                 985                 990

Gly Ala Leu Ser Pro Gly Gly Val  Ala Ser Leu Leu Arg  Leu Pro Arg
            995                 1000                 1005

Gly Cys  Gly Glu Gln Thr Met  Ile Tyr Leu Ala Pro  Thr Leu Ala
            1010                 1015                 1020

Ala Ser  Arg Tyr Leu Asp Lys  Thr Glu Gln Trp Ser  Thr Leu Pro
            1025                 1030                 1035

Pro Glu  Thr Lys Asp His Ala  Val Asp Leu Ile Gln  Lys Gly Tyr
            1040                 1045                 1050

Met Arg  Ile Gln Gln Phe Arg  Lys Ala Asp Gly Ser  Tyr Ala Ala
            1055                 1060                 1065
```

```
Trp Leu Ser Arg Gly Ser Ser Thr Trp Leu Thr Ala Phe Val Leu
    1070            1075            1080

Lys Val Leu Ser Leu Ala Gln Glu Gln Val Gly Gly Ser Pro Glu
    1085            1090            1095

Lys Leu Gln Glu Thr Ser Asn Trp Leu Leu Ser Gln Gln Gln Ala
    1100            1105            1110

Asp Gly Ser Phe Gln Asp Leu Ser Pro Val Ile His Arg Ser Met
    1115            1120            1125

Gln Gly Gly Leu Val Gly Asn Asp Glu Thr Val Ala Leu Thr Ala
    1130            1135            1140

Phe Val Thr Ile Ala Leu His His Gly Leu Ala Val Phe Gln Asp
    1145            1150            1155

Glu Gly Ala Glu Pro Leu Lys Gln Arg Val Glu Ala Ser Ile Ser
    1160            1165            1170

Lys Ala Ser Ser Phe Leu Gly Glu Lys Ala Ser Ala Gly Leu Leu
    1175            1180            1185

Gly Ala His Ala Ala Ala Ile Thr Ala Tyr Ala Leu Thr Leu Thr
    1190            1195            1200

Lys Ala Pro Ala Asp Leu Arg Gly Val Ala His Asn Asn Leu Met
    1205            1210            1215

Ala Met Ala Gln Glu Thr Gly Asp Asn Leu Tyr Trp Gly Ser Val
    1220            1225            1230

Thr Gly Ser Gln Ser Asn Ala Val Ser Pro Thr Pro Ala Pro Arg
    1235            1240            1245

Asn Pro Ser Asp Pro Met Pro Gln Ala Pro Ala Leu Trp Ile Glu
    1250            1255            1260

Thr Thr Ala Tyr Ala Leu Leu His Leu Leu Leu His Glu Gly Lys
    1265            1270            1275

Ala Glu Met Ala Asp Gln Ala Ala Ala Trp Leu Thr Arg Gln Gly
    1280            1285            1290

Ser Phe Gln Gly Gly Phe Arg Ser Thr Gln Asp Thr Val Ile Ala
    1295            1300            1305

Leu Asp Ala Leu Ser Ala Tyr Trp Ile Ala Ser His Thr Thr Glu
    1310            1315            1320

Glu Arg Gly Leu Asn Val Thr Leu Ser Ser Thr Gly Arg Asn Gly
    1325            1330            1335

Phe Lys Ser His Ala Leu Gln Leu Asn Asn Arg Gln Ile Arg Gly
    1340            1345            1350

Leu Glu Glu Glu Leu Gln Phe Ser Leu Gly Ser Lys Ile Asn Val
    1355            1360            1365

Lys Val Gly Gly Asn Ser Lys Gly Thr Leu Lys Val Leu Arg Thr
    1370            1375            1380

Tyr Asn Val Leu Asp Met Lys Asn Thr Thr Cys Gln Asp Leu Gln
    1385            1390            1395

Ile Glu Val Thr Val Lys Gly His Val Glu Tyr Thr Met Glu Ala
    1400            1405            1410

Asn Glu Asp Tyr Glu Asp Tyr Glu Tyr Asp Glu Leu Pro Ala Lys
    1415            1420            1425

Asp Asp Pro Asp Ala Pro Leu Gln Pro Val Thr Pro Leu Gln Leu
    1430            1435            1440

Phe Glu Gly Arg Arg Asn Arg Arg Arg Glu Ala Pro Lys Val
    1445            1450            1455
```

```
Val Glu Gln Glu Ser Arg Val His Tyr Thr Val Cys Ile Trp
    1460              1465               1470

Arg Asn Gly Lys Val Gly Leu Ser Gly Met Ala Ile Ala Asp Val
    1475              1480               1485

Thr Leu Leu Ser Gly Phe His Ala Leu Arg Ala Asp Leu Glu Lys
    1490              1495               1500

Leu Thr Ser Leu Ser Asp Arg Tyr Val Ser His Phe Glu Thr Glu
    1505              1510               1515

Gly Pro His Val Leu Leu Tyr Phe Asp Ser Val Pro Thr Ser Arg
    1520              1525               1530

Glu Cys Val Gly Phe Glu Ala Val Gln Glu Val Pro Val Gly Leu
    1535              1540               1545

Val Gln Pro Ala Ser Ala Thr Leu Tyr Asp Tyr Tyr Asn Pro Glu
    1550              1555               1560

Arg Arg Cys Ser Val Phe Tyr Gly Ala Pro Ser Lys Ser Arg Leu
    1565              1570               1575

Leu Ala Thr Leu Cys Ser Ala Glu Val Cys Gln Cys Ala Glu Gly
    1580              1585               1590

Lys Cys Pro Arg Gln Arg Arg Ala Leu Glu Arg Gly Leu Gln Asp
    1595              1600               1605

Glu Asp Gly Tyr Arg Met Lys Phe Ala Cys Tyr Tyr Pro Arg Val
    1610              1615               1620

Glu Tyr Gly Phe Gln Val Lys Val Leu Arg Glu Asp Ser Arg Ala
    1625              1630               1635

Ala Phe Arg Leu Phe Glu Thr Lys Ile Thr Gln Val Leu His Phe
    1640              1645               1650

Thr Lys Asp Val Lys Ala Ala Asn Gln Met Arg Asn Phe Leu
    1655              1660               1665

Val Arg Ala Ser Cys Arg Leu Arg Leu Glu Pro Gly Lys Glu Tyr
    1670              1675               1680

Leu Ile Met Gly Leu Asp Gly Ala Thr Tyr Asp Leu Glu Gly His
    1685              1690               1695

Pro Gln Tyr Leu Leu Asp Ser Asn Ser Trp Ile Glu Glu Met Pro
    1700              1705               1710

Ser Glu Arg Leu Cys Arg Ser Thr Arg Gln Arg Ala Ala Cys Ala
    1715              1720               1725

Gln Leu Asn Asp Phe Leu Gln Glu Tyr Gly Thr Gln Gly Cys Gln
    1730              1735               1740

Val

<210> SEQ ID NO 21
<211> LENGTH: 433
<212> TYPE: PRT
<213> ORGANISM: Homo sapiens

<400> SEQUENCE: 21

Met Glu Arg Met Leu Pro Leu Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
        35                  40                  45

Leu Ala Ser Ala Asn Val Asp Phe Ala Phe Ser Leu Tyr Lys Gln Leu
    50                  55                  60
```

```
Val Leu Lys Ala Leu Asp Lys Asn Val Ile Phe Ser Pro Leu Ser Ile
 65                  70                  75                  80

Ser Thr Ala Leu Ala Phe Leu Ser Leu Gly Ala His Asn Thr Thr Leu
                 85                  90                  95

Thr Glu Ile Leu Lys Ala Ser Ser Pro His Gly Asp Leu Leu Arg
            100                 105                 110

Gln Lys Phe Thr Gln Ser Phe Gln His Leu Arg Ala Pro Ser Ile Ser
            115                 120                 125

Ser Ser Asp Glu Leu Gln Leu Ser Met Gly Asn Ala Met Phe Val Lys
        130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Pro Asp Ser Gln Thr Met Met Val Leu Val
            195                 200                 205

Asn Tyr Ile Phe Phe Lys Ala Lys Trp Glu Met Pro Phe Asp Pro Gln
210                 215                 220

Asp Thr His Gln Ser Arg Phe Tyr Leu Ser Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
            260                 265                 270

Ser Ala Leu Phe Ile Leu Pro Asp Gln Asp Lys Met Glu Glu Val Glu
            275                 280                 285

Ala Met Leu Leu Pro Glu Thr Leu Lys Arg Trp Arg Asp Ser Leu Glu
            290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Val Val Ser Asp Val Phe Glu Glu
            355                 360                 365

Gly Thr Glu Ala Ser Ala Ala Thr Ala Val Lys Ile Thr Leu Leu Ser
            370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Ser Lys Pro Arg Ala Cys Ile Lys Gln Trp Gly Ser
            420                 425                 430

Gln

<210> SEQ ID NO 22
<211> LENGTH: 493
<212> TYPE: PRT
<213> ORGANISM: Homo sapiens

<400> SEQUENCE: 22
```

```
Gly Ser Gly Ser Gly His Ser Ser Ser Tyr Glu Gln His Gly Ser Arg
  1               5                  10                 15

Ser Gly Gln Ser Ser Arg Gly Glu Gln His Gly Ser Ser Ser Gly Ser
             20                  25                  30

Ser Ser Ser Tyr Gly Gln His Gly Ser Gly Ser Arg Gln Ser Leu Gly
             35                  40                  45

His Gly Gln His Gly Ser Gly Ser Gly Gln Ser Pro Ser Pro Ser Arg
 50                  55                  60

Gly Arg His Gly Ser Gly Ser Gly Gln Ser Ser Tyr Ser Pro Tyr
 65                  70                  75                  80

Gly Ser Gly Ser Gly Trp Ser Ser Ser Arg Gly Pro Tyr Glu Ser Gly
                 85                  90                  95

Ser Gly His Ser Ser Gly Leu Gly His Arg Glu Ser Arg Ser Gly Gln
            100                 105                 110

Ser Ser Gly Tyr Gly Gln His Gly Ser Ser Gly His Ser Ser Thr
            115                 120                 125

His Gly Gln His Gly Ser Thr Ser Gly Gln Ser Ser Cys Gly Gln
130                 135                 140

His Gly Ala Ser Ser Gly Gln Ser Ser Ser His Gly Gln His Gly Ser
145                 150                 155                 160

Gly Ser Ser Gln Ser Ser Gly Tyr Gly Arg Gln Gly Ser Gly Ser Gly
                165                 170                 175

Gln Ser Pro Gly His Ser Gln Arg Gly Ser Gly Ser Arg Gln Ser Pro
            180                 185                 190

Ser Tyr Gly Arg His Gly Ser Gly Ser Gly Arg Ser Ser Ser Ser Gly
        195                 200                 205

Gln His Gly Ser Gly Leu Gly Glu Ser Ser Gly Phe Gly His His Glu
        210                 215                 220

Ser Ser Ser Gly Gln Ser Ser Ser Tyr Ser Gln His Gly Ser Gly Ser
225                 230                 235                 240

Gly His Ser Ser Gly Tyr Gly Gln His Gly Ser Arg Ser Gly Gln Ser
                245                 250                 255

Ser Arg Gly Glu Arg His Gly Ser Ser Ser Gly Ser Ser Ser His Tyr
        260                 265                 270

Gly Gln His Gly Ser Gly Ser Arg Gln Ser Ser Gly His Gly Arg Gln
        275                 280                 285

Gly Ser Gly Ser Gly Gln Ser Pro Ser Arg Gly Arg His Gly Ser Gly
        290                 295                 300

Leu Gly His Ser Ser His Gly Gln His Gly Ser Gly Ser Gly Arg
305                 310                 315                 320

Ser Ser Ser Arg Gly Pro Tyr Glu Ser Arg Ser Gly His Ser Ser Val
            325                 330                 335

Phe Gly Gln His Glu Ser Gly Ser Gly His Ser Ser Ala Tyr Ser Gln
            340                 345                 350

His Gly Ser Gly Ser Gly His Phe Cys Ser Gly Gln His Gly Ser
            355                 360                 365

Thr Ser Gly Gln Ser Ser Thr Phe Asp Gln Glu Gly Ser Ser Thr Gly
            370                 375                 380

Gln Ser Ser Ser Tyr Gly His Arg Gly Ser Ser Ser Gln Ser Ser
385                 390                 395                 400

Gly Tyr Gly Arg His Gly Ala Gly Ser Gly Gln Ser Leu Ser His Gly
                405                 410                 415

Arg His Gly Ser Gly Ser Gly Gln Ser Ser Ser Tyr Gly Gln His Gly
```

420                 425                 430
Ser Gly Ser Gly Gln Ser Ser Gly Tyr Ser Gln His Gly Ser Gly Ser
            435                 440                 445

Gly Gln Asp Gly Tyr Ser Tyr Cys Lys Gly Gly Ser Asn His Asp Gly
    450                 455                 460

Gly Ser Ser Gly Ser Tyr Phe Leu Ser Phe Pro Ser Ser Thr Ser Pro
465                 470                 475                 480

Tyr Glu Tyr Val Gln Glu Gln Arg Cys Tyr Phe Tyr Gln
                485                 490

<210> SEQ ID NO 23
<211> LENGTH: 935
<212> TYPE: PRT
<213> ORGANISM: Homo sapiens

<400> SEQUENCE: 23

Met Lys Arg Leu Thr Cys Phe Phe Ile Cys Phe Phe Leu Ser Glu Val
1               5                   10                  15

Ser Gly Phe Glu Ile Pro Ile Asn Gly Leu Ser Glu Phe Val Asp Tyr
                20                  25                  30

Glu Asp Leu Val Glu Leu Ala Pro Gly Lys Phe Gln Leu Val Ala Glu
            35                  40                  45

Asn Arg Arg Tyr Gln Glu Val Asp Gln Val Thr Leu Tyr Ser Tyr
        50                  55                  60

Lys Val Gln Ser Thr Ile Thr Ser Arg Met Ala Thr Thr Met Ile Gln
65              70                  75                  80

Ser Lys Val Val Asn Asn Ser Pro Gln Pro Gln Asn Val Val Phe Asp
                85                  90                  95

Val Gln Ile Pro Lys Gly Ala Phe Ile Ser Asn Phe Ser Met Thr Val
            100                 105                 110

Asp Gly Lys Thr Phe Arg Ser Ser Ile Lys Glu Lys Thr Val Gly Arg
        115                 120                 125

Ala Leu Tyr Ala Gln Ala Arg Ala Lys Gly Lys Thr Ala Gly Leu Val
    130                 135                 140

Arg Ser Ser Ala Leu Asp Met Glu Asn Phe Arg Thr Glu Val Asn Val
145                 150                 155                 160

Leu Pro Gly Ala Lys Val Gln Phe Glu Leu His Tyr Gln Glu Val Lys
                165                 170                 175

Trp Arg Lys Leu Gly Ser Tyr Glu His Arg Ile Tyr Leu Gln Pro Gly
            180                 185                 190

Arg Leu Ala Lys His Leu Glu Val Asp Val Trp Val Ile Glu Pro Gln
        195                 200                 205

Gly Leu Arg Phe Leu His Val Pro Asp Thr Phe Glu Gly His Phe Asp
    210                 215                 220

Gly Val Pro Val Ile Ser Lys Gly Gln Gln Lys Ala His Val Ser Phe
225                 230                 235                 240

Lys Pro Thr Val Ala Gln Gln Arg Ile Cys Pro Asn Cys Arg Glu Thr
                245                 250                 255

Ala Val Asp Gly Glu Leu Val Val Leu Tyr Asp Val Lys Arg Glu Glu
            260                 265                 270

Lys Ala Gly Glu Leu Glu Val Phe Asn Gly Tyr Phe Val His Phe Phe
        275                 280                 285

Ala Pro Asp Asn Leu Asp Pro Ile Pro Lys Asn Ile Leu Phe Val Ile
    290                 295                 300

```
Asp Val Ser Gly Ser Met Trp Gly Val Lys Met Lys Gln Thr Val Glu
305                 310                 315                 320

Ala Met Lys Thr Ile Leu Asp Asp Leu Arg Ala Glu Asp His Phe Ser
            325                 330                 335

Val Ile Asp Phe Asn Gln Asn Ile Arg Thr Trp Arg Asn Asp Leu Ile
            340                 345                 350

Ser Ala Thr Lys Thr Gln Val Ala Asp Ala Lys Arg Tyr Ile Glu Lys
            355                 360                 365

Ile Gln Pro Ser Gly Gly Thr Asn Ile Asn Glu Ala Leu Leu Arg Ala
370                 375                 380

Ile Phe Ile Leu Asn Glu Ala Asn Asn Leu Gly Leu Leu Asp Pro Asn
385                 390                 395                 400

Ser Val Ser Leu Ile Ile Leu Val Ser Asp Gly Asp Pro Thr Val Gly
            405                 410                 415

Glu Leu Lys Leu Ser Lys Ile Gln Lys Asn Val Lys Glu Asn Ile Gln
            420                 425                 430

Asp Asn Ile Ser Leu Phe Ser Leu Gly Met Gly Phe Asp Val Asp Tyr
            435                 440                 445

Asp Phe Leu Lys Arg Leu Ser Asn Glu Asn His Gly Ile Ala Gln Arg
450                 455                 460

Ile Tyr Gly Asn Gln Asp Thr Ser Ser Gln Leu Lys Lys Phe Tyr Asn
465                 470                 475                 480

Gln Val Ser Thr Pro Leu Leu Arg Asn Val Gln Phe Asn Tyr Pro His
            485                 490                 495

Thr Ser Val Thr Asp Val Thr Gln Asn Asn Phe His Asn Tyr Phe Gly
            500                 505                 510

Gly Ser Glu Ile Val Val Ala Gly Lys Phe Asp Pro Ala Lys Leu Asp
            515                 520                 525

Gln Ile Glu Ser Val Ile Thr Ala Thr Ser Ala Asn Thr Gln Leu Val
530                 535                 540

Leu Glu Thr Leu Ala Gln Met Asp Asp Leu Gln Asp Phe Leu Ser Lys
545                 550                 555                 560

Asp Lys His Ala Asp Pro Asp Phe Thr Arg Lys Leu Trp Ala Tyr Leu
            565                 570                 575

Thr Ile Asn Gln Leu Leu Ala Glu Arg Ser Leu Ala Pro Thr Ala Ala
            580                 585                 590

Ala Lys Arg Arg Ile Thr Arg Ser Ile Leu Gln Met Ser Leu Asp His
            595                 600                 605

His Ile Val Thr Pro Leu Thr Ser Leu Val Ile Glu Asn Glu Ala Gly
            610                 615                 620

Asp Glu Arg Met Leu Ala Asp Ala Pro Pro Gln Asp Pro Ser Cys Cys
625                 630                 635                 640

Ser Gly Ala Leu Tyr Tyr Gly Ser Lys Val Val Pro Asp Ser Thr Pro
            645                 650                 655

Ser Trp Ala Asn Pro Ser Pro Thr Pro Val Ile Ser Met Leu Ala Gln
            660                 665                 670

Gly Ser Gln Val Leu Glu Ser Thr Pro Pro His Val Met Arg Val
            675                 680                 685

Glu Asn Asp Pro His Phe Ile Ile Tyr Leu Pro Lys Ser Gln Lys Asn
            690                 695                 700

Ile Cys Phe Asn Ile Asp Ser Glu Pro Gly Lys Ile Leu Asn Leu Val
705                 710                 715                 720

Ser Asp Pro Glu Ser Gly Ile Val Val Asn Gly Gln Leu Val Gly Ala
```

```
                    725                 730                 735
Lys Lys Pro Asn Asn Gly Lys Leu Ser Thr Tyr Phe Gly Lys Leu Gly
            740                 745                 750

Phe Tyr Phe Gln Ser Glu Asp Ile Lys Ile Glu Ile Ser Thr Glu Thr
            755                 760                 765

Ile Thr Leu Ser His Gly Ser Ser Thr Phe Ser Leu Ser Trp Ser Asp
            770                 775                 780

Thr Ala Gln Val Thr Asn Gln Arg Val Gln Ile Ser Val Lys Lys Glu
785                 790                 795                 800

Lys Val Val Thr Ile Thr Leu Asp Lys Glu Met Ser Phe Ser Val Leu
                805                 810                 815

Leu His Arg Val Trp Lys Lys His Pro Val Asn Val Asp Phe Leu Gly
                820                 825                 830

Ile Tyr Ile Pro Pro Thr Asn Lys Phe Ser Pro Lys Ala His Gly Leu
                835                 840                 845

Ile Gly Gln Phe Met Gln Glu Pro Lys Ile His Ile Phe Asn Glu Arg
                850                 855                 860

Pro Gly Lys Asp Pro Glu Lys Pro Glu Ala Ser Met Glu Val Lys Gly
865                 870                 875                 880

Gln Lys Leu Ile Ile Thr Arg Gly Leu Gln Lys Asp Tyr Arg Thr Asp
                885                 890                 895

Leu Val Phe Gly Thr Asp Val Thr Cys Trp Phe Val His Asn Ser Gly
                900                 905                 910

Lys Gly Phe Ile Asp Gly His Tyr Lys Asp Tyr Phe Val Pro Gln Leu
                915                 920                 925

Tyr Ser Phe Leu Lys Arg Pro
                930                 935

<210> SEQ ID NO 24
<211> LENGTH: 382
<212> TYPE: PRT
<213> ORGANISM: Homo sapiens

<400> SEQUENCE: 24

Met Gly Leu Leu Leu Pro Leu Ala Pro Cys Ile Leu Val Leu Cys Cys
1               5                   10                  15

Gly Ala Met Ser Pro Pro Gln Leu Ala Leu Asn Pro Ser Ala Leu Leu
            20                  25                  30

Ser Arg Gly Cys Asn Asp Ser Asp Val Leu Ala Val Ala Gly Phe Ala
        35                  40                  45

Leu Arg Asp Ile Asn Lys Asp Arg Lys Asp Gly Tyr Val Leu Arg Leu
    50                  55                  60

Asn Arg Val Asn Asp Ala Gln Glu Tyr Arg Arg Gly Gly Leu Gly Ser
65                  70                  75                  80

Leu Phe Tyr Leu Thr Leu Asp Val Leu Glu Thr Asp Cys His Val Leu
                85                  90                  95

Arg Lys Lys Ala Trp Gln Asp Cys Gly Met Arg Ile Phe Phe Glu Ser
                100                 105                 110

Val Tyr Gly Gln Cys Lys Ala Ile Phe Tyr Met Asn Asn Pro Ser Arg
            115                 120                 125

Val Leu Tyr Leu Ala Ala Tyr Asn Cys Thr Leu Arg Pro Val Ser Lys
        130                 135                 140

Lys Lys Ile Tyr Met Thr Cys Pro Asp Cys Pro Ser Ser Ile Pro Thr
145                 150                 155                 160
```

```
Asp Ser Ser Asn His Gln Val Leu Glu Ala Thr Glu Ser Leu Ala
                165                 170                 175

Lys Tyr Lys Asn Glu Asn Thr Ser Lys Gln Tyr Ser Leu Phe Lys Val
            180                 185                 190

Thr Arg Ala Ser Ser Gln Trp Val Val Gly Pro Ser Tyr Phe Val Glu
        195                 200                 205

Tyr Leu Ile Lys Glu Ser Pro Cys Thr Lys Ser Gln Ala Ser Ser Cys
    210                 215                 220

Ser Leu Gln Ser Ser Asp Ser Val Pro Val Gly Leu Cys Lys Gly Ser
225                 230                 235                 240

Leu Thr Arg Thr His Trp Glu Lys Phe Val Ser Val Thr Cys Asp Phe
                245                 250                 255

Phe Glu Ser Gln Ala Pro Ala Thr Gly Ser Glu Asn Ser Ala Val Asn
            260                 265                 270

Gln Lys Pro Thr Asn Leu Pro Lys Val Glu Glu Ser Gln Gln Lys Asn
        275                 280                 285

Thr Pro Pro Thr Asp Ser Pro Ser Lys Ala Gly Pro Arg Gly Ser Val
    290                 295                 300

Gln Tyr Leu Pro Asp Leu Asp Asp Lys Asn Ser Gln Glu Lys Gly Pro
305                 310                 315                 320

Gln Glu Ala Phe Pro Val His Leu Asp Leu Thr Thr Asn Pro Gln Gly
                325                 330                 335

Glu Thr Leu Asp Ile Ser Phe Leu Phe Leu Glu Pro Met Glu Glu Lys
            340                 345                 350

Leu Val Val Leu Pro Phe Pro Lys Glu Lys Ala Arg Thr Ala Glu Cys
        355                 360                 365

Pro Gly Pro Ala Gln Asn Ala Ser Pro Leu Val Leu Pro Pro
    370                 375                 380

<210> SEQ ID NO 25
<211> LENGTH: 930
<212> TYPE: PRT
<213> ORGANISM: Homo sapiens

<400> SEQUENCE: 25

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Ile Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160
```

-continued

Leu Lys Val Arg Pro Gln Gln Leu Val Lys His Leu Gln Met Asp Ile
            165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
            195                 200                 205

Thr Lys Ala His Ile Arg Phe Lys Pro Thr Leu Ser Gln Gln Gln Lys
210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
            245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
            275                 280                 285

Lys Ile Gln Gln Thr Arg Glu Ala Leu Ile Lys Ile Leu Asp Asp Leu
            290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
            325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
            355                 360                 365

Glu Glu Arg Leu Pro Glu Gly Ser Val Ser Leu Ile Ile Leu Leu Thr
370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
            405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
            435                 440                 445

Gln Leu Gln Asp Phe Tyr Gln Glu Val Ala Asn Pro Leu Leu Thr Ala
            450                 455                 460

Val Thr Phe Glu Tyr Pro Ser Asn Ala Val Glu Val Thr Gln Asn
465                 470                 475                 480

Asn Phe Arg Leu Leu Phe Lys Gly Ser Glu Met Val Val Ala Gly Lys
            485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
            515                 520                 525

Gln Glu Ala Glu Phe Gln Ser Pro Lys Tyr Ile Phe His Asn Phe Met
            530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
            565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
    610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Pro Ala Thr Ser Asn Pro
    690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Ser Asp Pro Glu Gln Gly Val Glu
        755                 760                 765

Val Thr Gly Gln Tyr Glu Arg Glu Lys Ala Gly Phe Ser Trp Ile Glu
    770                 775                 780

Val Thr Phe Lys Asn Pro Leu Val Trp Val His Ala Ser Pro Glu His
785                 790                 795                 800

Val Val Val Thr Arg Asn Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Arg Asp Thr
    850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Gly Arg Arg Thr
                885                 890                 895

Leu Arg Val Gln Gly Asn Asp His Ser Ala Thr Arg Glu Arg Leu
            900                 905                 910

Asp Tyr Gln Glu Gly Pro Pro Gly Val Glu Ile Ser Cys Trp Ser Val
        915                 920                 925

Glu Leu
    930

<210> SEQ ID NO 26
<211> LENGTH: 375
<212> TYPE: PRT
<213> ORGANISM: Homo sapiens

<400> SEQUENCE: 26

Met Glu Arg Ala Ser Cys Leu Leu Leu Leu Leu Leu Pro Leu Val His
1               5                   10                  15

Val Ser Ala Thr Thr Pro Glu Pro Cys Glu Leu Asp Asp Glu Asp Phe
                 20                  25                  30

Arg Cys Val Cys Asn Phe Ser Glu Pro Gln Pro Asp Trp Ser Glu Ala
             35                  40                  45

Phe Gln Cys Val Ser Ala Val Glu Val Glu Ile His Ala Gly Gly Leu
 50                  55                  60

Asn Leu Glu Pro Phe Leu Lys Arg Val Asp Ala Asp Ala Asp Pro Arg
 65                  70                  75                  80

Gln Tyr Ala Asp Thr Val Lys Ala Leu Arg Val Arg Arg Leu Thr Val
                 85                  90                  95

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Glu Leu
290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
370                 375

<210> SEQ ID NO 27
<211> LENGTH: 418
<212> TYPE: PRT
<213> ORGANISM: Homo sapiens

<400> SEQUENCE: 27

Met Gln Ala Leu Val Leu Leu Leu Cys Ile Gly Ala Leu Leu Gly His

-continued

```
1               5                   10                  15
Ser Ser Cys Gln Asn Pro Ala Ser Pro Pro Glu Glu Gly Ser Pro Asp
                20                  25                  30

Pro Asp Ser Thr Gly Ala Leu Val Glu Glu Asp Pro Phe Phe Lys
        35                  40                  45

Val Pro Val Asn Lys Leu Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
                130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
                210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
                275                 280                 285

Ile Glu Glu Ser Leu Thr Ser Glu Phe Ile His Asp Ile Asp Arg Glu
                290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe
                370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```